United States Patent [19]

Keck et al.

[11] 4,362,738
[45] Dec. 7, 1982

[54] ESTERS AND AMIDES CONTAINING THE 1-(4-CHLOROBENZOYL)-5-METHOXY-2-METHYL-1H-INDOLE-3-ACETYL MOIETY

[75] Inventors: Johannes Keck; Gerd Krüger; Helmut Pieper, all of Biberach; Klaus Noll, Warthausen; Günther Engelhardt; Norbert Promberger, both of Biberach; Rainer Zimmermann, Mittelbiberach, all of Fed. Rep. of Germany

[73] Assignee: Dr. Karl Thomae GmbH, Biberach, Fed. Rep. of Germany

[21] Appl. No.: 158,587

[22] Filed: Jun. 11, 1980

[30] Foreign Application Priority Data

Jun. 30, 1979 [DE] Fed. Rep. of Germany ....... 2926472

[51] Int. Cl.$^3$ .................. C07D 279/18; A61K 27/00
[52] U.S. Cl. ..................................... 424/274; 544/37; 546/184; 424/248.4; 424/244; 424/250; 424/330; 548/494; 548/495
[58] Field of Search ................ 260/326.13 A; 424/274

[56] References Cited

FOREIGN PATENT DOCUMENTS 1168450 10/1969 United Kingdom ...... 260/326.14 A

Primary Examiner—David B. Springer
Attorney, Agent, or Firm—Hammond & Littell, Weissenberger & Muserlian

[57] ABSTRACT

Compounds of the formula

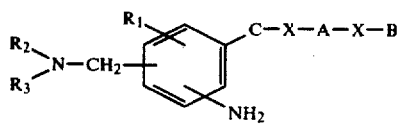

wherein
each X, which may be identical or different from the other X, is oxygen or imino;

$R_1$ is hydrogen, fluorine, chlorine or bromine;

$R_2$ and $R_3$, which may be identical or different from each other, are each hydrogen; unsubstituted or mono-substituted alkyl of 1 to 6 carbon atoms, where the substituent is phenyl or dialkylamino with 1 to 3 carbon atoms in each alkyl moiety; pyridyl; or cycloalkyl of 5 to 7 carbon atoms;

$R_2$ and $R_3$, together with each other and the nitrogen atoms to which they are attached, are pyrrolidino, piperidino, hexamethyleneimino, morpholino, N-aryl-piperazino or N-(alkyl of 1 to 3 carbon atoms)-piperazino;

A is cycloalkylene of 5 to 7 carbon atoms; unsubstituted or substituted alkylene of 2 to 10 carbon atoms, where the substituents are one to two alkyls of 1 to 3 carbon atoms each, one to two carbalkoxys of 2 to 4 carbon atoms each, one to two phenyls, one to four hydroxyls, one halomethyl, one hydroxymethyl, one alkanoyloxy of 1 to 18 carbon atoms, one alkanoyloxymethyl of 1 to 18 carbon atoms in the alkanoyl moiety or one

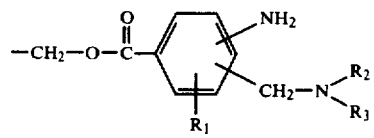

where $R_1$, $R_2$ and $R_3$ have the meanings previously defined; or alkylene of 2 to 10 carbon atoms interrupted by oxygen, sulfur, sulfoxide, sulfonyl, phenyl, cyclohexyl, pyridyl, piperazino or unsubstituted or substituted imino, where the substituent on the imino group is alkyl of 1 to 6 carbon atoms, phenyl or phenylalkyl of 1 to 3 carbon atoms in the alkyl moiety;

B is the acyl residue of an antiphlogistic carboxylic acid;

and their non-toxic, pharmacologically acceptable acid addition salts. The compounds as well as their salts are useful as anti-inflammatories.

7 Claims, No Drawings

ESTERS AND AMIDES CONTAINING THE 1-(4-CHLOROBENZOYL)-5-METHOXY-2-METHYL-1H-INDOLE-3-ACETYL MOIETY

This invention relates to novel benzoyl derivatives and non-toxic, pharmacologically acceptable acid addition salts thereof, to methods of preparing these compounds, to pharmaceutical compositions containing them as active ingredients, and to methods of using them as anti-inflammatories.

More particularly, the present invention relates to a novel class of compounds represented by the formula

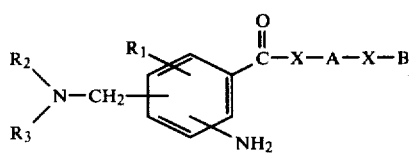

(I)

wherein
- each X, which may be identical to or different from the other X, is oxygen or imino;
- $R_1$ is hydrogen, fluorine, chlorine or bromine;
- $R_2$ and $R_3$, which may be identical to or different from each other, are each hydrogen; unsubstituted or monosubstituted alkyl of 1 to 6 carbon atoms, where the substituent is phenyl or dialkylamino with 1 to 3 carbon atoms in each alkyl moiety; pyridyl; or cycloalkyl of 5 to 7 carbon atoms;
- $R_2$ and $R_3$, together with each other and the nitrogen atom to which they are attached, are pyrrolidino, piperidino, hexamethyleneimino, morpholino, N-aryl-piperazino or N-(alkyl of 1 to 3 carbon atoms)-piperazino;
- A is cycloalkylene of 5 to 7 carbon atoms; unsubstituted or substituted alkylene of 2 to 10 carbon atoms, where the substituents are one to two alkyls of 1 to 3 carbon atoms each, one to two carbalkoxys of 2 to 4 carbon atoms each, one to two phenyls, one to four hydroxyls, one halomethyl, one hydroxymethyl, one alkanoyloxy of 1 to 18 carbon atoms, one alkanoyloxymethyl of 1 to 18 carbon atoms in the alkanoyl moiety or one

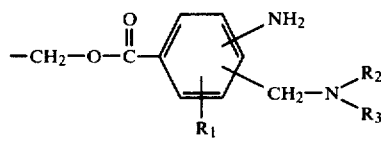

where $R_1$, $R_2$ and $R_3$ have the meanings previously defined; or alkylene of 2 to 10 carbon atoms interrupted by oxygen, sulfur, sulfoxide, sulfonyl, phenyl, cyclohexyl, pyridyl, piperazino or unsubstituted or substituted imino, where the substituent on the imino group is alkyl of 1 to 6 carbon atoms, phenyl or phenylalkyl of 1 to 3 carbon atoms in the alkyl moiety;

B is the acyl residue of an antiphlogistic carboxylic acid, such as
- 1-(4-chlorobenzoyl)-5-methoxy-2-methyl-1H-indole-3-acetyl,
- (+)-6-methoxy-α-methyl-2-naphthaline-acetyl,
- 5-benzoyl-α-methyl-2-thiophene-acetyl,
- 1-methyl-5-(4-methylbenzoyl)-1H-pyrrole-2-acetyl,
- 5-fluoro-2-methyl-1-{[4-(methylsulfinyl)-phenyl]-methylene}-1H-indene-3-acetyl,
- 6,11-dihydro-11-oxo-dibenz[b,e]oxepine-3-acetyl,
- 6,11-dihydro-11-oxo-dibenz[b,e]oxepine-2-acetyl,
- α-methyl-5-oxo-5H-dibenzo[a,d]cycloheptane-2-acetyl,
- 2p-(4-chlorophenyl)-α-methyl-5-benzoxazoleacetyl,
- 6-chloro-α-methyl-9H-carbazole-2-acetyl,
- 1,3,4,9-tetrahydro-1-propyl-pyrano[3,4-b]indole-1-acetyl,
- 1,8-diethyl-1,3,4,9-tetrahydro-pyrano[3,4-b]indole-1-acetyl,
- 2-{[4,5-bis-(4-chlorophenyl)-2-oxazolyl]thio}propanoyl,
- 1-(4-chlorophenyl)-2,5-dimethyl-1H-pyrrol-3-acetyl,
- 4-(4-chlorophenyl)-2-phenyl-5-thiazole-acetyl, 10-methyl-10H-phenothiazine-2-acetyl,
- 7-methoxy-α,10-dimethyl-10H-phenothiazine-2-acetyl,
- 5-chloro-3-methyl-benzo[b]thiophene-2-acetyl or —OC—D—E;

D is a single bond between E and the carbon atom of the carbonyl group

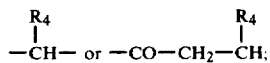

$R_4$ is hydrogen, methyl or ethyl;
E is

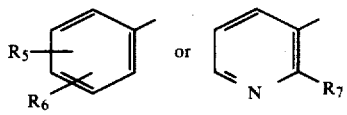

$R_5$ is hydrogen, fluorine, chlorine, bromine or hydroxyl;

$R_6$ is phenyl, phenoxy or phenylamino, each optionally mono-, di- or trisubstituted by methyl, trifluoromethyl, fluorine, chlorine and/or bromine; 2-methylpropyl; cyclohexyl; acetoxy; benzoyl; 2-thienylcarbonyl; 2,5-dihydro-1H-pyrrol-1-yl; or 1,3-dihydro-1-oxo-2H-isoindol-2-yl; and $R_7$ is mono- or disubstituted phenylamino, where the substituents are methyl, trifluoromethyl, fluorine, chlorine or bromine;

and non-toxic, pharmacologically acceptable acid addition salts thereof.

Specific examples of embodiments of substituted phenyl, phenoxy and phenoxyamino groups included in the definition of $R_6$ and $R_7$ are the following:

$R_6$: 2-Fluorophenyl, 4-fluorophenyl, 2,4-difluorophenyl, 2,4-dichlorophenoxy, 3-trifluoromethylphenyl, 2,4-dichlorophenyl-amino, 2,6-dichlorophenyl-amino, 3-chloro-2-methylphenyl-amino, 2,6-dichloro-3-methylphenyl-amino and 2,3-dimethylphenylamino.

$R_7$: 3-Trifluoromethylphenyl-amino, 2-methyl-3-trifluoromethylphenyl-amino and 3-chloro-2-methylphenyl-amino.

Thus, specific examples of antiphlogistic carboxylic acids whose acyl residues are represented by B are the following:

1-(4-chlorobenzoyl)-5-methoxy-2-methyl-1H-indole-3-acetic acid,
(+)-6-methoxy-α-methyl-2-naphthaline acetic acid,
2-[(2,6-dichlorophenyl)-amino]phenyl acetic acid,
3-benzoyl-α-methyl-phenyl-acetic acid,
α-methyl-4-(2-methylpropyl)-phenyl-acetic acid,
2-fluoro-α-methyl-[1,1'-biphenyl]-4-acetic acid,
4-(1,3-dihydro-1-oxo-2H-isoindole-2-yl)-α-methyl-phenyl-acetic acid,
acetylsalicylic acid,
2-[(2,6-dichloro-3-methylphenyl)-amino] benzoic acid,
2-[(3-chloro-2-methylphenyl)-amino] benzoic acid,
5-benzoyl-α-methyl-2-thiophene-acetic acid,
1-methyl-5-(4-methylbenzoyl)-1H-pyrrole-2-acetic acid,
5-fluoro-2-methyl-1-{[4-(methylsulfinyl)-phenyl]methylene}-1H-indene-3-acetic acid,
6,11-dihydro-11-oxo-dibenz[b,e]oxepine-3-acetic acid,
6,11-dihydro-11-oxo-dibenz[b,e]oxepine-2-acetic acid,
α-methyl-5-oxo-5H-dibenzo[a,d] cycloheptene-2-acetic acid,
2-(4-chlorophenyl)-α-methyl-5-benzoxazoleacetic acid,
6-chloro-α-methyl-9H-carbazole-2-acetic acid,
α-ethyl-4-(2-methylpropyl)-phenyl-acetic acid,
α-methyl-3-phenoxy-phenyl-acetic acid,
2-(2,4-dichlorophenoxy)-phenyl-acetic acid,
γ-oxo-[1,1'-biphenyl]-4-butanoic acid,
2',4'-difluoro-4-hydroxy-[1,1'-biphenyl]-3-carboxylic acid,
1,3,4,9-tetrahydro-1-propyl-pyrano[3,4-b]indole-1-acetic acid,
1,8-diethyl-1,3,4,9-tetrahydro-pyrano[3,4-b]indole-1-acetic acid,
2-{[4,5-bis-(4-chlorophenyl)-2-oxazolyl]thio}-propanoic acid,
2-{[3-(trifluoromethyl)-phenyl]amino}benzoic acid,
1-(4-chlorophenyl)-2,5-dimethyl-1H-pyrrol-3-acetic acid,
3-chloro-α-methyl-4-(2-thienylcarbonyl)-phenylacetic acid,
2-[(3-chloro-2-methylphenyl)-amino]-3-pyridinecarboxylic acid,
2-{[2-methyl-3-(trifluoromethyl)-phenyl]amino}-3-pyridine-carboxylic acid,
4-(4-chlorophenyl)-2-phenyl-5-thiazole-acetic acid,
3-chloro-4-(2,5-dihydro-1H-pyrrol-1-yl)-α-methyl-phenyl-acetic acid,
10-methyl-10H-phenothiazine-2-acetic acid,
7-methoxy-α,10-dimethyl-10H-phenothiazine-2-acetic acid,
5-chloro-3-methyl-benzo[b]thiophene-2-acetic acid,
α-methyl-4-(2-thienylcarbonyl)-phenyl-acetic acid,
3-chloro-4-cyclohexyl-γ-oxo-phenyl-butanoic acid,
2-[(2,3-dimethylphenyl)-amino]benzoic acid and
2-{[3-(trifluoromethyl)-phenyl]amino}-3-pyridinecarboxylic acid.

The present invention particularly relates to novel benzoyl derivatives of the formula I, wherein B is —CO—D—E, where D and E have the meanings previously defined, to their non-toxic, pharmacologically acceptable acid addition salts formed with inorganic or organic acids, to processes for their preparation, as well as to the use of the new benzoyl derivatives and their salts as antiinflammatories.

Specific embodiments of $R_1$, $R_2$, $R_3$, A, D and E are the following:

$R_1$: Hydrogen, fluorine, chlorine or bromine.

amino, methylamino, ethylamino, n-propylamino, isopropylamino, n-butylamino, tert. butylamino, n-pentylamino, n-hexylamino, dimethylamino, diethylamino, di-n-propylamino, diisopropylamino, di-n-butylamino, di-n-pentylamino, di-n-hexylamino, N-ethylmethylamino, N-methylpropylamino, N-ethylpropylamino, N-ethylbutylamino, N-propylisopropylamino, N-propylbutylamino, N-methylcyclopentylamino, N-methyl-cyclohexylamino, N-methyl-cycloheptylamino, N-ethyl-cyclopentylamino, N-ethyl-cyclohexylamino, N-ethylcycloheptylamino, N-propyl-cyclopentylamino, N-propyl-cyclohexylamino, N-propyl-cycloheptylamino, cyclopentylamino, cyclohexylamino, cycloheptylamino, dicyclohexylamino, benzylamino, N-methyl-benzylamino, N-ethyl-benzylamino, N-cyclohexyl-benzylamino, dibenzylamino, phenethylamino, N-methyl-phenethylamino, N-propyl-phenethylamino, N-phenylpropylamino, phenylamino, N-methyl-phenylamino, N-ethylphenylamino, 2-(dimethylamino) ethyl-amino, 2-(diethylamino) ethyl-amino, 2-(dipropylamino) ethyl-amino, 3-(dimethylamino) propyl-amino, 3-(dipropylamino) propyl-amino, N-methyl-2-(dimethylamino)ethyl-amino, N-ethyl-2-(diethylamino)ethyl-amino, pyridylamino, pyrrolidino, piperidino, hexamethyleneimino, morpholino, N-methyl-piperazino, N-ethyl-piperazino, N-propyl-piperazino, N-isopropyl-piperazino or N-phenylpiperazino.

A: 1,2-Cyclopentylene, 1,3-cyclopentylene, 1,2-cyclohexylene, 1,3-cyclohexylene, 1,4-cyclohexylene, 1,2-cycloheptylene, 1,3-cycloheptylene, 1,4-cycloheptylene, ethylene, n-propylene, n-butylene, n-pentylene, n-hexylene, n-heptylene, n-octylene, n-nonylene, n-decylene, 1-methyl-ethylene, 2-methyl-ethylene, 1,2-dimethyl-ethylene, 1-methylpropylene, 2-methyl-propylene, 3-methyl-propylene, 1,2-dimethyl-propylene, 1,3-dimethyl-propylene, 2-methyl-2-n-propyl-propylene, 1-methyl-butylene, 1-methyl-pentylene, 1-phenyl-ethylene, 2-phenyl-ethylene, 1,2-diphenyl-ethylene, 1-phenyl-n-propylene, 1-methoxycarbonyl-ethylene, 1-ethoxycarbonyl-ethylene, 2-ethoxycarbonyl-ethylene, 1,2-diethoxycarbonyl-ethylene, 1-ethoxycarbonyl-propylene, 2-ethoxycarbonyl-propylene, 3-ethoxycarbonyl-propylene, 1-propoxycarbonyl-ethylene, 2-propoxycarbonyl-ethylene, 2-hydroxypropylene, 2-hydroxy-butylene, 3-hydroxy-butylene, 2,3-dihydroxy-butylene, 2-hydroxy-pentylene, 2,3,4-trihydroxy-pentylene, 2,3,4,5-tetrahydroxy-n-hexylene, 1-chloromethyl-ethylene, 2-chloromethyl-ethylene, 1-hydroxymethyl-ethylene, 2-hydroxymethyl-ethylene, 2-acetoxymethyl-ethylene, 2-pentanoyloxymethyl-ethylene, 2-decanoyloxymethyl-ethylene, 2-tetradecanoyloxymethyl-ethylene, 2-octadecanoyloxymethyl-ethylene, 2-[4-amino-3-bromo-5-(N-cyclohexylethylaminomethyl)-benzoyloxymethyl]ethylene, 2-acetoxypropylene, 2-pentanoyloxy-propylene, 2-decanoyloxy-propylene, 2-tetradecanoyloxy-propylene, 2-octadecanoyloxy-propylene, diethylene oxide, diethylene sulfide, diethylene sulfoxide, diethylene sulfonyl, N,N-diethylene amino, N,N-diethylene-methylamino, N,N-diethylene-ethylamino, N,N-diethylene-propylamino, N,N-diethylene-isopropylamino, N,N-diethylene-butylamino, N,N-diethylene-tert.butylamino, N,N-diethylene-hexylamino, N,N-diethylene-phenylamino, N,N-diethylene-benzylamino, N,N-diethylene-phenylpropylamino, ethylene-propylene oxide, N-ethylene-N-propylene-methylamino, N-ethylene-N-butylene-ethylamino, cyclohexane-dimethylene, xylylene, pyridine-dimethylene, N,N'-diethylene-piperazino or N-ethylene-N'-propylene-piperazino.

D: A single bond between the radical E and the carbon atom of the carbonyl group, methylene, ethylidene, propylidene, propylene-1-one, 3-methyl-propylene-1-one or 3-ethyl-propylene-1-one.

E: 1-(4-chloro-benzoyl)-5-methoxy-2-methyl-1H-indole-3-yl, (+)-6-methoxy-naphthaline-2-yl, 2-[(2,6-dichlorophenyl)-amino]phenyl, 2-acetoxy-phenyl, 3-benzoyl-phenyl, 4-(2-methylpropyl)phenyl, 2-fluoro-[1,1'-biphenyl]-4-yl, 4-(1,3-dihydro-1-oxo-2H-isoindol-2-yl)-phenyl, 2-[(2,6-dichloro-3-methylphenyl)-amino]phenyl, 2-[(3-chloro-2-methylphenyl)-amino]phenyl, 5-benzoyl-2-thienyl, 1-methyl-5-(4-methylbenzoyl)-1H-pyrrol-2-yl, 5-fluoro-2-methyl-1-{[4-(methylsulfinyl)-phenyl]methylene}-1H-inden-3-yl, 6,11-dihydro-11-oxo-dibenz[b,e]oxepin-3-yl, 6,11-dihydro-11-oxo-dibenz[b,e]oxepin-2-yl, 5-oxo-5H-dibenzo[a,d]cyclohepten-2-yl, 2-(4-chlorophenyl)-benzoxazol-5-yl, 6-chloro-9H-carbazol-2-yl, 3-phenoxyphenyl, 2-(2,4-dichlorophenoxy)-phenyl, [1,1'-biphenyl]-4-yl, 2',4'-difluoro-4-hydroxy-[1,1'-biphenyl]-3-yl, 1,3,4,9-tetrahydro-1-propyl-pyrano[3,4-b]indol-1-yl, 1,8-diethyl-1,3,4,9-tetrahydropyrano[3,4-b]indol-1-yl, [4,5-bis-(4-chlorophenyl)-2-oxazolyl]thio, 2-{[3-(trifluoromethyl)-phenyl]amino}phenyl, 1-(4-chlorophenyl)-2,5-dimethyl-1H-pyrrol-3-yl, 3-chloro-4-(2-thienylcarbonyl)-phenyl, 2-[(3-chloro-2-methylphenyl)-amino]pyrid-3-yl, 2-{[2-methyl-3-(trifluoromethyl)-phenyl]amino}pyrid-3-yl, 4-(4-chlorophenyl)-2-phenyl-thiazol-5-yl, 3-chloro-4-(2,5-dihydro-1H-pyrrol-1-yl)-phenyl, 10-methyl-10H-phenothiazin-2-yl, 7-methoxy-10-methyl-10H-phenothiazin-2-yl, 5-chloro-3-methyl-benzo[b]thiophen-2-yl, 4-(2-thienylcarbonyl)-phenyl, 3-chloro-4-cyclohexyl-phenyl, 2-{[3-(trifluoromethyl)-phenyl]amino}pyrid-3-yl or 2-[(2,3-dimethyl-phenyl)-amino]phenyl group.

A preferred sub-genus is constituted by those compounds of the formula I wherein
each X, which may be identical to or different from the other X, is oxygen or imino;
$R_1$ is hydrogen, chlorine or bromine;
$R_2$ and $R_3$ are each hydrogen, alkyl of 1 to 4 carbon atoms, cycloalkyl of 5 to 7 carbon atoms, benzyl or 2-diethylamino-ethyl;
$R_2$ and $R_3$, together with each other and the nitrogen atom to which they are attached, are pyrrolidino, piperidino, hexamethyleneimino, morpholino, N-methyl-piperazino or N-phenyl-piperazino;

A is straight alkylene of 2 to 10 carbon atoms; substituted ethylene, where the substituents are one to two methyls, one to two alkoxycarbonyls of 2 to 3 carbon atoms each, one to two phenyls, one hydroxyl, one chloromethyl, one hydroxymethyl, one 4-amino-3-bromo-5-(N-ethyl-cyclohexylaminomethyl)-benzoyloxymethyl or one alkanoyloxymethyl of 1 to 18 carbon atoms in the alkanoyl moiety; 2-substituted propylene, where the substituents are one hydroxyl, one alkanoyloxy of 1 to 18 carbon atoms, or two alkyls of 1 to 3 carbon atoms each; tetrahydroxy-n-hexylene; cyclohexylene; straight alkylene of 4 to 6 carbon atoms which is interrupted between the 2- and 3-carbon atoms or the 3- and 4-carbon atoms by oxygen, sulfur, sulfoxide, sulfonyl, amino, phenylamino, benzylamino, piperazino or alkylamino of 1 to 4 carbon atoms in the alkyl moiety; 1,4-cyclohexane-dimethylene; p-xylylene; or 2,6-pyridine-dimethylene; and B is 2-acetoxybenzoyl 2-[(2,6-dichlorophenylamino]-phenyl-acetyl, 1-(4-chlorobenzoyl)-5-methoxy-2-methyl-1H-indole-3-acetyl, 3-benzoyl-α-methyl-phenyl-acetyl, α-methyl-4-(2-methylpropyl)-phenyl-acetyl, 2-fluoro-α-methyl[1,1'-biphenyl]-4-acetyl or (+)-6-methoxy-α-methyl-2-naphthaline-acetyl;
and non-toxic, pharmacologically acceptable acid addition salts thereof.

An especially preferred sub-genus is constituted by those compounds of the formula I wherein
X is oxygen;
$R_1$ is bromine;
$R_2$ is methyl or ethyl;
$R_3$ is ethyl or cyclohexyl;
$R_2$ and $R_3$, together with each other and the nitrogen atom to which they are attached, hexamethyleneimino;

A is straight alkylene of 2 to 6 carbon atoms; or straight alkylene of 4 to 6 carbon atoms which is interrupted between the 2- and 3-carbon atoms or between the 3- and 4-carbon atoms by oxygen, sulfur, ethylamino or propylamino; and B is 1-(4-chlorobenzoyl)-5-methoxy-2-methyl-1H-indole-3-acetyl, 2-[(2,6-dichlorophenyl)amino]phenyl-acetyl, 3-benzoyl-α-methyl-phenyl-acetyl, (+)-6-methoxy-α-methyl-2-naphthaline-acetyl, α-methyl-4-(2-methylpropyl)-phenyl-acetyl or 2-fluoro-α-methyl-[1,1'-biphenyl]-4-acetyl;
and non-toxic, pharmacologically acceptable acid addition salts thereof.

The compounds embraced by formula I may be prepared by the following methods.

Method A

By reacting a carboxylic acid of the formula

B—OH  (II)

wherein B has the same meanings as in formula I, or a salt or reactive derivative thereof with a compound of the formula

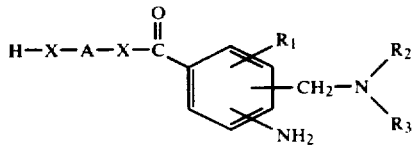

(III)

wherein X, A, R₁, R₂ and R₃ have the same meanings as in formula I, or an alkali metal salt or reactive derivative thereof.

Method B

By reacting a carboxylic acid of the formula

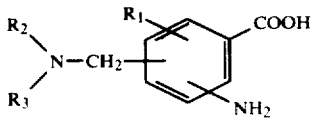

(IV)

wherein R₁, R₂ and R₃ have the same meanings as in formula I, or a salt or reactive derivative thereof, with a compound of the formula

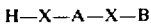

(V)

wherein R₁, R₂, R₃, A, B and X have the same meanings as in formula I or the group HX-, together with the α-carbon and β-carbon atoms of the radical A to which it is attached, may also be oxiranyl, or an alkali metal salt or reactive derivative thereof.

Thus, in these methods the reaction involves the acylation of a compound of the formula III or V with a carboxylic acid of the formula II or IV, respectively, or with a functional derivative thereof, optionally in the presence of an acid-activating and/or dehydrating agent; the reaction of a carboxylic acid of the formula II or IV with a reactive derivative of a compound of the formula III or V, respectively, or the alkylation of a salt of a carboxylic acid of the formula II or IV with a corresponding functional derivative of a compound of the formula III or V, respectively.

Functional derivatives of carboxylic acids of the formula II or IV may include, for example, their alkyl, aryl or aralkyl esters such as the methyl, ethyl, phenyl or benzyl ester, their imidazolides; their acid halides such as the acid chloride or acid bromide; their anhydrides; their mixed anhydrides with aliphatic or aromatic carboxylic acids or carbonic esters, such as the acetic acid, propionic acid or the ethyl carbonates; their acyloxy-triphenyl phosphonium salts; their N-acyloxyimides; or, if the amino group is present in 2-position of a corresponding carboxylic acid of the formula IV, also their isatoic acid anhydrides. Examples of reactive derivatives of a compound of the formula III or V include their phosphazo derivatives if X represents an imino group, and, if X represents an oxygen atom, their epoxides; halides such as the chloride, bromide or iodide; their esters of sulfonic acids such as that of methane sulfonic acid or p-toluene sulfonic acid; or their esters with an aliphatic or aromatic carboxylic acid such as that of acetic acid, propionic acid or benzoic acid. Examples of a carboxylic acid of the formula II or IV are alkali metal and alkaline earth metal salts such as the sodium, potassium or calcium salts, or their silver salt.

Dehydrating and/or acid-activating agents include, for example, esters of chloroformic acid such as ethyl chloroformate, thionyl chloride, phosphorus trichloride, phosphorus pentoxide, N,N'-dicyclohexyl-carbodiimide, N,N'-carbonyldiimidazole, N,N'-thionldiimidazole or borontrifluoride etherate.

The reaction is advantageously carried out in a solvent such as dichloromethane, chloroform, carbon tetrachloride, ether, dioxane, tetrahydrofuran, benzene, toluene, dimethylformamide or methanol, optionally in the presence of an inorganic base such as sodium carbonate or a tertiary organic base such as triethylamine, pyridine and/or 4-dimethylamino-pyridine, which may simultaneously serve also as solvents, optionally in the presence of an acid-activating agent at temperatures between −25° and 250° C., preferably however at temperatures between −10° C. and the boiling point of the solvent which is used. A functional derivative of a compound of the formulas II of V, optionally formed in situ, does not need to be isolated. Furthermore, the reaction can also be carried out without a solvent and/or in the presence of a reaction accelerator such as sodium hydride or 4-dimethyl-aminopyridine. Moreover, the water formed during the reaction can be separated by azeotropic distillation, for instance by heating with toluene in a water separator, optionally in the presence of a drying agent such as magnesium sulfate or a molecular sieve.

However, the reaction of an alkali metal salt of a carboxylic acid of the formula II or IV with a compound of the formula III or V wherein HX is a halogen atom such as chlorine or bromin, can be especially advantageously carried out in the presence of a reaction accelerator such as an alkali metal iodide, for instance sodium or potassium iodide, or in the presence of a phase transfer catalyst such as a so-called crown-ether, for instance 15-crown-5.

The compounds of the formula I wherein A contains a hydroxyl substituent may subsequently be converted by means of acylation into the corresponding acyloxy compounds of the formula I;

the compounds of the formula I wherein A is alkylene interrupted by a sulfur atom, can be converted by means of oxidation into the corresponding sulfoxide of sulfonyl compounds of the formula I; and the compounds of the formula I wherein A is alkylene interrupted by sulfoxide, can be converted by means of oxidation into the corresponding sulfonyl compounds.

The subsequent acylation is advantageously carried out in a solvent such as dimethyl formamide, tetrahydrofuran, toluene or methylene chloride with a corresponding carboxylic acid or reactive derivatives thereof, such as anhydrides, acid halides, 1-imidazolyl derivatives or with mixed anhydrides with carboxylic acids or carbonic acid esters, optionally in the presence of an acid-activating and/or dehydrating agent, such as ethyl chloroformate, thionyl chloride, N,N'-dicyclhexyl-carbodiimide or N,N'-carbonyl-diimidazole, and optionally in the presence of an inorganic base such as sodium carbonate or a tertiary organic base such as triethylamine or pyridine, which may simultaneously serve as a solvent, at temperatures between −25° and 250° C., preferably at temperatures between −10° C. and the boiling point of the solvent which is used.

The subsequent oxidation is preferably carried out in a solvent, such as water, water/pyridine, glacial acetic acid or methanol, and, depending on the particular oxidizing agent which is used, at temperatures between −80° and 100° C.

For the preparation of the sulfoxides of the formula I, the subsequent oxidation is carried out with one equivalent of the particular oxidizing agent, for example with hydrogen peroxide in glacial acetic acid at 0° to 20° C.; with a peracid such as peracetic acid, m-chloroperbenzoic acid or peroxytrifluoro acetic acid at 0° to 50° C.; with sodium metaperiodate in aqueous methanol or ethanol at 15° to 25° C.; with tert. butylhypochlorite in methanol at −80° to −30° C.; with iodobenzene dichloride in aqueous pyridine at 0° to 50° C.; with nitric acid in glacial acetic acid at 0° to 20° C.; with chromic acid in glacial acetic acid or in acetone at 0° to 20° C.; or with sulfuryl chloride in methylene chloride at −70° C., where the resulting thioether-chloro-complex is hydrolyzed in aqueous methanol.

For the preparation of the sulfones of the formula I, the subsequent oxidation is carried out with 1 to 2 equivalents of the particular oxidizing agent, for instance with hydrogen peroxide in glacial acetic acid at 20° to 100° C.; with a peracid such as peracetic acid, m-chloroperbenzoic acid or peroxytrifluoro acetic acid at temperatures between 0° and 50° C.; with nitric acid in glacial acetic acid at 0° to 20° C.; or with chromic acid or potassium permanganate in glacial acetic acid, water/sulfuric acid or in acetone at 0° to 20° C.

The compounds embraced by formula I are basic and therefore form acid addition salts with one to three equivalents of an inorganic or organic acid. Examples of non-toxic, pharmacologically acceptable acid addition salts are those formed with hydrochloric acid, hydrobromic acid, sulfuric acid, phosphoric acid, lactic cid, citric acid, tartaric acid, maleic acid, fumaric acid or the like.

The starting compounds of the formulas II to V used are either known from the literature or can be prepared according to known methods. Thus, for example the benzoic acids of the formula IV and their preparation are described in British Pat. Nos. 1,469,187; the compounds of the formulas III and V are obtained by esterification or amidation of the corresponding carboxylic acids with the corresponding compounds.

The following examples illustrate the present invention and will enable others skilled in the art to understand it more completely. It should be understood, however, that the invention is not limited solely to the particular examples given below.

PREPARATION OF STARTING COMPOUNDS

Example A

1-[4-Amino-3-bromo-5-(N-ethyl-cyclohexylaminomethyl)benzoyloxy]-2,3-dihydroxy-n-propane 70 gm (0.185 mol) of sodium 4-amino-3-bromo-5-(N-ethyl-cyclohexylaminomethyl)-benzoate were suspended in 250 ml of 1-chloro-2,3-dihydroxy-n-propane, and the suspension was heated to 110°-120° C. for 3 hours while stirring. Subsequently, the major amount of the excess 1-chloro-2,3-dihydroxy-n-propane was distilled off at a pressure of 0.02 mm Hg. The residue was dissolved in a mixture of methylene chloride:methanol:-conc. ammonia (90:10:1) and chromatographed on silicagel. The obtained viscous oil was dissolved in 130 ml of isopropanol, and after dilution with 200 ml of ethyl acetate it was converted into the hydrochloride with ethereal hydrochloric acid. After standing for 24 hours at 0°-5° C., the obtained crystals were suction-filtered off, washed with a little ether and dried.

M.p. of the hydrochloride: 167°-173° C.

Example B

1-[4-Amino-3-bromo-5-(N-ethyl-cyclohexylaminomethyl)benzoyloxy]-2-hydroxy-ethane 41 gm (0.1 mol) of 4-amino-3-bromo-5-(N-ethylcyclohexylaminomethyl)-benzoyl chloride hydrochloride were dissolved in 250 ml of ethylene glycol, and after addition of 17 gm (0.22 mol) of pyridine the solution was heated to 105° C. for one hour. After cooling to room temperature, the mixture was diluted with 1 liter of water. After addition of aqueous sodium hydroxide the mixture was extracted with ether, the ether extract was dried over sodium sulfate and evaporated to dryness. The residue was chromatographed on silicagel (eluant: ethyl acetate). After evaporation of the eluate, a resin was obtained which was converted into crystals by trituration with petroleum ether. The crystals obtained were recrystallized from ethanol.

M.p. 72°–75° C.

Example C

1-[4-Amino-3-bromo-5-(N-ethyl-cyclohexylaminomethyl)benzamido]-3-hydroxy-n-propane 30 gm (0.073 mol) of 4-amino-3-bromo-5-(N-ethylcyclohexylaminomethyl)-benzoyl chloride hydrochloride were dissolved in 400 ml of tetrahydrofuran, and the solution was slowly added dropwise to a solution of 15 gm (0.2 mol) of 3-amino-n-propanol in 300 ml of tetrahydrofuran. The mixture was stirred for 30 minutes at 50° C. and then evaporated in vacuo. The residue was taken up in a mixture of water and chloroform, and the chloroform phase was separated, dried and evaporated. The residue was dissolved in isopropanol, and the solution was acidified with ethanolic hydrochloric acid and diluted with ether. The hydrochloride was suction-filtered off and dried.

M.p. of the hydrochloride: 110°–113° C.

Example D

1-[4-Amino-3-bromo-5-(N-ethyl-cyclohexylaminomethyl)benzamido]-4-hydroxy-n-butane 27.5 gm (0.067 mol) of 4-amino-3-bromo-5-(N-ethyl-cyclohexyl-aminomethyl)-benzoyl chloride hydrochloride were dissolved in 400 ml of tetrahydrofuran, and the solution was slowly added dropwise to a solution of 12 gm (0.135 mol) of 4-aminobutanol. The mixture was stirred for 30 minutes at 50° C., and evaporated in vacuo. The residue was taken up in a mixture of water and chloroform, and the chloroform phase was separated, dried and evaporated. The residue was purified by chromatography on silicagel [chloroform:methanol (9:1)]. After evaporating the eluate, an oil was obtained.

IR-spectrum (methylene chloride): amide-CO 1650 $cm^{-1}$

UV-spectrum (ethanol): $\lambda$max 285 nm.

Example E

1-[4-Amino-3-bromo-5-(N-ethyl-cyclohexylaminomethyl)benzoyloxy]-2,3-dihydroxy-n-propane 2.1 gm (0.05 mol) of 1-[4-amino-3-bromo-(N-ethyl-cyclohexyl-aminomethyl)-benzoyloxy]-2,3-epoxy-n-propane were dissolved in a mixture of 100 ml of water and 100 ml of methanol. The resulting solution was adjusted to pH 2–3 with sulfuric acid, and after addition of about 20 mgm of iron(III)-chloride, the mixture was refluxed for 2 hours. After cooling, the mixture was neutralized, evaporated to dryness in vacuo, and the residue was purified by chromatography on silicagel [methylene chloride:methanol:conc.ammonia (90:10:1)]. The obtained oil was dissolved in isopropanol, and the hydrochloride was caused to crystallize out by addition of ethereal hydrochloric acid and ethyl acetate.

M.p. of the hydrochloride: 167°–173° C.

Example F 1-(4-Amino-3-bromo-5-diethylaminomethyl-benzoyloxy)-6-chloro-n-hexane 5.2 gm (0.013 mol) of 1-(4-amino-3-bromo-5-diethylaminomethyl-benzoyloxy)-6-hydroxy-n-hexane were dissolved in 15 ml of chloroform, and the solution was stirred with 15 ml of thionyl chloride for 3 hours at 60° C. The reaction mixture was then evaporated, and the residue was taken up in chloroform. The organic phase was washed with an aqueous sodium bicarbonate solution, dried and evaporated. The residue obtained was dissolved in isopropanol, and the hydrochloride was precipitated with ethereal hydrochloric acid.

M.p. of the hydrochloride: 121°–122° C.

Example G

N-[4-Amino-3-bromo-5-(N-ethyl-cyclohexylaminomethyl)benzoyl]-L-serine methyl ester A solution of 27.4 gm (0.07 mol) of 4-amino-3-bromo-5-(N-ethyl-cyclohexylaminomethyl)-benzoic acid hydrochloride in 250 ml of dimethylformamide was admixed in small portions with 13 gm (0.01 mole) of N,N'-carbonyldiimidazole while stirring at room temperature. The resulting mixture was heated to 50° C. and kept at this temperature for 1 hour. After cooling to room temperature, a solution of 12.5 gm (0.08 mol) of L-serine methyl ester hydrochloride and 8.1 gm (0.08 mol) of triethylamine in 100 ml of dimethylformamide was added while stirring, and the mixture was stirred for 16 hours more. Subsequently, the solvent was removed in vacuo, and the residue was taken up in a mixture of water and chloroform. The chloroform phase was separated, washed with water, dried over sodium sulfate and evaporated in vacuo. A light yellow oil was obtained, which was chromatographed on silicagel (500 gm of silicagel, chloroform:ethyl acetate=3:1). A colorless foam was obtained.

IR-spectrum (methylene chloride):
OH: 3600 cm$^{-1}$
NH$_2$: 3440 cm$^{-1}$
Ester-CO: 1745 cm$^{-1}$
Amido-CO: 1675 cm$^{-1}$ UV-spectrum (ethanol: λmax 230 nm (shoulder), 290 nm.

Example H

1-[4-Amino-3-bromo-5-(N-ethyl-cyclohexylaminomethyl)benzoyl]-D-mannitol 8.25 gm (8.9 mmols) of 1,6-bis-[4-amino-3-bromo-5-(N-ethylcyclohexylaminomethyl)-benzoyl]-D-mannitol dihydrochloride were dissolved in 250 ml of tetrahydrofuran and 100 ml of water. A solution of 13.5 ml of 2 N sodium hydroxide in 100 ml of tetrahydrofuran was added dropwise, while stirring at room temperature. The reaction solution was stirred for 2.5 hours at room temperature. After thin-layer chromatographic evaluation, the solution was admixed with 300 ml of ether, and after brief shaking the phases which had formed were separated. Subsequently, the organic phase was extracted with 2 N-hydrochloric acid, and the aqueous hydrochloric acid extracts were made alkaline with concentrated ammonia and extracted with ether. The ether extracts were washed with water, dried over magnesium sulfate and evaporated in vacuo. After subsequent chromatography of the evaporation residue on silicagel (chloroform:methanol:conc. ammonia=9:1:0.1), the obtained fractions were evaporated in vacuo to dryness. The evaporation residue was dissolved in 150 ml of ethyl acetate, and the calculated amount of ethereal hydrochloric acid was added to the solution. The obtained hydrochloride was recrystallized from methanol/ethyl acetate after suction filtration.

M.p. of the hydrochloride: 153°–160° C. (decomp.).

Example I

1-[4-Amino-3-bromo-5-(N-ethyl-cyclohexylaminomethyl)benzoyloxy]-2,3-dihydroxy-n-propane 9.8 gm (0.025 mol) of 4-amino-3-bromo-5-(N-ethylcyclohexylaminomethyl)-benzoic acid hydrochoride were suspended in 10 gm (0.135 mol) of 2,3-epoxy-n-propanol, and the suspension was heated for 3 hours to 60° C. after addition of 250 mgm of iron(III)-chloride. The reaction mixture was then taken up in a mixture of water and chloroform, and the chloroform phase was separated, dried and evaporated to dryness. The residue was purified by chromatography on silicagel (methylene chloride:methanol:conc.ammonia=90:10:1). The eluate was evaporated, the residue was dissolved in isopropanol, and the hydrochloride was crystallized out by addition of ethanolic hydrochloric acid/ethyl acetate.

M.p. of the hydrochloride: 167°–173° C.

Using procedures analogous to those described in Examples A-I, the following compounds were also prepared:

1-[4-Amino-3-bromo-5-N-ethyl-cyclohexylaminomethyl)-benzoyloxy]-2-chloro-ethane
M.p. of the hydrochloride: 162°–164° C.

1-[4-Amino-3-bromo-5-(N-cyclohexyl-n-propylaminomethyl)-benzoyloxy]-5-hydroxy-n-pentane
M.p. of the hydrochloride: 140°–142° C.

1-[4-Amino-3-bromo-5-(N-ethyl-cyclohexylaminomethyl)-benzoyloxy]-3-chloro-n-propane
M.p. of the hydrochloride: 185°–197° C.

1-[4-Amino-3-bromo-5-(N-ethyl-cyclohexylaminomethyl)-benzoyloxy]-4-chloro-n-butane
M.p. of the hydrochloride: 158°–160° C.

1-[4-Amino-3-bromo-5-(N-ethyl-cyclohexylaminomethyl)-benzoyloxy]-5-chloro-n-pentane
M.p. of the hydrochloride: 141°–142.5° C.

1-[4-Amino-3-bromo-5-(N-ethyl-cyclohexylaminomethyl)-benzoyloxy]-7-chloro-n-heptane
M.p. of the hydrochloride: 129°–131° C.

1-[4-Amino-3-bromo-5-(N-ethyl-cyclohexylaminomethyl)-benzoyloxy]-8-chloro-n-octane
M.p. of the hydrochloride: 114°–117° C.

1-[4-Amino-3-bromo-5-(N-ethyl-cyclohexylaminomethyl)-benzoyloxy]-3-hydroxy-n-propane
M.p. of the hydrochloride: 184°–185° C.

1-[4-Amino-3-bromo-5-(N-ethyl-cyclohexylaminomethyl)-benzoyloxy]-4-hydroxy-n-butane
M.p. of the hydrochloride: 148°–150° C.

1-[4-Amino-3-bromo-5-(N-ethyl-cyclohexylaminomethyl)-benzoyloxy]-5-hydroxy-n-pentane
M.p. of the hydrochloride: 158°–160° C.

1-[4-Amino-3-bromo-5-(N-ethyl-cyclohex-ylaminomethyl)-benzoyloxy]-6-hydroxy-n-hexane
M.p. of the hydrochloride: 98°-101° C.

1-[4-Amino-3-bromo-5-(N-ethyl-cyclohex-ylaminomethyl)-benzoyloxy]-7-hydroxy-n-heptane
M.p. of the hydrochloride: 102°-104° C. (decomp.).

1-[4-Amino-3-bromo-5-(N-ethyl-cyclohex-ylaminomethyl)-benzoyloxy]-8-hydroxy-n-octane
M.p. of the hydrochloride: 99°-103° C.

1-[4-Amino-3-bromo-5-(N-ethyl-cyclohex-ylaminomethyl)-benzoyloxy]-4-hydroxy-cyclohexane
IR-spectrum (methylene chloride): ester-CO 1700 cm$^{-1}$
UV-spectrum (ethanol): λmax 230 nm (shoulder), 298-300 nm.

1-[4-Amino-3-bromo-5-(N-ethyl-cyclohex-ylaminomethyl)-benzoyloxy]-2-hydroxy-n-propane
IR-spectrum (methylene chloride): ester-CO 1700 cm$^{-1}$
UV-spectrum (ethanol): λmax 230 nm (shoulder), 297 nm.

2-[4-Amino-3-bromo-5-(N-ethyl-cyclohex-ylaminomethyl)-benzoyloxy]-3-hydroxy-n-butane
IR-spectrum (methylene chloride): Ester-CO: 1705 cm$^{-1}$
UV-spectrum (ethanol): λmax 230 nm (shoulder), 299 nm.

1-[4-Amino-3-bromo-5-(N-ethyl-cyclohep-tylaminomethyl)-benzoyloxy]-5-hydroxy-n-pentane
M.p. of the hydrochloride: 162°-163° C.

2-[4-Amino-3-bromo-5-(N-ethyl-cyclohex-ylaminomethyl)-benzoyl](+)-tartaric acid diethyl ester
$C_{24}H_{35}BrN_2O_7$ (543.5)
Calc.: C-53.04%; H-6.49%; Br-14.70%; N-5.15%
Found: C-53.30%; H-6.59%; Br-14.55%; N-5.12%.

1-[4-Amino-3-bromo-5-(N-ethyl-cyclohex-ylaminomethyl)-benzoyloxy]-2,3-epoxy-n-propane
IR-spectrum (methylene chloride): Ester-CO: 1705 cm$^{-1}$
UV-spectrum (ethanol): λmax 300 nm.

2-[4-Amino-3-bromo-5-(N-ethyl-cyclohex-ylaminomethyl)-benzoyloxy]-2'-hydroxy-diethyloxide
$C_{20}H_{31}BrN_2O_4$ (443.4)
Calc.: C-54.18%; H-7.05%; Br-18.02%; N-6.32%
Found: C-53.90%; H-7.19%; Br-18.25%; N-6.26%.

N-{2-[4-Amino-3-bromo-5-(N-ethyl-cyclohex-ylaminomethyl)-benzoyloxy]-ethyl}-N-(2-hydroxyethyl)-methylamine
Calc.: C-55.26%; H-7.51%; Br-17.51%; N-9.21%
Found: C-55.30%; H-7.62%; Br-17.75%; N-9.06%.

1-{2-[4-Amino-3-bromo-5-(N-ethyl-cyclohex-ylaminomethyl)-benzoyloxy]-ethyl}-4-(2-hydroxyethyl)-piperazine
IR-spectrum (methylene chloride):
  Ester-CO: 1710 cm$^{-1}$
  N-alkyl: 2830 cm$^{-1}$
UV-spectrum (ethanol: λmax 300 nm.

1-{3-[4-Amino-3-bromo-5-(N-ethyl-cyclohex-ylaminomethyl)-benzoyloxy]-propyl}-4-(2-hydroxyethyl)-piperazine
M.p. of the trihydrogen maleate: 144°-146° C. (decomp.).

1,6-Bis-[4-amino-3-bromo-5-(N-ethyl-cyclohex-ylaminomethyl)-benzoyl]-D-mannitol dihydrochloride
IR-spectrum (KBr):
  Ester-CO: 1710 cm$^{-1}$
  N-alkyl: 2840 cm$^{-1}$
UV-spectrum (ethanol): λmax 230 nm, 295 nm.

1-[4-Amino-3-bromo-5-(N-ethyl-cyclohex-ylaminomethyl)-benzoyloxy]-2-hydroxy-3-chloro-n-propane
IR-spectrum (methylene chloride): Ester-CO: 1710 cm$^{-1}$
UV-spectrum (ethanol): λmax 300 nm.

1-[4-Amino-3-bromo-5-(N-ethyl-cyclohex-ylaminomethyl)-benzamido]-2-hydroxy-ethane
M.p. of the hydrochloride: from 65° C. (decomp.).

1-[4-Amino-3-bromo-5-(N-ethyl-cyclohex-ylaminomethyl)-benzamido]-5-hydroxy-n-pentane
IR-spectrum (methylene chloride): Amide-CO: 1650 cm$^{-1}$
UV-spectrum (ethanol): λmax 285 nm.

1-[4-Amino-3-bromo-5-(N-ethyl-cyclohex-ylaminomethyl)-benzamido]-6-hydroxy-n-hexane
IR-spectrum (methylene chloride): Amide-CO: 1650 cm$^{-1}$
UV-spectrum (ethanol): λmax 285 nm.

trans-1-[4-Amino-3-bromo-5-(N-ethyl-cyclohex-ylaminomethyl)-benzamido]-4-hydroxy-cyclohexane
M.p. of the dihydrochloride: 176° C. (decomp.).

N-[4-Amino-3-bromo-5-(N-ethyl-cyclohex-ylaminomethyl)-benzoyl]-D-glucosamine
$C_{22}H_{24}BrN_3O_6$ (516.5)
Calc.: C-51.16%; H-6.64%; Br-15.47%; N-8.14%
Found: C-51.00%; H-6.87%; Br-15.30%; N-8.00%.

1-[4-Amino-3-bromo-5-(N-ethyl-cyclopen-tylaminomethyl)-benzoyloxy]-5-chloro-n-pentane M.p. of the hydrochloride: 131°-133° C.

1-[4-Amino-3-bromo-5-(N-ethyl-cyclohex-ylaminomethyl)-benzamido]-2-amino-ethane
M.p. beginning at 85° C. (decomp.).

1-[4-Amino-3-bromo-5-(2-diethylaminoe-thylaminomethyl)-benzoyloxy]-2-hydroxy-ethane.
M.p. of the dihydrochloride: 87°-90° C. (decomp.).

1-(4-Amino-3-bromo-5-diethylaminomethyl-benzoyloxy)-2-chloro-ethane
M.p. of the hydrochloride: 142°-145° C.

1-(4-Amino-3-bromo-5-diethylaminomethyl-benzoyloxy)-3-chloro-n-propane
M.p. of the hydrochloride: 167°-168° C.

1-(4-Amino-3-bromo-5-diethylaminomethyl-benzoyloxy)-4-chloro-n-butane
M.p. of the hydrochloride: 159°-162° C.

1-(4-Amino-3-bromo-5-diethylaminomethyl-benzoyloxy)-5-chloro-n-pentane
M.p. of the hydrochloride: 117°-119° C.

1-(4-Amino-3-bromo-5-diethylaminomethyl-benzoyloxy)-6-chloro-n-hexane
M.p. of the hydrochloride: 121°-122° C.

1-(4-Amino-3-bromo-5-diethylaminomethyl-benzoyloxy)-2-hydroxy-ethane
M.p. of the hydrochloride: 151°-152° C.

1-(4-Amino-3-bromo-5-diethylaminomethyl-benzoyloxy)-3-hydroxy-n-propane
M.p. of the hydrochloride: 139°-141° C.

1-(4-Amino-3-bromo-5-diethylaminomethyl-benzoyloxy)-4-hydroxy-n-butane
M.p. of the hydrochloride: 163°-165° C.

1-(4-Amino-3-bromo-5-diethylaminomethyl-benzoyloxy)-5-hydroxy-n-pentane
M.p. of the hydrochloride: 137.5°-138.5° C.

1-(4-Amino-3-bromo-5-diethylaminomethyl-benzoyloxy)-2,3-dihydroxy-n-propane
Mass spectrum: M$^+$ 374/6 m/e (monobromo) Calc.: $C_{15}H_{23}BrN_2O_4$ (374/6)

1-(4-Amino-3-bromo-5-diethylaminomethyl-benzoyloxy)-2-hydroxy-3-chloro-n-propane
IR-spectrum (methylene chloride): Ester-CO: 1715 cm$^{-1}$
UV-spectrum (ethanol): λmax 230 nm, 298–300 nm.

1-(4-Amino-3-bromo-5-hexamethyleneiminomethyl-benzoyloxy)-5-chloro-n-pentane
M.p. of the hydrochloride: 160°–162° C.

1-[4-Amino-3-bromo-5-(N-ethyl-cycloheptylaminomethyl)-benzoyloxy]-5-chloro-n-pentane
M.p. of the hydrochloride: 156°–158° C.

1-[4-Amino-3-bromo-5-(N-cyclohexyl-n-propylaminomethyl)-benzoyloxy]-5-chloro-n-pentane
M.p. of the hydrochloride: 145°–147° C.

1-(4-Amino-3-bromo-5-dimethylaminomethyl-benzoyloxy)-2-hydroxy-ethane
M.p. of the hydrochloride: 80°–81° C.

1-(4-Amino-3-bromo-5-isopropylaminomethylbenzoyloxy)-2-hydroxy-ethane
M.p. of the hydrochloride: 90°–93° C.

1-[4-Amino-3-bromo-5-(N-methyl-n-propylaminomethyl)benzoyloxy]-2-hydroxy-ethane
M.p. of the hydrochloride: 124°–128° C.

1-(4-Amino-3-bromo-5-tert. butylaminomethylbenzoyloxy)-2-hydroxy-ethane
M.p. of the hydrochloride: 192°–194° C.

1-(4-Amino-3-bromo-5-cyclohexylaminomethylbenzoyloxy)-2-hydroxy-ethane
M.p. of the dihydrochloride: 149° C. (decomp.).

1-[4-Amino-3-bromo-5-(N-cyclohexyl-methylaminomethyl)-benzoyloxy]-2-hydroxy-ethane
M.p. of the hydrochloride: 169°–171° C.

1-[4-Amino-3-bromo-5-(N-ethyl-cyclopentylaminomethyl)-benzoyloxy]-2-hydroxy-ethane
M.p. of the hydrochloride: 186°–187° C.

1-[4-Amino-3-bromo-5-(N-ethyl-cycloheptylaminomethyl)-benzoyloxy]-2-hydroxy-ethane
M.p. of the hydrochloride: 166°–168° C.

1-[4-Amino-3-bromo-5-(N-cyclohexyl-n-propylaminomethyl)-benzoyloxy]-2-hydroxy-ethane
M.p. of the hydrochloride: 194°–196° C.

1-[4-Amino-3-bromo-5-(4-pyridylaminomethyl)benzoyloxy]-2-hydroxy-ethane
M.p. of the hydrochloride: 217°–218° C.

1-(4-Amino-3-bromo-5-pyrrolidinomethyl-benzoyloxy)-2-hydroxy-ethane
M.p. of the hydrochloride: 213°–214° C.

1-(4-Amino-3-bromo-5-piperidinomethyl-benzoyloxy)-2-hydroxy-ethane
M.p. of the hydrochloride: 214°–216° C.

1-(4-Amino-3-bromo-5-morpholinomethyl-benzoyloxy)-2-hydroxy-ethane
M.p. of the hydrochloride: 179°–181° C.

1-[4-Amino-3-bromo-5-(4-methyl-piperazinomethyl)-benzoyloxy]-2-hydroxy-ethane
M.p. of the dihydrochloride: 163°–165° C.

1-(4-Amino-3-bromo-5-hexamethyleneiminomethyl-benzoyloxy)-2-hydroxy-ethane
M.p. of the hydrochloride: 209° C. (decomp.).

1-[4-Amino-3-bromo-5-(N-ethyl-cyclohexylaminomethyl)-benzoyloxy]-1-phenyl-2-hydroxy-ethane
IR-spectrum (methylene chloride):
OH: 3600 cm$^{-1}$
NH$_2$: 3440 cm$^{-1}$
N-Alkyl: 2930 cm$^{-1}$
Ester-CO: 1710 cm$^{-1}$
UV-spectrum (ethanol): λmax 230 nm, 297 nm.

1-[4-Amino-3-bromo-5-(N-ethyl-cyclohexylaminomethyl)-benzoyloxy]-2-phenyl-2-hydroxy-ethane
IR-spectrum (methylene chloride):
OH: 3600 cm$^{-1}$
NH$_2$: 3450 cm$^{-1}$
N-Alkyl: 2950 cm$^{-1}$
Ester-CO: 1710 cm$^{-1}$
UV-spectrum (ethanol): λmax 293 nm.

1-[4-Amino-3-bromo-5-(N-ethyl-cyclohexylaminomethyl)-benzoyloxy]-1,2-diphenyl-2-hydroxy-ethane
IR-spectrum (methylene chloride):
OH: 3600 cm$^{-1}$
NH$_2$: 3450 cm$^{-1}$
N-Alkyl: 2940 cm$^{-1}$
Ester-CO: 1725 cm$^{-1}$
UV-spectrum (ethanol): λmax 295 nm.

1-[4-Amino-3-bromo-5-(N-ethyl-cyclohexylaminomethyl)-benzoyloxy]-2-hydroxymethyl-2-methyl-pentane
IR-spectrum (methylene chloride):
OH: 3620 cm$^{-1}$
NH$_2$: 3460 cm$^{-1}$
N-Alkyl: 2960 cm$^{-1}$
Ester-CO: 1705 cm$^{-1}$
UV-spectrum (ethanol): λmax 288 nm.

2-[4-Amino-3-bromo-5-(N-ethyl-cyclohexylaminomethyl)-benzoyloxy-methyl]-6-hydroxymethyl-pyridine
IR-spectrum (methylene chloride):
OH: 3610 cm$^{-1}$
NH$_2$: 3440 cm$^{-1}$
N-Alkyl: 2920 cm$^{-1}$
Ester-CO: 1710 cm$^{-1}$
UV-spectrum (ethanol): λmax 230 nm, 298 nm.

1-[4-Amino-3-bromo-5-(N-ethyl-cyclohexylaminomethyl)-benzoyloxy-methyl]-4-hydroxymethyl-benzene
IR-spectrum (methylene chloride):
OH: 3600 cm$^{-1}$
NH$_2$: 3450 cm$^{-1}$
N-Alkyl: 2940 cm$^{-1}$
Ester-CO: 1705 cm$^{-1}$
UV-spectrum (ethanol): λmax 295 nm.

1-[4-Amino-3-bromo-5-(N-ethyl-cyclohexylaminomethyl)-benzoyloxy-methyl]-4-hydroxymethyl-cyclohexane
IR-spectrum (methylene chloride):
OH: 3600 cm$^{-1}$
NH$_2$: 3440 cm$^{-1}$
N-Alkyl: 2910 cm$^{-1}$
Ester-CO: 1695 cm$^{-1}$
UV-spectrum (ethanol): λmax 294 nm.

1-(4-Amino-3-bromo-5-dimethylaminomethylbenzoyloxy)-5-hydroxy-n-pentane
M.p. of the hydrochloride: 155°–157° C.

1-(4-Amino-3-bromo-5-morpholinomethyl-benzoyloxy)-5-hydroxy-n-pentane
M.p. of the hydrochloride: 205°–207° C.

1-(4-Amino-3-bromo-5-piperidinomethyl-benzoyloxy)-5-hydroxy-n-pentane
M.p. of the hydrochloride: 186°–188° C.

1-[4-Amino-3-bromo-5-(4-methyl-piperazinomethyl)-benzoyloxy]-5-hydroxy-n-pentane
M.p. of the hydrochloride: 182°–185° C.

1-[4-Amino-3-bromo-5-(N-cyclohexyl-methylaminomethyl)-benzoyloxy]-5-hydroxy-n-pentane
M.p. of the hydrochloride: 123°–126° C.

1-[4-Amino-3-bromo-5-(4-methylpiperazinomethyl)-benzoyloxy]-4-hydroxy-n-butane
M.p. of the dihydrochloride: 200°–202° C.

1-(4-Amino-3-bromo-5-hexamethyleneiminomethyl)-4-hydroxy-n-butane

M.p. of the hydrochloride: 159°–161° C.

1-[4-Amino-3-bromo-5-(N-cyclohexylmethylaminomethyl)-benzoyloxy]-4-hydroxy-n-butane M.p. of the hydrochloride: 163°–165° C.

1-(4-Amino-3-bromo-5-pyrrolidinomethylbenzoyloxy)-4-hydroxy-n-butane

M.p. of the hydrochloride: 140°–144° C.

1-(4-Amino-3-bromo-5-morpholinomethyl-benzoyloxy)-4-hydroxy-n-butane

M.p. of the hydrochloride: 182°–184° C.

1-(4-Amino-3-bromo-5-piperidinomethyl-benzoyloxy)-4-hydroxy-n-butane

M.p. of the hydrochloride: 170°–172° C.

1-[4-Amino-3-bromo-5-(N-ethyl-cyclohexylaminomethyl)-benzoyloxy]-9-hydroxy-n-nonane M.p. of the hydrochloride: 73°–76° C.

PREPARATION OF END PRODUCTS OF THE FORMULA I:

Example 1

1-[4-Amino-3-bromo-5-(N-ethyl-cyclohexylaminomethyl)benzoyloxy]-2-[1-(4-chlorobenzoyl)-5-methoxy-2-methyl-1H-indole-3-acetoxy]-ethane 25.0 gm (0.0626 mol) of 1-[4-amino-3-bromo-5-(N-ethyl-cyclohexylaminomethyl)-benzoyloxy]-2-hydroxy-ethane and 25.6 gm (0.0626 mol) of 1-(4-chlorobenzoyl)-5-methoxy-2-methyl-1H-indole-acetic acid imidazolide were dissolved in 300 ml of tetrahydrofuran. While stirring, a catalytic amount of a sodium hydride dispersion in oil was added at room temperature. After standing overnight, the tetrahydrofuran was disstilled off in water aspirator vacuum, the residual oil was taken up in chloroform, and the solution was washed twice with water. The chloroform solution was dried over sodium sulfate and evaporated. For further purification, the crude product was chromatographed on a silicagel column with chloroform/methanol (9.5:0.5). The obtained oily base was crystallized as its hydrochloride from a mixture of isopropanol and ethanolic hydrogen chloride (1:1) containing 15% chloroform.

M.p. of the hydrochloride: from 123° C. (decomp.).

Example 2

1-[4-Amino-3-bromo-5-(N-ethyl-cyclohexylaminomethyl)benzoyloxy]-3-(3-benzoyl-α-methyl-phenylacetoxy)-2-hydroxy-n-propane 14.9 gm (0.035 mol) of 1-[4-amino-3-bromo-5-(N-ethyl-cyclohexylaminomethyl)-benzoyloxy]-2,3-dihydroxy-n-propane and 10.6 gm (0.035 mol) of 3-benzoyl-α-methylphenyl-acetic acid imidazolide were dissolved in 250 ml of absolute tetrahydrofuran. While stirring, a catalytic amount of a sodium hydride dispersion in oil was added at room temperature. After stirring for 4 hours and standing overnight, the reaction mixture was filtered, and the filtrate was evaporated in vacuo. The residue was dissolved in chloroform, and the solution was washed with water three times. The chloroform solution was dried over sodium sulfate and evaporated to dryness in vacuo. The obtained crude product was purified by column chromatography on silicagel with toluene/acetone (7:1). The hydrochloride was obtained by dissolving the obtained base in absolute ethanol, adding absolute ethanolic hydrochloric acid until acid reaction, and evaporating to dryness in water aspirator vacuum.

M.p. of the hydrochloride: 82°–94° C.

Example 3

N-{2-[4-Amino-3-bromo-5-(N-ethyl-cyclohexylaminomethyl)benzoyloxy]-ethyl}-N-{2-[1-(4-chlorobenzoyl)-5-methoxy-2-methyl-1H-indole-3-acetoxy]-ethyl}-methylamine To a solution of 6.5 gm (0.02 mol) of 1-(4-chlorobenzoyl)-5-methoxy-2-methyl-1H-indole-3-acetic acid in 150 ml of anhydrous tetrahydrofuran, 3.6 gm (0.022 mol) of carbonyl-diimidazole were added, while stirring at room temperature. After stirring for another hour at room temperature, a solution consisting of 9.1 gm (0.02 mol) of N-{2-[4-amino-3-bromo-5-(N-ethyl-cyclohexylaminomethyl)benzoyloxy]-ethyl}-N-(2-hydroxyethyl)-methylamine in 100 ml of anhydrous tetrahydrofuran was added dropwise at −10° C. After the addition was finished, a small amount of a 40% sodium hydride suspension in oil was added and the reaction mixture was stirred for 12 hours more while slowly increasing the temperature to room temperature. The solvent was then evaporated at 35° C. in vacuo, the evaporation residue was dissolved in 150 ml of ether, and the ethereal solution was washed with water, 2 N ammonia and again with water. After drying the ethereal solution with magnesium sulfate and evaporating it at 30° C. in vacuo, the residue was purified on a silicagel column with methylene chloride/methanol (30:1). The desired fractions were evaporated at 35° C. to dryness in vacuo. After dissolving the evaporation residue in 250 ml of ether and admixing the solution with ethereal hydrochloric acid, the dihydrochloride was isolated as an amorphous precipitate.

M.p. of the dihydrochloride: 179°–184° C. (decomp.).

Example 4

N-{2-[4-Amino-3-bromo-5-(N-ethyl-cyclohexylaminomethyl)benzoyloxy]-ethyl}-N-{2-[2-[(2,6-dichlorophenyl)-amino]phenylacetoxy]-ethyl}-tert. butylamine 10 gm (0.02 mol) of N-{2-[4-amino-3-bromo-5-(N-ethyl-cyclohexylaminomethyl)-benzoyloxy]-ethyl}-N-(2-hydroxyethyl)-tert. butylamine were dissolved in 200 ml of anhydrous tetrahydrofuran, and the solution was admixed at room temperature with a solution of 6.5 gm (0.022 mol) of 2-[(2,6-dichlorophenyl)-amino]-phenyl-acetic acid and 0.3 gm of 4-dimethylaminopyridine in 100 ml of anhydrous tetrahydrofuran. At −10° C. a solution of 4.5 gm (0.022 mol) of dicyclohexyl-carbodiimide in 50 ml of anhydrous tetrahydrofuran was added dropwise to the reaction solution. After stirring for 60 minutes at −10° C. and then for three hours up to a temperature of 0° C., 1.2 gm (0.004 mol) of 2-[(2,6-dichlorophenyl)-amino]-phenyl-acetic acid and 0.85 (0.004 mol) of dicyclohexyl-carbodiimide were again added, and the mixture was stirred for 18 hours more at room temperature. The reaction mixture was then suction-filtered to separate the precipitated dicyclohexylurea, the filtrate was evaporated in vacuo at 35° C., and the residue was purified on a silicagel column with ether/petroleum ether (1:2). After evaporating the desired fractions, the evaporation residue was dissolved in 500 ml of ether. The desired product was obtained as the amorphous dihydrochloride upon adding a calculated amount of ethereal hydrochloric acid.

M.p. of the dihydrochloride: 150°–180° C.

Example 5

1-[4-Amino-3-bromo-5-(N-ethyl-cyclohexylaminomethyl)benzoyloxy]-2-[1-(4-chlorobenzoyl)-5-methoxy-2-methyl-1H-indole-3-acetoxy]-ethane To a solution of 168 gm (0.387 mol) of 1-[4-amino-3-bromo-5-(N-ethyl-cyclohexylaminomethyl)-benzoyloxy]-2-hydroxyethane-hydrochloride and 30.5 gm (0.387 mol) of pyridine in 1500 ml of chloroform, a solution of 150.5 gm (0.4 mol) of 1-(4-chlorobenzoyl)-5-methoxy-2-methyl-1H-indole-3-acetyl chloride in 1000 ml of chloroform was added while stirring at room temperature. After stirring overnight, the reaction solution was washed five times with 2 liters each of water, filtered through activated charcoal, dried over sodium sulfate and evaporated in water aspirator vacuum. The residual oil was dissolved in a mixture of 150 ml of chloroform and 750 ml of isopropanol, and the solution was adjusted to pH 3–4 with ethanolic hydrochloric acid. The product was caused to crystallize out by admixing this solution with 500 ml of ether until turbidity began. The crystals were dissolved in 600 ml of methanol, the solution was admixed with 1200 ml of isopropanol, whereby the substance crystallized again. The crystals were dried at 80° C. in vacuo.

M.p. of the hydrochloride: from 123° C. (decomp.).

Example 6

1-[4-Amino-3-bromo-5-(N-ethyl-cyclohexylaminomethyl)-benzoyloxy]-2-hydroxy-3-[1-(4-chlorobenzoyl)-5-methoxy-2-methyl-1H-indole-3-acetoxy]-n-propane 18.5 gm (0.045 mol) of 1-[4-amino-3-bromo-5-(N-ethyl-cyclohexyl-aminomethyl)-benzoyloxy]-2,3-epoxy-n-propane were dissolved in 250 ml of dry dioxane. To this solution 15.5 gm (0.045 mol) of 1-(4-chlorobenzoyl)-5-methoxy-2-methyl-1H-indole-3-acetic acid and 750 mgm iron(III)-chloride were added. The mixture was refluxed for 24 hours under exclusion of moisture and then evaporated in vacuo. The residue was purified by chromatography on silicagel with chloroform/methanol (40:1). A nearly colorless, amorphous substance was obtained.

UV-spectrum (ethanol): λ max 230 nm, 260 nm
IR-spectrum (methylene chloride):
Amide-CO: 1675 $cm^{-1}$
Ester-Co: 1705 $cm^{-1}$ and 1740 $cm^{-1}$.

Example 7

1-[4-Amino-3-bromo-5-(N-ethyl-cyclohexylaminomethyl)-benzoyloxy]-2-[(+)-6-methoxy-α-methyl-2-naphthalineacetamino]-ethane 12 gm (0.036 mol) of 2-methoxycarbonyl-2-[(+)-6-methoxy-α-methyl-2-naphthaline-acetamino]-ethanol, 17.3 gm (0.041 mol) of 4-amino-3-bromo-5-(N-ethyl-cyclohexylaminomethyl)-benzoyl-chloride hydrochloride, 12.5 ml of triethylamine and 2.2 gm of 4-dimethylamino-pyridine were added to 200 ml of methylene chloride, and the mixture was refluxed for one hour. After cooling to room temperature, the mixture was washed twice with 200 ml each of water. The methylene chloride solution was separated, dried over sodium sulfate and evaporated in vacuo to dryness. The oily residue was purified on a chromatography column (silicagel; benzene/acetone-19:1), and the eluate was evaporated. A colorless foam was obtained.

IR-spectrum (methylene chloride):

$NH_2$: 3510 $cm^{-1}$
N-alkyl: 2930 $cm^{-1}$
$O-CH_3$: 2850 $cm^{-1}$
Ester-CO: 1750 $cm^{-1}$ and 1720 $cm^{-1}$
Amide-CO: 1680 $cm^{-1}$
UV-spectrum (ethanol): λ max 234 nm, 295 nm.

Example 8

1-[4-Amino-3-bromo-5-(N-ethyl-cyclohexylaminomethyl)-benzoyloxy]-5-{2-[(2,6-dichlorophenyl)-amino]-phenylacetoxy}-n-pentane 26.2 gm (0.057 mol) of 5-[4-amino-3-bromo-5-(N-ethyl-cyclohexylaminomethyl)-benzoyloxy]-n-pentyl chloride, 20 gm (0.063 mol) of sodium 2-[(2,6-dichlorophenyl)-amino]phenyl-acetate and 4.2 gm of sodium iodide were dissolved in 280 ml of absolute dimethylformamide, and the solution was kept for 4 hours at 110° C. while occasionally shaking. The dimethylformamide was then distilled off in a water aspirator vacuum, the residue was dissolved in chloroform, and the organic phase was washed with water, dried over sodium sulfate and evaporated in vacuo. The obtained crude product was chromatographed on a silicagel column with cyclohexane/acetone (9:1). After evaporation of the eluate, the obtained base was crystallized as its hydrochloride from isopropanol/ether by acidifying with ethanolic hydrochloric acid.

M.p. of the hydrochloride: 129°–132° C.

Example 9

1-[4-Amino-3-bromo-5-(N-ethyl-cyclohexylaminomethyl)-benzoyloxy]-2-hydroxy-3-[(+)-6-methoxy-α-methyl-2-naphthaline-acetoxy]-n-propane 4.6 gm (0.02 mol) of (+)-6-methoxy-α-methyl-2-naphthaline-acetic acid were dissolved in 30 ml of dimethylformamide and converted into the sodium salt by addition of 875 mgm (0.02 mol) of sodium hydride. 9 gm (0.02 mol) of 3-[4-amino-3-bromo-5-(N-ethyl-cyclohexylaminomethyl)-benzoyloxy]-2-hydroxy-n-propyl chloride in 60 ml of dimethylformamide were added to the solution. After adding 3.5 gm (0.021 mol) of potassium iodide and 1 ml of 15-crown-5, the mixture was heated for 10 hours at about 80° C. Subsequently, the major portion of the dimethylformamide was distilled off in vacuo, and the residue was taken up in a mixture of a solution of 35 gm of ammonium acetate in 400 ml of ice water and chloroform. The organic phase was dried over sodium sulfate and evaporated in vacuo. The residue was purified by chromatography on silicagel with toluene/acetone/ammonia (80:20:0.25). A colorless, viscous oil was obtained.

IR-spectrum (methylene chloride): Ester-CO 1710 $cm^{-1}$ and 1740 $cm^{-1}$.
UV-spectrum (ethanol): λ max 234 nm, 298 nm.
M.p. of the amorphous hydrochloride: from 80° C.

Example 10

1-[1-(4-Chlorobenzoyl)-5-methoxy-2-methyl-1H-indole-3-acetyl]-6-[4-amino-3-bromo-5-(N-ethyl-cyclohexylaminomethyl)-benzoyl]-D-mannitol A solution of 12.3 gm (0.03 mol) of 4-amino-3-bromo-5-(N-ethyl-cyclohexylaminomethyl)-benzoyl chloride hydrochloride in 100 ml of absolute chloroform was added dropwise to a solution of 15.6 gm (0.03 mol) of 1-[1-(4-chlorobenzoyl)-5-methoxy-2-methyl-1H-indole-3-acetyl]-D-mannitol, in 200 ml of absolute pyridine, while stirring and cooling with ice. The reaction solution was stirred for 15 hours at room temperature, whereupon the pyridine was distilled off at 50° C. in vacuo and the evaporation residue was taken up in a mixture of 300 ml of methylene chloride and 300 ml of water. After separating the phases and washing the methylene chloride phase twice with 200 ml of 2 N ammonia each and water, the organic solution was dried over magnesium sulfate and evaporated to dryness at 35° C. in vacuo. For further purification the residue was chromatographed on a silicagel column with chloroform/methanol (30:1) and crystallized from methylene chloride/ether.

M.p.: 97°–112° C. (decomp.).

Example 11

1-Acetoxy-1-[4-amino-3-bromo-5-(N-ethyl-cyclohexylaminomethyl)-benzoyloxy]-3-[(+)-6-methoxy-α-methyl-2-naphthalineacetoxy]n-propane 9 gm (0.025 mol) of 4-amino-3-bromo-5-(N-ethylcyclohexylaminomethyl)-benzoic acid were dissolved in 60 ml of tetrahydrofuran, and the solution was admixed with 4.2 gm (0.026 mol) of carbonyldiimidazole. After 30 minutes a solution of 7 gm (0.021 mol) of 1-acetoxy-2-hydroxy-3-[(+)-6-methoxy-α-methyl-2-naphthalineacetoxy]-n-propane in 60 ml of tetrahydrofuran was added. The mixture was refluxed for 2.5 hours, and after standing overnight at room temperature it was evaporated in vacuo. The residue was taken up in a mixture of water and chloroform, and the organic phase was separated, dried and evaporated. The residue was purified by chromatography on silicagel with chloroform/ethyl acetate (20:1). A colorless, amorphous substance was obtained.

UV-spectrum (ethanol): λ max 243 nm, 300 nm
IR-spectrum (methylene chloride): Ester-CO 1710 cm$^{-1}$ and 1740 cm$^{-1}$.

Example 12

1-[4-Amino-3-bromo-5-(N-ethyl-cyclohexylaminomethyl)-benzoyloxy]-2-acetocy-3-[(+)-6-methoxy-α-methyl-2-naphthalineacetoxy]-n-propane 10 gm (0.0156 mol) of 1-[4-amino-3-bromo-5-(N-ethylcyclohexylaminomethyl)-benzoyloxy]-2-hydroxy-3-[(+)-6-methoxy-α-methyl-2-naphthaline-acetoxy]-n-propane and 0.97 gm (0.0156 mol) of pyridine were dissolved in 150 ml of absolute tetrahydrofuran. To this solution a mixture of 1.25 gm (0.0156 mol) of acetyl chloride and 20 ml of absolute tetrahydrofuran was added dropwise while stirring at room temperature. The reaction solution was stirred for 3 hours and then left standing overnight. The tetrahydrofuran was distilled off in a water aspirator vacuum, and the oily residue was dissolved in chloroform and washed with dilute ammonia. The chloroform phase was dried with sodium sulfate and evaporated in vacuo. The crude product was purified on a silicagel column with toluene/acetone (4:1). The obtained oil was dissolved in absolute ethanol ether. After acidifying the solution with ethanolic hydrochloric acid, the hydrochloride was obtained by evaporation of the solution to dryness.

M.p. of the hydrochloride: 87°–93° C.

Example 13

1-[4-Amino-3-bromo-5-(N-ethyl-cyclohexylaminomethyl)-benzamido]-2-[1-(4-chlorobenzoyl)-5-methoxy-2-methyl-1H-indole-3-acetamido]-ethane 4.8 gm (0.012 mol) of 1-[4-amino-3-bromo-5-(N-ethyl-cyclohexylaminomethyl)-benzamido]-2-amino-ethane and 4.9 gm (0.012 mol) of 1-(4-chlorobenzoyl)-5-methoxy-2-methyl-1H-indole-3-acetic acid imidazolide were dissolved in 75 ml of tetrahydrofuran. After adding a catalytic amount of a sodium hydride dispersion in oil, the solution was stirred for one hour at room temperature. The tetrahydrofuran was then distilled off in vacuo, the residue was dissolved in chloroform, and the solution was washed three times with water. The organic phase was dried over sodium sulfate, filtered through activated charcoal and evaporated in vacuo. The obtained residue was dissolved in isopropanol, and the hydrochloride was precipitated by addition of ether after acidifying with ethereal hydrochloric acid.

M.p. of the hydrochloride: from 145° C. (decomp.).

Example 14

2-[4-Amino-3-bromo-5-(N-ethyl-cyclohexylaminomethyl)-benzoyloxy]-2'-[1-(4-chlorobenzoyl)-5-methoxy-2-methyl-1H-indole-3-acetoxy]-diethylsulfoxide To a solution of 10 gm (0.0125 mol) of 2-[4-amino-3-bromo-5-(N-ethyl-cyclohexylaminomethyl)-benzoyloxy]-2'-[1-(4-chlorobenzoyl)-5-methoxy-2-methyl-1H-indole-3-acetoxy]diethylsulfide in 100 ml of glacial acetic acid, 1.5 gm (0.0125 mol) of an aqueous 30% hydrogen peroxide solution were added while stirring at room temperature. The reaction solution was stirred for 2 hours at room temperature and subsequently evaporated in vacuo at 40° C. The residue was dissolved by adding 100 ml of tetrahydrofuran in 300 ml of ether, and the solution was washed with 2 N ammonium and water. Subsequently, the organic phase was dried with magnesium sulfate, evaporated in vacuo to dryness at 35° C., and the evaporation residue was purified on a silicagel column with methylene chloride/methanol (75:1). The desired fractions were combined and evaporated to dryness at 35° C. in vacuo. The reaction product was obtained as an oily evaporation residue, from which residual solvent was removed with sulfuric acid drying agent in vacuo at room temperature.

$C_{39}H_{45}BrClN_3O_7S$ (815.2): Calc.: C-57.46%; H-5.56%; Br-9.80%; Cl-4.35%; N-5.15%; Found: C-57.64%; H-5.75%; Br-9.64%; Cl-4.28%; N-5.00%.

Example 15

2-[4-Amino-3-bromo-5-(N-ethyl-cyclohexylaminomethyl)-benzoyloxy]-2'-[1-(4-chlorobenzoyl)-5-methoxy-2-methyl-1H-indole-3-acetoxy]-diethylsulfone To a solution of 10 gm (0.0125 mol) of 2-[4-amino-3-bromo-5-(N-ethyl-cyclohexylaminomethyl)-benzoyloxy]-2'-[1-(4-chloro-benzoyl)-5-methoxy-2-methyl-1H-indole-3-acetoxy]-diethylsulfide in 150 ml of glacial acetic acid, 3 gm (0.025 mol) of an aqueous 30% hydrogen peroxide solution were added. After stirring the mixture for 130 hours at room temperature, the glacial acetic acid was removed in vacuo at 40° C. Subsequently, the evaporation residue was dissolved in 300 ml of ether by adding 150 ml of tetrahydrofuran. The solution was washed with 2 N ammonia and water. The organic phase was dried over magnesium sulfate and evaporated in vacuo. The evaporation residue was chromatographed twice on a silicagel column with ether/tetrahydrofuran (10:1) and with methylene-chloride/methanol (75:1). After fractionation and evaporation of the combined fractions in vacuo at 35° C. a foamy evaporation residue was obtained.

$C_{39}H_{45}BrClN_3O_8S$ (831.2): Calc.: C-56.35%; H-5.46%; Br-9.61%; Cl-4.27%; N-5.06%; S-3.86%;

Found: C:56.11%; H-5.41%; Br-9.91%; Cl-4.41%; N-4.95%; S-4.10%.

Example 16

1-[4-Amino-3-bromo-5-(N-ethyl-cyclohexylaminomethyl)-benzoyloxy]-3-[1-(4-chlorobenzoyl)-5-methoxy-2-methyl-1H-indole-3-acetoxy]-n-propane This compound was prepared from 1-(4-chlorobenzoyl)-5-methoxy-2-methyl-1H-indole-3-acetic acid imidazolide and 1-[4-amino-3-bromo-5-(N-ethyl-cyclohexylaminomethyl)-benzoyloxy]-3-hydroxy-n-propane analogous to Example 1. Oil.

$C_{38}H_{43}BrClN_3O_6$ (743.1): Calc.: C-60.60%; H-5.76%; Br-10.61%; Cl-4.71%; N-5.58%; Found: C-60.80%; H-5.93%; Br-10.73%; Cl-4.76%; N-5.35%.

Example 17

1-[4-Amino-3-bromo-5-(N-ethyl-cyclohexylaminomethyl)-benzoyloxy]-4-[1-(4-chlorobenzoyl)-5-methoxy-2-methyl-1H-indole-3-acetoxy]-n-butane This compound was prepared from 1-(4-chlorobenzoyl)-5-methoxy-2-methyl-1H-indole-3-acetic acid imidazolide and 1-[4-amino-3-bromo-5-(N-ethyl-cyclohexylaminomethyl)-benzoyloxy]-4-hydroxy-n-butane analogous to Example 1. Oil.

Calc.: C-61.06%; H-5.91%; Br-10.42%; Cl-4.62%; N-5.48%; Found: C-61.30%; H-6.08%; Br-10.05%; Cl-4.46%; N-5.46%.

Example 18

1-[4-Amino-3-bromo-5-(N-ethyl-cyclohexylaminomethyl)-benzoyloxy]-5[1-(4-chlorobenzoyl)-5-methoxy-2-methyl-1H-indole-3-acetoxy]-n-pentane This compound was prepared from 1-(4-chlorobenzoyl)-5-methoxy-2-methyl-1H-indole-3-acetic acid imidazolide and 1-[4-amino-3-bromo-5-(N-ethyl-cyclohexylaminomethyl)-benzoyloxy]-5-hydroxy-n-pentane analogous to Example 1. Oil.

$C_{40}H_{47}BrClN_3O_6$ (781.2): Calc.: C-61.50%; H-6.06%; Br-10.23%; Cl-4.54%; N-5.38%; Found: C-61.70%; H-6.11%; Br-10.10%; Cl-4.48%; N-5.18%.

Example 19

1-[4-Amino-3-bromo-5-(N-ethyl-cyclohexylaminomethyl)-benzoyloxy]-6-[1-(4-chlorobenzoyl)-5-methoxy-2-methyl-1H-indole-3-acetoxy]-n-hexane This compound was prepared from 1-(4-chlorobenzoyl)-5-methoxy-2-methyl-1H-indole-3-acetic acid imidazolide and 1-[4-amino-3-bromo-5-(N-ethyl-cyclohexyl-aminomethyl)-benzoyloxy]-6-hydroxy-n-hexane analogous to Example 1. Oil.

$C_{41}H_{49}BrClN_3O_6$ (795.2): Calc.: C-61.93%; H-6.21%; Br-10.05%; Cl-4.46%; N-5.28%; Found: C-62.20%; H-6.15%; Br-10.30%; Cl-4.57%; N-5.32%.

Example 20

1-[4-Amino-3-bromo-5-(N-ethyl-cyclohexylaminomethyl)-benzoyloxy]-2-{2-[(2,6-dichlorophenyl)-amino]-phenylacetoxy}-ethane This compound was prepared from 2-[4-amino-3-bromo-5-(N-ethyl-cyclohexylaminomethyl)-benzoyloxy]-ethyl chloride and sodium 2-[(2,6-dichlorophenyl)-amino]-phenyl-acetate analogous to Example 8.
M.p. of the hydrochloride: 94°–98° C.

Example 21

1-[4-Amino-3-bromo-5-(N-ethyl-cyclohexylaminomethyl)-benzoyloxy]-3-{2-[(2,6-dichlorophenyl)-amino]-phenylacetoxy}-n-propane This compound was prepared from 3-[4-amino-3-bromo-5-(N-ethyl-cyclohexylaminomethyl)-benzoyloxy]-n-propyl chloride and sodium 2-[(2,6-dichlorophenyl)-amino]-phenylacetate analogous to Example 8.
M.p. of the hydrochloride: 76°–92° C.

Example 22

1-[4-Amino-3-bromo-5-(N-ethyl-cyclohexylaminomethyl)-benzoyloxy]-4-{2-[(2,6-dichlorophenyl)-amino]-phenyl-acetoxy}-n-butane This compound was prepared from 4-[4-amino-3-bromo-5-(N-ethyl-cyclohexylaminomethyl)-benzoyloxy]-n-butyl chloride and sodium 2-[(2,6-dichlorophenyl)-amino]-phenyl-acetate analogous to Example 8.
M.p. of the hydrochloride: 75°–83° C.

Example 23

1-[4-Amino-3-bromo-5-(N-ethyl-cyclohexylaminomethyl)-benzoyloxy]-6-{2-[(2,6-dichlorophenyl)-amino]-phenylacetoxy}-n-hexane This compound was prepared from 6-[4-amino-3-bromo-5-(N-ethyl-cyclohexylaminomethyl)-benzoyloxy]-n-hexyl chloride and sodium 2-[(2,6-dichlorophenyl)-amino]-phenyl-acetate analogous to Example 8.
M.p. of the hydrochloride: 105°–108° C.

Example 24

1-[4-Amino-3-bromo-5-(N-ethyl-cyclohexylaminomethyl)-benzoyloxy]-2-(3-benzoyl-α-methyl-phenylacetoxy)-ethane This compound was prepared from 3-benzoyl-α-methyl-phenyl-acetic acid imidazolide and 1-[4-amino-3-bromo-5-(N-ethyl-cyclohexylaminomethyl)-benzoyloxy]-2-hydroxy-ethane analogous to Example 1.
M.p. of the hydrochloride: 60°–64° C.

Example 25

1-[4-Amino-3-bromo-5-(N-ethyl-cyclohexylaminomethyl)-benzoyloxy]-3-(3-benzoyl-α-methyl-phenylacetoxy)-n-propane This compound was prepared from 3-benzoyl-α-methyl-phenyl-acetic acid imidazolide and 1-[4-amino-3-bromo-5-(N-ethyl-cyclohexylaminomethyl)-benzoyloxy]-3-hydroxy-n-propane analogous to Example 1.
M.p. of the hydrochloride: beginning at 56° C. (sintering).

Example 26

1-[4-Amino-3-bromo-5-(N-ethyl-cyclohexylaminomethyl)-benzoyloxy]-4-(3-benzoyl-α-methyl-phenylacetoxy)-n-butane The compound was prepared from 3-benzoyl-α-methyl-phenyl-acetic acid imidazolide and 1-[4-amino-3-bromo-5-(N-ethyl-cyclohexylaminomethyl)-benzoyloxy]-4-hydroxy-n-butane analogous to Example 1.
M.p. of the hydrochloride: 59°–64° C.

Example 27

1-[4-Amino-3-bromo-5-(N-ethyl-cyclohexylaminomethyl)-benzoyloxy]-5-(3-benzoyl-α-methylphenylacetoxy)-n-pentane This compound was prepared from 3-benzoyl-α-methyl-phenyl-acetic acid imidazolide and 1-[4-amino-3-bromo-5-(N-ethyl-cyclohexylaminomethyl)-benzoyloxy]-5-hydroxy-n-pentane analogous to Example 1. Oil.

IR-spectrum (methylene chloride): Ester-CO 1700 cm$^{-1}$ and 1730 cm$^{-1}$

UV-spectrum (ethanol): λ max. 258 nm, 295 nm.

Example 28

1-[4-Amino-3-bromo-5-(N-ethyl-cyclohexylaminomethyl)-benzoyloxy]-6-(3-benzoyl-α-methylphenylacetoxy)-n-hexane This compound was prepared from 3-benzoyl-α-methyl-phenyl-acetic acid imidadolide and 1-[4-amino-3-bromo-5-(N-ethyl-cyclohexylaminomethyl)-benzoyloxy]-6-hydroxy-n-hexane analogous to Example 1. Oil.

IR-spectrum (methylene chloride): Ester-CO 1710 cm$^{-1}$ and 1730 cm$^{-1}$

UV-spectrum (ethanol): λmax 258 nm, 295 nm.

Example 29

1-[4-Amino-3-bromo-5-(N-ethyl-cyclohexylaminomethyl)-benzoyloxy]-2-[(+)-6-methoxy-α-methyl-2-naphthaline-acetoxy]-ethane This compound was prepared from (+)-6-methoxy-α-methyl-2-naphthaline-acetic acid imidazolide and 1-[4-amino-3-bromo-5-(N-ethyl-cyclohexyl-aminomethyl)-benzoyloxy]-2-hydroxy-ethane analogous to Example 1. Oil.

IR-spectrum (methylene chloride):
NH$_2$: 3440 cm$^{-1}$
N-alkyl: 2920 cm$^{-1}$
OCH$_3$: 2850 cm$^{-1}$
Ester-CO: 1730 and 1710 cm$^{-1}$ UV-spectrum (ethanol): λ max 234 nm, 295 nm.

Example 30

1-[4-Amino-3-bromo-5-(N-ethyl-cyclohexylaminomethyl)-benzoyloxy]-3-[(+)-6-methoxy-α-methyl-2-naphthaline-acetoxy]-n-propane This compound was prepared from (+)-6-methoxy-α-methyl-2-naphthaline-acetic acid imidazolide and 1-[4-amino-3-bromo-5-(N-ethyl-cyclohexylaminomethyl)-benzoyloxy]-3-hydroxy-n-propane analogous to Example 1. The hydrochloride was obtained as a foam.

C$_{33}$H$_{41}$BrN$_2$O$_5$ x HCl (662.1): Calc.: C-59.87%; H-6.39%; Br-12.07%; Cl-5.36%; N-4.23%; Found: C-59.50%; H-6.29%; Br-12.30%; Cl-5.44%; N-4.02%.

Example 31

1-[4-Amino-3-bromo-5-(N-ethyl-cyclohexylaminomethyl)-benzoyloxy]-4-[(+)-6-methoxy-α-methyl-2-naphthaline-acetoxy]-n-butane This compound was prepared from (+)-6-methoxy-α-methyl-2-naphthaline-acetic acid imidazolide and 1-[4-amino-3-bromo-5-(N-ethyl-cyclohexylaminomethyl)-benzoyloxy]-4-hydroxy-n-butane analogous to Example 1. Oil.

IR-spectrum (methylene chloride):
NH$_2$: 3440 cm$^{-1}$
N-alkyl: 2920 cm$^{-1}$
OCH$_3$: 2850 cm$^{-1}$
Ester-CO: 1735 and 1710 cm$^{-1}$ UV-spectrum (ethanol): λ max 234 nm, 295 nm.

Example 32

1-[4-Amino-3-bromo-5-(N-ethyl-cyclohexylaminomethyl)-benzoyloxy]-5-[(+)-6-methoxy-α-methyl-2-naphthaline acetoxy]-n-pentane This compound was prepared from (+)-6-methoxy-α-methyl-2-naphthaline-acetic acid imidazolide and 1-[4-amino-3-bromo-5-(N-ethyl-cyclohexylaminomethyl)-benzoyloxy]-5-hydroxy-n-pentane analogous to Example 1. Oil.

IR-spectrum (methylene chloride):
NH$_2$: 3440 cm$^{-1}$
N-alkyl: 2920 cm$^{-1}$
OCH$_3$: 2850 cm$^{-1}$
Ester-CO: 1730 and 1710 cm$^{-1}$ UV-spectrum (ethanol): λ max 234 nm, 295 nm.

Example 33

1-[4-Amino-3-bromo-5-(N-ethyl-cyclohexylaminomethyl)-benzoyloxy]-6-[(+)-6-methoxy-α-methyl-2-naphthaline acetoxy]-n-hexane This compound was prepared from (+)-6-methoxy-α-methyl-2-naphthaline-acetic acid imidazolide and 1-[4-amino-3-bromo-5-(N-ethyl-cyclohexylaminomethyl)-benzoyloxy]-6-hydroxy-n-hexane analogous to Example 1. Oil.

IR-spectrum (methylene chloride):
NH$_2$: 3430 cm$^{-1}$
N-alkyl: 2920 cm$^{-1}$
OCH$_3$: 2850 cm$^{-1}$
Ester-CO: 1730 and 1710 cm$^{-1}$ UV-spectrum (ethanol): λ max 234 nm, 295 nm.

Example 34

1-[4-Amino-3-bromo-5-(N-ethyl-cyclohexylaminomethyl)-benzoyloxy]-2-[α-methyl-4-(2-methylpropyl)-phenylacetoxy]-ethane This compound was prepared from α-methyl-4-(2-methylpropyl)-phenyl-acetic acid imidazolide and 1-[4-amino-3-bromo-5-(N-ethylcyclohexylaminomethyl)-benzoyloxy]-2-hydroxy-ethane analogous to Example 1. The hydrochloride was obtained as an oil.

C$_{31}$H$_{43}$BrN$_2$O$_4$ x HCl (624.1): Calc.: C-59.66%; H-7.11%; Br-12.81%; Cl-5.68%; N-4.49%; Found: C-59.50%; H-7.32%; Br-12.64%; Cl-5.61%; N-4.43%.

Example 35

1-[4-Amino-3-bromo-5-(N-ethyl-cyclohexylaminomethyl)-benzoyloxy]-3-[α-methyl-4-(2-methylpropyl)-phenylacetoxy]-n-propane This compound was prepared from α-methyl-4-(2-methylpropyl)-phenyl-acetic acid imidazolide and 1-[4-amino-3-bromo-5-(N-ethyl-cyclohexylaminomethyl)-benzoyloxy]-3-hydroxy-n-propane analogous to Example 1. The hydrochloride was obtained as an oil.

C$_{32}$H$_{45}$BrN$_2$O$_4$ x HCl (638.1): Calc.: C-60.24%; H-7.27%; Br-12.52%; Cl-5.56%; N-4.39%; Found: C-60.30%; H-7.53%; Br-12.30%; Cl-5.45%; N-4.36%.

Example 36

1-[4-Amino-3-bromo-5-(N-ethyl-cyclohexylaminomethyl)-benzoyloxy]-4-[α-methyl-4-(2-methylpropyl)-phenylacetoxy]-n-butane This compound was prepared from α-methyl-4-(2-methylpropyl)-phenyl-acetic acid imidazolide and 1-[4-amino-3-bromo-5-(N-ethyl-cyclohexylaminomethyl)-benzoyloxy]-4-hydroxy-n-butane analogous to Example 1.

M.p. of the hydrochloride: 77°–79° C.

Example 37

1-[4-Amino-3-bromo-5-(N-ethyl-cyclohexylaminomethyl)-benzoyloxy]-5-[α-methyl-4-(2-methylpropyl)-phenylacetoxy]-n-pentane This compound was prepared from α-methyl-4-(2-methylpropyl)-phenyl-acetic acid imidazolide and 1-[4-amino-3-bromo-5-(N-ethyl-cyclohexylaminomethyl)-benzoyloxy]-5-hydroxy-n-pentane analogous to Example 1.

M.p. of the hydrochloride: 119°–121° C.

Example 38

1-[4-Amino-3-bromo-5-(N-ethyl-cyclohexylaminomethyl)-benzoyloxy]-2-(2-acetoxy-benzoyloxy)-ethane This compound was prepared from 2-acetoxy-benzoyl chloride and 1-[4-amino-3-bromo-5-(N-ethyl-cyclohexylaminomethyl)-benzoyloxy]-2-hydroxy-ethane analogous to Example 5. Oil.

IR-spectrum (methylene chloride): Ester-CO 1710 and 1770 cm$^{-1}$

UV-spectrum (ethanol): λ max 231 nm, 300 nm.

Example 39

1-[4-Amino-3-bromo-5-(N-ethyl-cyclohexylaminomethyl)-benzoyloxy]-2-[2-fluoro-α-methyl-(1,1'-biphenyl)-4-acetoxy]-ethane This compound was prepared from 2-fluoro-α-methyl-(1,1'-biphenyl)-4-acetic acid imidazolide and 1-[4-amino-3-bromo-5-(N-ethyl-cyclohexylaminomethyl)-benzoyloxy]-2-hydroxy-ethane analogous to Example 1. The hydrochloride was obtained as an oil.

$C_{33}H_{38}BrFN_2O_4$ x HCl (662.1): Calc.: C-59.87%; H-5.94%; Br-12.07%; Cl-5.36%; N-4.23%; Found: C-60.16%; H-6.17%; Br-11.95%; Cl-5.29%; N-4.84%.

Example 40

1-(4-Amino-3-bromo-5-diethylaminomethyl-benzoyloxy)-2-[1-(4-chlorobenzoyl)-5-methoxy-2-methyl-1H-indole-3-acetoxy]-ethane This compound was prepared from 1-(4-chlorobenzoyl)-5-methoxy-2-methyl-1H-indole-3-acetic acid imidazolide and 1-(4-amino-3-bromo-5-diethylaminomethyl-benzoyloxy)-hydroxy-ethane analogous to Example 1.

M.p. of the hydrochloride: 186°–187° C.

Example 41

1-(4-Amino-3-bromo-5-diethylaminomethyl-benzoyloxy)-3-[1-(4-chloro-benzoyl)-5-methoxy-2-methyl-1H-indole-3-acetoxy]-n-propane This compound was prepared from 1-(4-chlorobenzoyl)-5-methoxy-2-methyl-1H-indole-3-acetic acid imidazolide and 1-(4-amino-3-bromo-5-diethylaminomethyl-benzoyloxy)-3-hydroxy-n-propane analogous to Example 1.

M.p. of the hydrochloride: 123°–125° C.

Example 42

1-(4-Amino-3-bromo-5-diethylaminomethyl-benzoyloxy)-4-[1-(4-chloro-benzoyl)-5-methoxy-2-methyl-1H-indole-3-acetoxy]-n-butane This compound was prepared from 1-(4-chlorobenzoyl)-5-methoxy-2-methyl-1H-indole-3-acetic acid imidazolide and 1-(4-amino-3-bromo-5-diethylaminomethyl-benzoyloxy)-4-hydroxy-n-butane analogous to Example 1.

M.p. of the hydrochloride: 74°–85° C.

Example 43

1-(4-Amino-3-bromo-5-diethylaminomethyl-benzoyloxy)-5-[1-(4-chloro-benzoyl)-5-methoxy-2-methyl-1H-indole-3-acetoxy]-n-pentane This compound was prepared from 1-(4-chlorobenzoyl)-5-methoxy-2-methyl-1H-indole-3-acetic acid imidazolide and 1-(4-amino-3-bromo-5-diethylaminomethyl-benzoyloxy)-5-hydroxy-n-pentane analogous to Example 1.

M.p. of the hydrochloride: 70°–74° C.

EXAMPLE 44

1-(4-Amino-3-bromo-5-diethylaminomethyl-benzoyloxy)-6-[1-(4-chlorobenzoyl)-5-methoxy-2-methyl-1H-indole-3-acetoxy]-n-hexane This compound was prepared from 1-(4-chlorobenzoyl)-5-methoxy-2-methyl-1H-indole-3-acetic acid imidazolide and 1-(4-amino-3-bromo-5-diethylaminomethyl-benzoyloxy)-6-hydroxy-n-hexane analogous to Example 1.

M.p. of the hydrochloride: 131°–134° C.

Example 45

1-(4-Amino-3-bromo-5-diethylaminomethyl-benzoyloxy)-2-{2-[(2,6-dichlorophenyl)-amino]-phenylacetoxy}-ethane This compound was prepared from sodium 2-[(2,6-dichlorophenyl)-amino]-phenyl-acetate and 2-(4-amino-3-bromo-5-diethylaminomethyl-benzoyloxy)-ethyl chloride analogous to Example 8.

M.p. of the hydrochloride: 76°–82° C.

Example 46

1-(4-Amino-3-bromo-5-diethylaminomethyl-benzoyloxy)-3-{2-[(2,6-dichlorophenyl)-amino]-phenylacetoxy}-n-propane This compound was prepared from sodium 2-[(2,6-dichlorophenyl)-amino]-phenyl-acetate and 3-(4-amino-3-bromo-5-diethylaminomethyl-benzoyloxy)-n-propyl chloride analogous to Example 8.

M.p. of the hydrochloride: 64°–78° C.

Example 47

1-(4-Amino-3-bromo-5-diethylaminomethyl-benzoyloxy)-4-{2-[(2,6-dichlorophenyl)-amino]-phenylacetoxy}-n-butane This compound was prepared from sodium 2-[(2,6-dichlorophenyl)-amino]-phenyl-acetate and 4-(4-amino-3-bromo-5-diethylaminomethyl-benzoyloxy)-n-butyl chloride analogous to Example 8.

M.p. of the hydrochloride: 58°–69° C.

Example 48

1-(4-Amino-3-bromo-5-diethylaminomethyl-benzoyloxy)-5-{2-[(2,6-dichlorophenyl)-amino]-phenylacetoxy}-n-pentane This compound was prepared from sodium 2-[(2,6-dichlorophenyl)-amino]-phenyl-acetate sodium salt and 5-(4-amino-3-bromo-5-diethylaminomethyl-benzoyloxy)-n-pentyl chloride analogous to Example 8.

M.p. of the hydrochloride: 64°–72° C.

Example 49

1-(4-Amino-3-bromo-5-diethylaminomethyl-benzoyloxy)-2-[(+)-6-methoxy-α-methyl-2-naphthaline acetoxy]-ethane This compound was prepared from (+)-6-methoxy-α-methyl-2-naphthaline-acetic acid imidazolide and 1-(4-amino-3-bromo-5-diethylaminomethyl-benzoyloxy)-2-hydroxyethane analogous to Example 1.

M.p. of the hydrochloride: 123°–124° C.

Example 50

1-(4-Amino-3-bromo-5-diethylaminomethyl-benzoyloxy)-3-[(+)-6-methoxy-α-methyl-2-naphthaline acetoxy]-n-propane This compound was prepared from (+)-6-methoxy-α-methyl-2-naphthaline-acetic acid imidazolide and 1-(4-amino-3-bromo-5-diethylaminomethyl-benzoyloxy)-3-hydroxy-n-propane analogous to Example 1.

M.p. of the hydrochloride: 63°–69° C.

Example 51

1-(4-Amino-3-bromo-5-diethylaminomethyl-benzoyloxy)-4-[(+)-6-methoxy-α-methyl-2-naphthalineacetoxy]-n-butane This compound was prepared from (+)-6-methoxy-α-methyl-2-naphthaline-acetic acid imidazolide and 1-(4-amino-3-bromo-5-diethylaminomethyl-benzoyloxy)-4-hydroxy-n-butane analogous to Example 1.

M.p. of the hydrochloride: 47°–71° C.

Example 52

1-(4-Amino-3-bromo-5-diethylaminomethyl-benzoyloxy)-5-[(+)-6-methoxy-α-methyl-2-naphthalineacetoxy]-n-pentane This compound was prepared from (+)-6-methoxy-α-methyl-2-naphthaline-acetic acid imidazolide and 1-(4-amino-3-bromo-5-diethylaminomethyl-benzoyloxy)-5-hydroxy-n-pentane analogous to Example 1. Oil.

IR-spectrum (methylene chloride): Ester-CO: 1700 and 1725 cm$^{-1}$

UV-spectrum (ethanol): λ max 230 nm, 290 nm.

Example 53

1-(4-Amino-3-bromo-5-diethylaminomethyl-benzoyloxy)-2-(2-acetoxy-benzoyloxy)-ethane This compound was prepared from 2-acetoxybenzoyl chloride and 1-[4-amino-3-bromo-5-diethylaminomethyl-benzoyloxy]-2-hydroxy-ethane analogous to Example 5. Oil.

$C_{23}H_{27}BrN_2O_6$ (507.4): Calc.: C-54.45%; H-5.36%; Br-15.75%; N-5.52%; Found: C-54.30%; H-5.46%; Br-16.20%; N-5.47%.

Example 54

1-(4-Amino-3-bromo-5-hexamethyleneiminomethyl-benzoyloxy)-2-[1-(4-chlorobenzoyl)-5-methoxy-2-methyl-1H-indole-3-acetoxy]-ethane This compound was prepared from 1-(4-chlorobenzoyl)-5-methoxy-2-methyl-1H-indole-3-acetic acid imidazolide and 1-(4-amino-3-bromo-5-hexamethyleneimino-methylbenzoyloxy)-2-hydroxy-ethane analogous to Example 1.

M.p. of the hydrochloride: 207°–208° C.

Example 55

1-[4-Amino-3-bromo-5-(N-ethyl-cycloheptylaminomethyl)benzoyloxy]-2-[1-(4-chlorobenzoyl)-5-methoxy-2-methyl-1H-indole-3-acetoxy]-ethane This compound was prepared from 1-(4-chlorobenzoyl)-5-methoxy-2-methyl-1H-indole-3-acetic acid imidazolide and 1-[4-amino-3-bromo-5-(N-ethyl-chloroheptylaminomethyl)-benzoyloxy]-2-hydroxy-ethane analogous to Example 1.

M.p. of the hydrochloride: 90°–120° C.

Example 56

1-(4-Amino-3-bromo-5-tert.butylaminomethyl-benzoyloxy)-2-[1-(4-chlorobenzoyl)-5-methoxy-2-methyl-1H-indole-3-acetoxy]-ethane This compound was prepared from 1-(4-chlorobenzoyl)-5-methoxy-2-methyl-1H-indole-3-acetic acid imidazolide and 1-(4-amino-3-bromo-5-tert.butylaminomethyl-benzoyloxy)-2-hydroxy-ethane analogous to Example 1. The hydrochloride was obtained as an oil.

$C_{33}H_{35}BrClN_3O_6$ x HCl (721.5): Calc.: C-54.89%; H-5.03%; Br-11.08%; Cl-9.83%; N-5.82%; Found: C-55.10%; H-5.26%; Br-10.90%; Cl-9.67%; N-5.62%.

Example 57

1-[4-Amino-3-bromo-5-(N-ethyl-cyclopentylaminomethyl)benzoyloxy]-2-[1-(4-chlorobenzoyl)-5-methoxy-2-methyl-1H-indole-3-acetoxy]-ethane This compound was prepared from 1-(4-chlorobenzoyl)-5-methoxy-2-methyl-1H-indole-3-acetic acid imidazolide and 1-[4-amino-3-bromo-5-(N-ethyl-cyclopentylaminomethyl)-benzoyloxy]-2-hydroxy-ethane analogous to Example 1.

M.p. of the hydrochloride: 206°–207° C.

Example 58

1-(4-Amino-3-bromo-5-dimethylaminomethyl-benzoyloxy)-2-[1-(4-chlorobenzoyl)-5-methoxy-2-methyl-1H-indole-3-acetoxy]-ethane This compound was prepared from 1-(4-chlorobenzoyl)-5-methoxy-2-methyl-1H-indole-3-acetic acid imidazolide and 1-(4-amino-3-bromo-5-dimethylaminomethylbenzoyloxy)-2-hydroxy-ethane analogous to Example 1.

M.p. of the hydrochloride: 174°–176° C.

Example 59

1-[4-Amino-3-bromo-5-(N-cyclohexyl-methylaminomethyl)benzoyloxy]-2-[1-(4-chlorobenzoyl)-5-methoxy-2-methyl-1H-indole-3-acetoxy]-ethane This compound was prepared from 1-(4-chlorobenzoyl)-5-methoxy-2-methyl-1H-indole-3-acetic acid imidazolide and 1-[4-amino-3-bromo-5-(N-cyclohexyl-methylaminomethyl)-benzoyloxy]-2-hydroxy-ethane analogous to Example 1.

M.p. of the hydrochloride: 151°–153° C.

Example 60

1-[4-Amino-3-bromo-5-(N-cyclohexyl-n-propylaminomethyl)benzoyloxy]-2-[1-(4-chlorobenzoyl)-5-methoxy-2-methyl-1H-indole-3-acetoxy]-ethane This compound was prepared from 1-(4-chlorobenzoyl)-5-methoxy-2-methyl-1H-indole-3-acetic acid imidazolide and 1-[4-amino-3-bromo-5-(N-cyclohexyl-n-propylaminomethyl)-benzoyloxy]-2-hydroxy-ethane analogous to Example 1.

M.p. of the hydrochloride: 129°–132° C.

Example 61

1-(4-Amino-3-bromo-5-pyrrolidinomethyl-benzoyloxy)-2-[1-(4-chlorobenzoyl)-5-methoxy-2-methyl-1H-indole-3-acetoxy]-ethane This compound was prepared from 1-(4-chlorobenzoyl)-5-methoxy-2-methyl-1H-indole-3-acetic acid imidazolide and 1-(4-amino-3-bromo-5-pyrrolidinomethylbenzoyloxy)-2-hydroxy-ethane analogous to Example 1.

M.p. of the hydrochloride: 218°–220° C.

Example 62

1-(4-Amino-3-bromo-5-piperidinomethyl-benzoyloxy)-2-[1-(4-chlorobenzoyl)-5-methoxy-2-methyl-1H-indole-3-acetoxy]-ethane This compound was prepared from 1-(4-chlorobenzoyl)-5-methoxy-2-methyl-1H-indole-3-acetic acid imidazolide and 1-(4-amino-3-bromo-5-piperidinomethylbenzoyloxy)-2-hydroxy-ethane analogous to Example 1.

M.p. of the hydrochloride: 208°–209° C.

Example 63

1-(4-Amino-3-bromo-5-morpholinomethyl-benzoyloxy)-2-[1-(4-chlorobenzoyl)-5-methoxy-2-methyl-1-H-indole-3-acetoxy]-ethane This compound was prepared from 1-(4-chlorobenzoyl)-5-methoxy-2-methyl-1H-indole-3-acetic acid imidazolide and 1-(4-amino-3-bromo-5-morpholinomethylbenzoyloxy)-2-hydroxy-ethane analogous to Example 1.

M.p. of the hydrochloride: 197°–199° C.

Example 64

1-[4-Amino-3-bromo-5-(4-methyl-piperazinomethyl)-benzoyloxy]-2-[1-(4-chlorobenzoyl)-5-methoxy-2-methyl-1H-indole-3-acetoxy]-ethane This compound was prepared from 1-(4-chlorobenzoyl)-5-methoxy-2-methyl-1H-indole-3-acetic acid imidazolide and 1-[4-amino-3-bromo-5-(4-methyl-piperazinomethyl)-benzoyloxy]-2-hydroxy-ethane analogous to Example 1.

M.p. of the dihydrochloride: 175°–177° C.

Example 65

1-(4-Amino-3-bromo-5-isopropylaminomethyl-benzoyloxy)-2-[1-(4-chlorobenzoyl)-5-methoxy-2-methyl-1H-indole-3-acetoxy]-ethane This compound was prepared from 1-(4-chlorobenzoyl)-5-methoxy-2-methyl-1H-indole-3-acetic acid imidazolide and 1-(4-amino-3-bromo-5-isopropylaminomethylbenzoyloxy)-2-hydroxy-ethane analogous to Example 1.

M.p. of the dihydrochloride: 115° C. (decomp.).

Example 66

1-[4-Amino-3-bromo-5-(N-methyl-n-propylaminomethyl)benzoyloxy]-2-[1-(4-chlorobenzoyl)-5-methoxy-2-methyl-1H-indole-3-acetoxy]-ethane This compound was prepared from 1-(4-chlorobenzoyl)-5-methoxy-2-methyl-1H-indole-3-acetic acid imidazolide and 1-[4-amino-3-bromo-5-(N-methyl-n-propylaminomethyl)-benzoyloxy]-2-hydroxy-ethane analogous to Example 1.

M.p. of the hydrochloride: 193°–195° C. (decomp.).

Example 67

1-(4-Amino-3-bromo-5-cyclohexylaminomethyl-benzoyloxy)-2-[1-(4-chlorobenzoyl)-5-methoxy-2-methyl-1H-indole-3-acetoxy]-ethane This compound was prepared from 1-(4-chlorobenzoyl)-5-methoxy-2-methyl-1H-indole-3-acetic acid imidazolide and 1-(4-amino-3-bromo-5-cyclohexylaminomethylbenzoyloxy)-2-hydroxy-ethane analogous to Example 1.

M.p. of the hydrochloride: 177°–179° C.

Example 68

1-[4-Amino-3-bromo-5-(N-benzyl-methylaminomethyl)-benzoyloxy]-2-(1-(4-chlorobenzoyl)-5-methoxy-2-methyl-1H-indole-3-acetoxy]-ethane This compound was prepared from 1-(4-chlorobenzoyl)-5-methoxy-2-methyl-1H-indole-3-acetic acid imidazolide and 1-[4-amino-3-bromo-5-(N-benzylmethylaminomethyl)-benzoyloxy]-2-hydroxy-ethane analogous to Example 1. The hydrochloride was obtained as an oil.

$C_{37}H_{34}BrN_3O_6 \times HCl$ (733.1): Calc.: C-60.62%; H-4.81%; Br-10.90%; Cl-4.84%; N-5.73%; Found: C-60.35%; H-5.04%; Br-11.24% Cl-4.97%; N-5.51%.

Example 69

1-[4-Amino-3-bromo-5-(2-diethylaminoethyl-aminomethyl)-benzoyloxy]-2-[1-(4-chlorobenzoyl)-5-methoxy-2-methyl-1H-indole-3-acetoxy]-ethane This compound was prepared from 1-(4-chlorobenzoyl)-5-methoxy-2-methyl-1H-indole-3-acetic acid imidazolide and 1-[4-amino-3-bromo-5-(2-diethylaminoethyl-aminomethyl)-benzoyloxy]-2-hydroxy-ethane analogous to Example 1.

M.p. of the dihydrochloride: 131°–135° C.

Example 70

1-[4-Amino-3-bromo-5-(N-ethyl-cyclopentylaminomethyl)-benzoyloxy]-5-{2-[2,6-dichlorophenyl)-amino]-phenylacetoxy}-n-pentane This compound was prepared from sodium 2-[(2,6-dichlorophenyl)-amino]-phenyl-acetate and 5-[4-amino-3-bromo-5-(N-ethyl-cyclopentylaminomethyl)-benzoyloxy]-n-pentyl chloride analogous to Example 8. The hydrochloride was obtained as an oil.

$C_{34}H_{40}BrCl_2N_3O_4 \times HCl$ (742.0): Calc. C-55.04%; H-5.57%; Br-10.77%; Cl-14.33%, N-5.66%; Found: C-55.08%; H-5.62%; Br-10.57%; Cl-14.07%; N-5.47%.

Example 71

1-[4-Amino-3-bromo-5-(N-ethyl-cycloheptylaminomethyl)-benzoyloxy]-5-{2-[(2,6-dichlorophenyl)-amino]-phenylacetoxy}-n-pentane This compound was prepared from sodium 2-[(2,6-dichlorophenyl)-amino]-phenyl-acetate and 5-[4-amino-3-bromo-5-(N-ethyl-cycloheptylaminomethyl)-benzoyloxy]-n-pentyl chloride analogous to Example 8.
M.p. of the hydrochloride: 107°–110° C.

Example 72

1-(4-Amino-3-bromo-5-tert.butylaminomethyl-benzoyloxy)-2-(3-benzoyl-α-methyl-phenylacetoxy)-ethane This compound was prepared from 3-benzoyl-α-methyl-phenyl acetic acid imidazolide and 1-(4-amino-3-bromo-5-tert.butylaminomethyl-benzoyloxy)-2-hydroxy-ethane analogous to Example 1.
M.p. of the hydrochloride: 77°–98° C.

Example 73

1-(4-Amino-3-bromo-5-hexamethyleneiminomethyl-benzoyloxy)-2-(3-benzoyl-α-methyl-phenylacetoxy)-ethane This compound was prepared from 3-benzoyl-α-methylphenyl acetic acid imidazolide and 1-(4-amino-3-bromo-5-hexamethyleneiminomethyl-benzoyloxy)-2-hydroxy-ethane analogous to Example 1.
M.p. of the hydrochloride: 66°–80° C.

Example 74

1-[4-Amino-3-bromo-5-(N-ethyl-cycloheptylaminomethyl)-benzoyloxy]-2-(3-benzoyl-α-methyl-phenylacetoxy)-ethane This compound was prepared from 3-benzoyl-α-methyl-phenyl-acetic acid imidazolide and 1-[4-amino-3-bromo-5-(N-ethyl-cycloheptylaminomethyl)-benzoyloxy]-2-hydroxy-ethane analogous to Example 1.
M.p. of the hydrochloride: 68°–79° C.

Example 75

1-[4-Amino-3-bromo-5-(N-ethyl-cyclopentylaminomethyl)-benzoyloxy]-2-(3-benzoyl-α-methyl-phenylacetoxy)-ethane This compound was prepared from 3-benzoyl-α-methylphenyl-acetic acid imidazolide and 1-[4-amino-3-bromo-5-(N-ethyl-cyclopentylaminomethyl)-benzoyloxy]-2-hydroxyethane analogous to Example 1.
M.p. of the hydrochloride: 63°–71° C.

Example 76

1-[4-Amino-3-bromo-5-(4-methyl-piperazinomethyl)-benzoyloxy]-2-(3-benzoyl-α-methyl-phenylacetoxy)-ethane This compound was prepared from 3-benzoyl-α-methylphenyl-acetic acid imidazolide and 1-[4-amino-3-bromo-5-(4-methyl-piperazinomethyl)-benzoyloxy]-2-hydroxy-ethane analogous to Example 1.
M.p. of the dihydrochloride: 182°–184° C.

Example 77

1-(4-Amino-3-bromo-5-morpholinomethyl-benzoyloxy)-2-(3-benzoyl-α-methyl-phenylacetoxy)-ethane This compound was prepared from 3-benzoyl-α-methylphenyl-acetic acid imidazolide and 1-(4-amino-3-bromo-5-morpholinomethyl-benzoyloxy)-2-hydroxyethane analogous to Example 1.
M.p. of the hydrochloride: 75° C. (decomp.).

Example 78

1-[4-Amino-3-bromo-5-(N-methyl-n-propylaminomethyl)benzoyloxy]-2-(3-benzoyl-α-methyl-phenylacetoxy)-ethane This compound was prepared from 3-benzoyl-α-methyl-phenyl-acetic acid imidazolide and 1-[4-amino-3-bromo-5-(N-methyl-n-propylaminomethyl)-benzoyloxy]-2-hydroxy-ethane analogous to Example 1.
M.p. of the hydrochloride: from 50° C. (decomp.).

Example 79

1-(4-Amino-3-bromo-5-isopropylaminomethyl-benzoyloxy-2-(3-benzoyl-α -methyl-phenylacetoxy)-ethane This compound was prepared from 3-benzoyl-α-methylphenyl-acetic acid imidazolide and 1-(4-amino-3-bromo-5-isopropylaminomethyl-benzoyloxy)-2-hydroxy-ethane analogous to Example 1.
M.p. of the hydrochloride: from 70° C. (decomp.).

Example 80

1-(4-Amino-3-bromo-5-cyclohexylaminomethyl-benzoyloxy)-2-(3-benzoyl-α-methyl-phenylacetoxy)-ethane This compound was prepared from 3-benzoyl-α-methylphenyl-acetic acid imidazolide and 1-(4-amino-3-bromo-5-cyclohexylaminomethyl-benzoyloxy)-2-hydroxy-ethane analogous to Example 1.
M.p. of the hydrochloride: from 80° C. (decomp.).

Example 81

1-[4-Amino-3-bromo-5-(N-benzyl-methylaminomethyl)benzoyloxy]-2-(3-benzoyl-α-methyl-phenylacetoxy)-ethane This compound was prepared from 3-benzoyl-α-methylphenyl-acetic acid imidazolide and 1-[4-amino-3-bromo-5-(N-benzyl-methylaminomethyl)-benzoyloxy]-2-hydroxy-ethane analogous to Example 1.
M.p. of the hydrochloride: from 75° C. (decomp.).

Example 82

1-[4-Amino-3-bromo-5-N-cyclohexyl-n-propylaminomethyl)benzoyloxy]-2-(3-benzoyl-α-methyl-phenylacetoxy)-ethane This compound was prepared from 3-benzoyl-α-methylphenyl-acetic acid imidazolide and 1-[4-amino-3-bromo-5-(N-cyclohexyl-n-propylaminomethyl)-benzoyloxy]-2-hydroxyethane analogous to Example 1. The hydrochloride was obtained as an oil.
$C_{35}H_{41}BrN_2O_5 \times HCl$ (686.1): Calc: C-61.27%; H-6.17%; Br-11.65%; Cl-5.17%; N-4.08%; Found: C-61.15%; H-6.36%; Br-11.60%; Cl-5.13%; N-4.07%.

Example 83

1-[4-Amino-3-bromo-5-(N-cyclohexyl-methylaminomethyl)benzoyloxy]-2-(3-benzoyl-α-methyl-phenylacetoxy)-ethane This compound was prepared from 3-benzoyl-α-methylphenyl-acetic acid imidazolide and 1-[4-amino-3-bromo-5-(N-cyclohexyl-methylaminomethyl)-benzoyloxy]-2-hydroxyethane analogous to Example 1.
M.p. of the hydrochloride: 50°–65° C. (decomp.).

Example 84

1-(4-Amino-3-bromo-5-dimethylaminomethyl-benzoyloxy)-2-(3-benzoyl-α-methyl-phenylacetoxy)-ethane This compound was prepared from 3-benzoyl-α-methylphenyl-acetic acid imidazolide and 1-(4-amino-3-bromo-5-dimethylaminomethyl-benzoyloxy)-2-hydroxy-ethane analogous to example 1.

M.p. of the hydrochloride: 65°-75° C. (decomp.).

Example 85

1-(4-Amino-3-bromo-5-pyrrolidinomethyl-benzoyloxy)-2-(3-benzoyl-α-methyl-phenylacetoxy)-ethane This compound was prepared from 3-benzoyl-α-methylpghenyl-acetic acid imidazolide and 1-(4-amino-3-bromo-5-pyrrolidinomethyl-benzoyloxy)-2-hydroxy-ethane analogous to Example 1.

M.p. of the hydrochloride: from 75° C. (sintering).

Example 86

1-(4-Amino-3-bromo-5-piperidinomethyl-benzoyloxy)-2-(3-benzoyl-α-methyl-phenylacetoxy)-ethane This compound was prepared from 3-benzoyl-α-methylphenyl-acetic acid imidazolide and 1-(4-amino-3-bromo-5-piperidinomethyl-benzoyloxy)-2-hydroxy-ethane analogous to Example 1.

M.p. of the hydrochloride: from 120° C. (decomp.).

Example 87

N-{2-[4-Amino-3-bromo-5-(N-ethyl-cyclohexylaminomethyl)benzoyloxy]-ethyl}-N-{2-[1-(4-chlorobenzoyl)-5-methoxy-2-methyl-1H-indole-3-acetoxy]-ethyl}-amine This compound was prepared from 1-(4-chlorobenzoyl)-5-methoxy-2-methyl-1H-indole-3-acetic acid chloride and N-{2-[4-amino-3-bromo-5-(N-ethyl-cyclohexylaminomethyl)-benzoyloxy]-ethyl}-N-(2-hydroxyethyl)-amine hydrochloride analogous to Example 5. The hydrochloride was obtained as an amorphous powder.

IR-spectrum (methylene chloride):
Amide-CO: 1680 cm$^{-1}$
Ester-CO: 1720 and 1740 cm$^{-1}$
O-methyl: 2870 cm$^{-1}$
N-alkyl: 2950 cm$^{-1}$
UV-spectrum (ethanol): λ max 230 nm (shoulder), 285 nm.

Example 88

N-{2-[4-Amino-3-bromo-5-(N-ethyl-cyclohexylaminomethyl)benzoyloxy]-ethyl}-N-{2-[1-(4-chlorobenzoyl)-5-methoxy-2-methyl-1H-indole-3-acetoxy]-ethyl}-ethylamine This compound was prepared from 1-(4-chlorobenzoyl)-5-methoxy-2-methyl-1H-indole-3-acetic acid imidazolide and N-{2-[4-amino-3-bromo-5-(N-ethyl-cyclohexylaminomethyl)benzoyloxy]-ethyl}-N-(2-hydroxyethyl)-ethylamine analogous to Example 3. The dihydrochloride was obtained as an amorphous powder.

$C_{41}H_{50}BrClN_4O_6 \times 2$ HCl (883.2): Calc.: C-55.76%; H-5.93%; Br-9.05%; Cl-12.04%; N-6.34%; Found: C-55.48%; H-6.12%; Br-8.97%; Cl-11.91%; N-6.24%.

Example 89

N-{2-[4-Amino-3-bromo-5-(N-ethyl-cyclohexylaminomethyl)benzoyloxy]-ethyl}-N-{2-[1-(4-chlorobenzoyl)-5-methoxy-2-methyl-1H-indole-3-acetoxy]-ethyl}-n-propylamine This compound was prepared from 1-(4-chlorobenzoyl)-5-methoxy-2-methyl-1H-indole-3-acetic acid chloride and N-{2-[4-amino-3-bromo-5-(N-ethyl-cyclohexylaminomethyl)benzoyloxy]-ethyl}-N-(2-hydroxyethyl)-n-propylamine in dichloromethane, analogous to Example 5. Oil.

$C_{42}H_{52}BrClN_4O_6$ (824.3): Calc.: C-61.20%; H-6.36%; Br-9.70%; Cl-4.30%; N-6.80%; Found: C-60.80%; H-6.61%; Br-9.94%; Cl-4.30%; N-6.77%.

Example 90

N-{2-[4-Amino-3-bromo-5-(N-ethyl-cyclohexylaminomethyl)benzoyloxy]-ethyl}-N-{2-[1-(4-chlorobenzoyl)-5-methoxy-2-methyl-1H-indole-3-acetoxy]-ethyl}-isopropylamine This compound was prepared from 1-(4-chlorobenzoyl)-5-methoxy-2-methyl-1H-indole-3-acetic acid chloride and N-{2-[4-amino-3-bromo-5-(N-ethyl-cyclohexylaminomethyl)benzoyloxy]-ethyl}-N-(2-hydroxyethyl)-isopropylamine in dichloromethane at 0° C., analogous to Example 5. Oil.

$C_{42}H_{52}BrClN_4O_6$ (824.3): Calc.: C-61.20%; H-6.36%; Br-9.70%; Cl-4.30%; N-6.80%; Found: C-61.00%; H-6.51%; Br-10.00%; Cl-4.43%; N-6.61%.

Example 91

N-{2-[4-Amino-3-bromo-5-(N-ethyl-cyclohexylaminomethyl)benzoyloxy]-ethyl}-N-{2-[1-(4-chlorobenzoyl)-5-methoxy-2-methyl-1H-indole-3-acetoxy]-ethyl}-tert. butylamine This compound was prepared from 4-amino-3-bromo-5-(N-ethyl-cyclohexylaminomethyl)-benzoyl chloride hydrochloride and N-{2-[1-(4-chlorobenzoyl)-5-methoxy-2-methyl-1H-indole-3-acetoxy]-ethyl}-N-(2-hydroxyethyl)-tert. butylamine analogous to Example 10. Foam.

$C_{43}H_{54}BrClN_4O_6$ (838.3): Calc.: C-61.61%; H-6.49%; Br-9.53%; Cl-4.23%; N-6.68%; Found: C-61.50%; H-6.63%; Br-9.69%; Cl-4.30%; N-6.53%.

Example 92

N-{2-[4-Amino-3-bromo-5-(N-ethyl-cyclohexylaminomethyl)benzoyloxy]-ethyl}-N-{2-[1-(4-chlorobenzoyl)-5-methoxy-2-methyl-1H-indole-3-acetoxy]-ethyl}-benzylamine This compound was prepared from 1-(4-chlorobenzoyl)-5-methoxy-2-methyl-1H-indole-3-acetic acid and N-{2-[4-amino-3-bromo-5-(N-ethyl-cyclohexylaminomethyl)benzoyloxy]-ethyl}-N-(2-hydroxyethyl)-benzylamine analogous to Example 4. Oil.

IR-spectrum (methylene chloride):
Amide-CO: 1675 cm$^{-1}$
Ester-CO: 1700 and 1730 cm$^{-1}$
O-methyl: 2840 cm$^{-1}$
N-alkyl: 2940 cm$^{-1}$
UV-spectrum (ethanol): λ max 235 nm (shoulder), 290 nm.

Example 93

N-{2-[4-Amino-3-bromo-5-(N-ethyl-cyclohexylaminomethyl)benzoyloxy]-ethyl}-N-{2-[1-(4-chlorobenzoyl)-5-methoxy-2-methyl-1H-indole-3-acetoxy]-ethyl}-aniline This compound was prepared from 1-(4-chlorobenzoyl)-5-methoxy-2-methyl-1H-indole-3-acetic acid and N-{2-[4-amino-3-bromo-5-(N-ethyl-cyclohexylaminomethyl)-benzoyloxy]ethyl}-N-(2-hydroxyethyl)-aniline analogous to Example 4. Oil.

$C_{45}H_{50}BrClN_4O_6$ (858.3): Calc.: C-62.97%; H-5.87%; Br-9.31%; Cl-4.13%; N-6.53%; Found: C-62.90%; H-6.11%; Br-9.54%; Cl-4.23%; N-6.59%.

Example 94

N-{2-[4-Amino-3-bromo-5-(N-ethyl-cyclohexylaminomethyl)benzoyloxy]-ethyl}-N-{2-[2-[(2,6-dichlorophenyl)-amino]phenylacetoxy]-ethyl}-methylamine This compound was prepared from sodium 2-[(2,6-dichlorophenyl)-amino]-phenyl-acetate and N-{2-[4-amino-3-bromo-5-(N-ethyl-cyclohexylaminomethyl)-benzoyloxy]-ethyl}-N-(2-chloroethyl)-methylamine analogous to Example 8. Oil.

$C_{35}H_{43}BrCl_2N_4O_4$ (734.6): Calc.: C-57.23%; H-5.90%; Br-10.87%; Cl-9.65%; N-7.62%; Found: C-57.60%; H-6.12%; Br-10.58%; Cl-9.39%; N-7.54%.

Example 95

N-{2-[4-Amino-3-bromo-5-(N-ethyl-cyclohexylaminomethyl)benzoyloxy]-ethyl}-N-{2-[2-[(2,6-dichlorophenyl)-amino]phenylacetoxy]-ethyl}-ethylamine This compound was prepared from sodium 2-[(2,6-dichlorophenyl)-amino]-phenyl-acetate and N-{2-[4-amino-3-bromo-5-(N-ethyl-cyclohexylaminomethyl)-benzoyloxy]ethyl}-N-(2-chloroethyl)-ethylamine analogous to Example 8. The dihydrochloride was obtained as an amorphous powder.

IR-spectrum (methylene chloride):
Ester-CO: 1720 and 1740 cm$^{-1}$
N-alkyl: 2940 cm$^{-1}$
UV-spectrum (ethanol): λ max 285 nm.

Example 96

N-{2-[4-Amino-3-bromo-5-(N-ethyl-cyclohexylaminomethyl)benzoyloxy]-ethyl}-N-{2-[2-[(2,6-dichlorophenyl)-amino]phenylacetoxy]-ethyl}-n-propylamine This compound was prepared from sodium 2-[(2,6-dichlorophenyl)-amino]-phenyl-acetate and N-{2-[4-amino-3-bromo-5-(N-ethyl-cyclohexylaminomethyl)-benzoyloxy]-ethyl}N-(2-chloroethyl)-n-propylamine analogous to Example 8. Oil.

$C_{37}H_{47}BrCl_2N_4O_4$ (762.6): Calc.: C-58.27%; H-6.21%; Br-10.48%; Cl-9.30%; N-7.35%; Found: C-58.50%; H-6.45%; Br-10.58%; Cl-9.31%; N-7.06%.

Example 97

N-{2-[4-Amino-3-bromo-5-(N-ethyl-cyclohexylaminomethyl)benzoyloxy]-ethyl}-N-{2-[2-[(2,6-dichlorophenyl)-amino]phenylacetoxy]-ethyl}-isopropylamine This compound was prepared from sodium 2-[(2,6-dichlorophenyl)-amino]-phenyl-acetate and N-{2-[4-amino-3-bromo-5-(N-ethyl-cyclohexylaminomethyl)-benzoyloxy]-ethyl}-N-(2-chloroethyl)-isopropylamine analogous to Example 8. Oil.

$C_{37}H_{47}BrCl_2N_4O_4$ (762.6): Calc.: C-58.27%; H-6.21%; Br-10.48%; Cl-9.30%; N-7.35%; Found: C-58.40%; H-6.37%; Br-10.22%; Cl-9.05%; N-7.08%.

Example 98

N-{2-[4-Amino-3-bromo-5-(N-ethyl-cyclohexylaminomethyl)benzoyloxy]-ethyl}-N-{2-[2-[(2,6-dichlorophenyl)-amino]phenylacetoxy]-ethyl}-n-butylamine This compound was prepared from 2-[(2,6-dichlorophenyl)-amino]-phenyl-acetic acid and N-{2-[4-amino-3-bromo-5-(N-ethyl-cyclohexylaminomethyl)-benzoyloxy]-ethyl}N-(2-hydroxyethyl)-n-butylamine analogous to Example 4. Oil.

IR-spectrum (methylene chloride):
Ester-CO: 1710 cm$^{-1}$
N-alkyl: 2935 cm$^{-1}$
UV-spectrum (ethanol): λ max 230 nm (shoulder), 284 nm.

Example 99

N-{2-[4-Amino-3-bromo-5-(N-ethyl-cyclohexylaminomethyl)benzoyloxy]-ethyl}-N-{2-[2-[(2,6-dichlorophenyl)-amino]phenylacetoxy]-ethyl}-benzylamine This compound was prepared from 2-[(2,6-dichlorophenyl)-amino]-phenyl-acetic acid and N-{2-[4-amino-3-bromo-5-(N-ethyl-cyclohexylaminomethyl)-benzoyloxy]-ethyl}-N-(2-hydroxyethyl)-benzylamine analogous to Example 4. Oil.

IR-spectrum (methylene chloride):
Ester-CO: 1710 cm$^{-1}$
N-alkyl: 2935 cm$^{-1}$
UV-spectrum (ethanol): λ max 235 nm (shoulder), 280 nm.

Example 100

N-{2-[4-Amino-3-bromo-5-(N-ethyl-cyclohexylaminomethyl)benzoyloxy]-ethyl}-N-{2-[2-[(2,6-dichlorophenyl)-amino]phenylacetoxy]-ethyl}-aniline This compound was prepared from 2-[(2,6-dichlorophenyl)-amino]-phenyl-acetic acid and N-{2-[4-amino-3-bromo-5-(N-ethyl-cyclohexylaminomethyl)-benzoyloxy]-ethyl}-N-(2-hydroxyethyl)-aniline analogous to Example 4. Foam.

IR-spectrum (methylene chloride):
Ester-CO: 1710 cm$^{-1}$
N-alkyl: 2935 cm$^{-1}$
UV-spectrum (ethanol): λ max 250 nm, 280 nm.

Example 101

N-{2-[4-Amino-3-bromo-5-(N-ethyl-cyclohexylaminomethyl)benzoyloxy]-ethyl}-N-[2-(3-benzoyl-α-methyl-phenylacetoxy)ethyl]-amine This compound was prepared from 3-benzoyl-α-methylphenyl-acetic acid chloride and N-{2-[4-amino-3bromo-5-(N-ethyl-cyclohexylaminomethyl)-benzoyloxy]-ethyl}-N-(2-hydroxyethyl)-amine hydrochloride analogous to Example 5. The dihydrochloride was obtained as an amorphous powder.

$C_{36}H_{44}BrN_2O_5$ x 2 HCl (751.6): Calc.: C-57.53%; H-6.17%; Br-10.63%; Cl-9.43%; N-5.59%; Found: C-57.25%; H-6.43%; Br-10.38%; Cl-9.18%; N-5.46%.

Example 102

N-[2-[4-Amino-3-bromo-5-(N-ethyl-cyclohexylaminomethyl)benzoyloxy]-ethyl}-N-[2-(3-benzoyl-α-methyl-phenylacetoxy)ethyl]-methylamine This compound was prepared from 3-benzoyl-α-methylphenyl-acetic acid imidazolide and N-{2-[4-amino-3-bromo-5-(N-ethyl-cyclohexylaminomethyl)-benzoyloxy]-ethyl}-N-(2-hydroxyethyl)-methylamine analogous to Example 3. The dihydrochloride was obtained as an amorphous powder.

$C_{37}H_{46}BrN_3O_5$ x 2 HCl (756.6): Calc.: C-58.04%; H-6.32%, Br-10.44%; Cl-9.26%; N-5.48%; Found: C-57.90%; H-6.26%; Br-11.11%; Cl-8.96%; N-5.35%.

Example 103

N-{2-[4-Amino-3-bromo-5-(N-ethyl-cyclohexylaminomethyl)benzoyloxy]-ethyl}-N [2-(3-benzoyl-α-methyl-phenylacetoxy)ethyl]-ethylamine This compound was prepared from 3-benzoyl-α-methylphenyl-acetic acid imidazolide and N-{2-[4-amino-3-bromo-5-(N-ethyl-cyclohexylaminomethyl)-benzoyloxy]-ethyl}-N-2-hydroxyethyl)-ethylamine analogous to Example 3. The dihydrochloride was obtained as an amorphous powder.

$C_{38}H_{48}BrN_3O_5$ x 2 HCl (779.6): Calc.: C-58.54%; H-6.46%; Br-10.25%; Cl-9.10%; N-5.39%; Found: C-58.20%; H-6.54%; Br-10.18%; Cl-9.06%; N-5.38%.

Example 104

N-{2-[4-Amino-3-bromo-5-(N-ethyl-cyclohexylaminomethyl)benzoyloxy]-ethyl}-N-[2-(3-benzoyl-α-methyl-phenylacetoxy)ethyl]-n-propylamino This compound was prepared from 3-benzoyl-α-methylphenyl-acetic acid imidazolide and N-{2-[4-amino-3-bromo-5-(N-ethyl-cyclohexylaminomethyl)-benzoyloxy]-ethyl}-N-(2-hydroxyethyl)-n-propylamine in boiling tetrahydrofuran, analogous to Example 3. Oil.

IR-spectrum (methylene chloride):
Ketone-CO: 1650 cm$^{-1}$
Ester-CO: 1690 and 1720 cm$^{-1}$
N-alkyl: 2850 cm$^{-1}$
UV-spectrum (ethanol): λ max 253 nm, 290 nm.

Example 105

N-{2-[4-Amino-3-bromo-5-(N-ethyl-cyclohexylaminomethyl)benzoyloxy]-ethyl}-N-[2-(3-benzoyl-α-methyl-phenylacetoxy)ethyl]-isopropylamine This compound was prepared from 3-benzoyl-α-methylphenyl-acetic acid imidazolide and N-{2-[4-amino-3-bromo-5-(N-ethyl-cyclohexylaminomethyl)-benzoyloxy]-ethyl}-N-(2-hydroxyethyl)-isopropylamine analogous to Example 3. Oil.

$C_{39}H_{50}BrN_3O_5$ (720.8): Calc.: C-64.99%; H-6.99%; Br-11.09%; N-5.83%; Found: C-64.80%; H.7.28%; Br-10.95%; N-5.59%.

Example 106

N-{2-[4-Amino-3-bromo-5-(N-ethyl-cyclohexylaminomethyl)benzoyloxy]-ethyl}-N-[2-(3-benzoyl-α-methyl-phenylacetoxy)ethyl]-n-butylamine This compound was prepared from 3-benzoyl-α-methylphenyl-acetic acid and N-{2-[4-Amino-3-bromo-5-(N-ethylcyclohexylaminomethyl)-benzoyloxy]-ethyl}-N-(2-hydroxyethyl)-n-butylamine analogous to Example 4. Oil.

IR-spectrum (methylene chloride):
Ketone-CO: 1660 cm$^{-1}$
Ester-CO: 1705 and 1730 cm$^{-1}$
N-alkyl: 2935 cm$^{-1}$
UV-spectrum (ethanol): λ max 255 nm, 290 nm.

Example 107

N-{2-[4-Amino-3-bromo-5-(N-ethyl-cyclohexylaminomethyl)benzoyloxy]-ethyl}-N-[2-(3-benzoyl-α-methyl-phenylacetoxy)ethyl]-tert. butylamine This compound was prepared from 3-benzoyl-α-methylphenyl-acetic acid and N-{2-[4-amino-3-bromo-5-(N-ethylcyclohexylaminomethyl)-benzoyloxy]-ethyl}-N-(2-hydroxyethyl)tert. butylamine analogous to Example 4. The dihydrochloride was obtained as an amorphous powder.

IR-spectrum (methylene chloride):
Ketone-CO: 1640 cm$^{-1}$
Ester-CO: 1710 and 1730 cm$^{-1}$
N-alkyl: 2940 cm$^{-1}$
UV-spectrum (ethanol): λ max 256 nm, 280 nm.

Example 108

N-{2-[4-Amino-3-bromo-5-(N-ethyl-cyclohexylaminomethyl)benzoyloxy]-ethyl}-N-[2-(3-benzoyl-α-methyl-phenylacetoxy)ethyl]-benzylamine This compound was prepared from 3-benzoyl-α-methylphenyl-acetic acid and N-{2-[4-amino-3-bromo-5-(N-ethylcyclohexylaminomethyl)-benzoyloxy]-N-(2-hydroxyethyl)benzylamine analogous to Example 4. Oil.

IR-spectrum (methylene chloride):
Ketone-CO: 1660 cm$^{-1}$
Ester-CO: 1710 and 1730 cm$^{-1}$
N-alkyl: 2940 cm$^{-1}$
UV-spectrum (ethanol): λ max 252 nm, 288 nm.

Example 109

N-{2-[4-Amino-3-bromo-5-(N-ethyl-cyclohexylaminomethyl)benzoyloxy]-ethyl}-N-[2-(3-benzoyl-α-methyl-phenylacetoxy)ethyl]-aniline This compound was prepared from 3-benzoyl-α-methylphenyl-acetic acid and N-{2-[4-amino-3-bromo-5-(N-ethylcyclohexylaminomethyl)-benzoyloxy]-ethyl}-N-(2-hydroxyethyl)aniline analogous to Example 4. Oil IR-spectrum (methylene chloride):
Ketone-CO: 1660 cm$^{-1}$
Ester-CO: 1710 and 1735 cm$^{-1}$
N-alkyl: 2940 cm$^{-1}$
UV-spectrum (ethanol): λ max 250 nm, 290 nm.

Example 110

N-{2-[4-Amino-3-bromo-5-(N-ethyl-cyclohexylaminomethyl)benzoyloxy]-ethyl}-N-{2-[(+)-6-methoxy-α-methyl-2-naphthaline-acetoxy]-ethyl}-amine This compound was prepared from (+)-6-methoxy-α-methyl-2-naphthaline-acetic acid chloride and N-{2-[4-amino-3-bromo-5-(N-ethyl-cyclohexylaminomethyl)-benzoyloxy]ethyl}-N-(2-hydroxyethyl)-amine hydrochloride analogous to Example 5. The dihydrochloride was obtained as an amorphous powder.

IR-spectrum (methylene chloride):
Ester-CO: 1720 and 1740 cm$^{-1}$
O-methyl: 2850 cm$^{-1}$
N-alkyl: 2930 cm$^{-1}$ UV-spectrum (ethanol): λ max 221 nm, 282 nm.

Example 111

N-{2-[4-amino-3-bromo-5-(N-ethyl-cyclohexylaminomethyl)benzoyloxy]-ethyl}-N-{2-[(+)-6-methoxy-α-methyl-2-naphthaline-acetoxy]-ethyl}-methylamine This compound was prepared from (+)-6-methoxy-α-methyl-2-naphthaline-acetic acid imidazolide and N-{2-[4-amino-3-bromo-5-(N-ethyl-cyclohexylaminomethyl)-benzoyloxy]ethyl}-N-(2-hydroxyethyl)-methylamine analogous to Example 3. The dihydrochloride was obtained as an amorphous powder.

IR-spectrum (potassium bromide):
Ester-CO: 1720 and 1730 cm$^{-1}$
O-methyl: 2860 cm$^{-1}$
N-alkyl: 2940 cm$^{-1}$
UV-spectrum (ethanol): λ max 233 nm, 285 nm.

Example 112

N-{2-[4-Amino-3-bromo-5-(N-ethyl-cyclohexylaminomethyl)benzoyloxy]-ethyl}-N-{2-[(30)-6-methoxy-α-methyl-2-naphthaline-acetoxy]-ethyl}-ethylamine This compound was prepared from (+)-6-methoxy-α-methyl-2-naphthaline-acetic acid imidazolide and N-{2-[4-amino-3-bromo-5-(N-ethyl-cyclohexylaminomethyl)-benzoyloxy]ethyl}-N-(2-hydroxyethyl)-ethylamine analogous to Example 3. The dihydrochloride was obtained as an amorphous powder.

$C_{36}H_{48}BrN_3O_5$ x 2 HCl (755.7): Calc.: C-57.22%; H-6.67%; Br-10.58%; Cl-9.38%; N-5.56%; Found: C-57.00%; H-6.78%; Br-10.62%; Cl-9.47%; N-5.37%.

Example 113

N-{2-[4-Amino-3-bromo-5-(N-ethyl-cyclohexylaminomethyl)benzoyloxy]-ethyl}-N-{2-[(+)-6-methoxy-α-methyl-2-naphthaline-acetoxy]-ethyl}-n-propylamine This compound was prepared from (+)-6-methoxy-α-methyl-2-naphthaline-acetic acid imidazolide and N-{2-[4-amino-3-bromo-5-(N-ethyl-cyclohexylaminomethyl)-benzoyloxy]ethyl}-N-(2-hydroxyethyl)-n-propylamine in boiling tetrahydrofuran, analogous to Example 3. Oil.

$C_{37}H_{50}BrN_3O_5$ (696.7): Calc.: C-63.78%; H-7.23%; Br-11.47%; N-6.03%; Found: C-63.90%; H-7.51%; Br-11.54%; N-5.97%.

Example 114

N-{2-[4-Amino-3-bromo-5-(N-ethyl-cyclohexylaminomethyl)benzoyloxy]-ethyl}-N-{2-[(+)-6-methoxy-α-methyl-2-naphthaline-acetoxy]-ethyl}-isopropylamine This compound was prepared from (+)-6-methoxy-α-methyl-2-naphthaline-acetic acid imidazolide and N-{2-[4-amino-3-bromo-5-(N-ethyl-cyclohexylaminomethyl)-benzoyloxy]-ethyl}-N-(2-hydroxyethyl)-isopropylamine analogous to Example 3. Oil.

$C_{37}H_{50}BrN_3O_5$ (696.7): Calc.: C-63.78%; H-7.23%; Br-11.47%; N-6.03%; Found: C-63.80%; H-7.40%; Br-11.40%; N-6.00%.

Example 115

N-{2-[4-Amino-3-bromo-5-(N-ethyl-cyclohexylaminomethyl)benzoyloxy]-ethyl}-N-{2-[α-methyl-4-(2-methylpropyl)-phenylacetoxy]-ethyl}-amine This compound was prepared from α-methyl-4-(2-methylpropyl)-phenyl-acetic acid chloride and N-{2-[4-amino-3-bromo-5-(N-ethyl-cyclohexylaminomethyl)-benzoyloxy]ethyl}-N-(2-hydroxyethyl)-amine hydrochloride analogous to Example 5. The dihydrochloride was obtained as an amorphous powder.

IR-spectrum (methylene chloride):
Ester-CO: 1720 and 1730 cm$^{-1}$
N-alkyl 2950 cm$^{-1}$
UV-spectrum (ethanol): λ max 218 nm, 284 nm.

Example 116

N-{2-[4-Amino-3-bromo-5-(N-ethyl-cyclohexylaminomethyl)benzoyloxy]-ethyl}-N-{2-[α-methyl-4-(2-methylpropyl)-phenylacetoxy]-ethyl}-methylamine This compound was prepared from α-methyl-4-(2-methylpropyl)-phenyl-acetic acid imidazolide and N-{2-[4-amino-3-bromo-5-(N-ethyl-cyclohexylaminomethyl)-benzoyloxy]ethyl}-N-(2-hydroxyethyl)-methylamine analogous to Example 3. Oil.

$C_{34}H_{50}BrN_3O_4$ (644.7): Calc.: C-63.34%; H-7.82%; Br-12.40%; N-6.52%; Found: C-63.10%; H-7.84%; Br-12.10%; N-6.59%.

Example 117

N-{2-[4-Amino-3-bromo-5-(N-ethyl-cyclohexylaminomethyl)benzoyloxy]-ethyl}-N-{2-[α-methyl-4-(2-methylpropyl)phenyl-acetoxy]-ethyl}-n-propylamine This compound was prepared from α-methyl-4-(2-methylpropyl)-phenyl-acetic acid imidazolide and N-{2-[4-amino-3-bromo-5-(N-ethyl-cyclohexylaminomethyl)-benzoyloxy]ethyl}-N-(2-hydroxyethyl)-n-propylamine analogous to Example 3. Oil.

IR-spectrum (methylene chloride):
Ester-CO: 1700 and 1725 cm$^{-1}$
N-alkyl: 2820 cm$^{-1}$
UV-spectrum (ethanol): λ max 230 nm (shoulder), 294 nm.

Example 118

N-{2-[4-Amino-3-bromo-5-(N-ethyl-cyclohexylaminomethyl)benzoyloxy]-ethyl}-N-{2-[α-methyl-4-(2-methylpropyl)-phenylacetoxy]-ethyl}-isopropylamine This compound was prepared from α-methyl-4-(2-methylpropyl)-phenyl-acetic acid imidazolide and N-{2-[4-amino-3-bromo-5-(N-ethyl-cyclohexylaminomethyl)-benzoyloxy]ethyl}-N-(2-hydroxyethyl)-isopropylamine in boiling tetrahydrofuran, analogous to Example 3. Oil $C_{36}H_{54}BrN_3O_4$ (672.8): Calc.: C-64.27%; H-8.09%; Br-11.88%; N-6.25%; Found: C-64.50%; H-8.28%; Br-12.05%; N-6.32%.

Example 119

N-[2-(4-Amino-3-bromo-5-diethylaminomethyl-benzoyloxy)ethyl]-N-{2-[1-(4-chlorobenzoyl)-5-methoxy-2-methyl-1H-indole-3-acetoxy]-ethyl}-methylamine This compound was prepared from 1-(4-chlorobenzoyl)-5-methoxy-2-methyl-1H-indole-3-acetic acid chloride and N-[2-(4-amino-3-bromo-5-diethylaminomethyl-benzoyloxy)ethyl]-N-(2-hydroxyethyl)-methylamine analogous to Example 5. Oil.

IR-spectrum (methylene chloride):
Amide-CO: 1690 cm$^{-1}$
Ester-CO: 1705 and 1735 cm$^{-1}$
UV-spectrum (ethanol): λ max 230 nm (shoulder), 290 nm.

Example 120

2-[4-Amino-3-bromo-5-(N-ethyl-cyclohexylaminomethyl)benzoyloxy]-2'-[1-(4-chlorobenzoyl)-5-methoxy-2-methyl-1H-indole-3-acetoxy]-diethyloxide This compound was prepared from 4-amino-3-bromo-5-(N-ethyl-cyclohexylaminomethyl)-benzoyl chloride hydrochloride and 2-[1-(4-chlorobenzoyl)-5-methoxy-2-methyl-1H-indole-3-acetoxy]-2'-hydroxydiethyloxide analogous to Example 10. Oil.

IR-spectrum (methylene chloride):
Amide-CO: 1690 cm$^{-1}$
Ester-CO: 1710 and 1735 cm$^{-1}$
O-methyl: 1850 cm$^{-1}$
N-alkyl: 2920 cm$^{-1}$
UV-spectrum (ethanol): λ max 230 nm (shoulder), 295 nm.

Example 121

2-[4-Amino-3-bromo-5-(N-ethyl-cyclohexylaminomethyl)benzoyloxy]-2'-[(+)-6-methoxy-α-methyl-2-naphthalineacetoxy]-diethyloxide This compound was prepared from 2-[4-amino-3-bromo-5-(N-ethyl-cyclohexylaminomethyl)-benzoyloxy]-2'-hydroxydiethyloxide and (+)-6-methoxy-α-methyl-2-maphthalineacetic acid imidazolide analogous to Example 3. Oil.

$C_{34}H_{43}BrN_2O_6$ (655.6): Calc.: C-62.28%; H-6.61%; Br-12.19%; N-4.27%; Found: C-62.20%; H-6.78%; Br-12.10%; N-4.09%.

Example 122

2-[4-Amino-3-bromo-5-(N-ethyl-cyclohexylaminomethyl)benzoyloxy]-2'-{2-[(2,6-dichlorophenyl)-amino]-phenylacetoxy}-diethyloxide This compound was prepared from 2-[4-amino-3-bromo-5-(N-ethyl-cyclohexylaminomethyl)-benzoyloxy]-2'-chlorodiethyloxide and sodium 2-[(2,6-dichlorophenyl)amino]-phenyl acetate analogous to Example 8. The hydrochloride was obtained as an amorphous powder.

IR-spectrum (methylene chloride):
Ester-CO: 1710 and 1720 cm$^{-1}$
N-alkyl 2950 cm$^{-1}$
UV-spectrum (ethanol): λ max 283 nm.

Example 123

2-[4-Amino-3-bromo-5-(N-ethyl-cyclohexylaminomethyl)benzoyloxy]-2'-(3-benzoyl-α-methyl-phenyl-acetoxy)diethyloxide This compound was prepared from 2-[4-amino-3-bromo-5-(N-ethyl-cyclohexylaminomethyl)-benzoyloxy]-2'-hydroxydiethyloxide and 3-benzoyl-α-methyl-phenyl-acetic acid imidazolide analogous to Example 3. Oil.

$C_{36}H_{43}BrN_2O_6$ (679.7): Calc.: C-63.62%; H-6.38%; Br-11.76%; N-4.12%; Found: C-63.40%; H-6.58%; Br-11.35%; N-4.03%.

Example 124

2-[4-Amino-3-bromo-5-(N-ethyl-cyclohexylaminomethyl)benzoyloxy]-2'-[α-methyl-4-(2-methylpropyl)-phenyl-acetoxy]diethyloxide This compound was prepared from 2-[4-amino-3-bromo-5-(N-ethyl-cyclohexylaminomethyl)-benzoyloxy]-2'-hydroxy-diethyloxide and α-methyl-4-(2-methylpropyl)-phenylacetic acid imidazolide analogous to Example 3. Oil $C_{33}H_{47}BrN_2O_5$ (631.7): Calc.: C-62.75%; H-7.50%; Br-12.65%; N-4.44%; Found: C-62.60%; H-7.58%; Br-12.90%; N-4.54%.

Example 125

2-[4-Amino-3-bromo-5-(N-ethyl-cyclohexylaminomethyl)benzoyloxy]-2'-[1-(4-chlorobenzoyl)-5-methoxy-2-methyl-1H-indole-3-acetoxy]-diethylsulfide This compound was prepared from 2-[4-amino-3-bromo-5-(N-ethyl-cyclohexylaminomethyl)-benzoyloxy]-2'-hydroxydiethylsulfide and 1-(4-chlorobenzoyl)-5-methoxy-2-methyl-1H-indole-3-acetic acid chloride analogous to Example 5. The hydrochloride was obtained as an amorphous powder.

$C_{39}H_{45}BrClN_3O_6S$ x HCl (835.7): Calc.: C-56.05%; H-5.54%; Br-9.56%; Cl-8.49%; N-5.02%; Found: C-56.00%; H-5.80%; Br-9.74%; Cl-8.69%; N-4.84%.

Example 126

2-[4-Amino-3-bromo-5-(N-ethyl-cyclohexylaminomethyl)-benzoyloxy]-2'-[(+)-6-methoxy-α-methyl-2-naphthalineacetoxy]-diethylsulfide This compound was prepared from 2-[(4-amino-3-bromo-5-(N-ethyl-cyclohexylaminomethyl)-benzoyloxy]-2'-hydroxy-diethylsulfide and (+)-6-methoxy-α-methyl-2-naphthaline-acetic acid imidazolide analogous to Example 3. Oil.

IR-spectruk (methylene chloride):
Ester-CO: 1705 and 1730 cm$^{-1}$
O-methyl: 2860 cm$^{-1}$
N-alkyl: 2930 cm$^{-1}$
UV-spectrum (ethanol): λ max 233 nm, 298 nm.

Example 127

2-[4-Amino-3-bromo-5-(N-ethyl-cyclohexylaminomethyl)-benzoyloxy]-2'-{2-[(2,6-dichlorophenyl)-amino]-phenyl-acetoxy}-diethylsulfide This compound was prepared from 2-[4-amino-3-bromo-5-(N-ethyl-cyclohexylaminomethyl)-benzoyloxy]-2'-chlorodiethylsulfide and sodium 2-[(2,6-dichlorophenyl)-amino]-phenyl-acetate analogous to Example 8. Oil.

$C_{34}H_{40}BrCl_2N_3O_4S$ (737.6): Calc.: C-55.36%; H-5.47%; Br-10.83%; Cl-9.61%; N-5.69%; S-4.35%; Found: C-55.20%; H-5.90%; Br-10.65%; Cl-9.47%; N-5.59%; S-4.31%.

Example 128

2-[4-Amino-3-bromo-5-(N-ethyl-cyclohexylaminomethyl)-benzoyloxy]-2'-(3-benzoyl-α-methyl-phenyl-acetoxy)-diethylsulfide This compound was prepared from 2-[4-amino-3-bromo-5-(N-ethyl-cyclohexylaminomethyl)-benzoyloxy]-2'-hydroxydiethylsulfide and 3-benzoyl-α-methyl-phenyl acetic acid imidazolide analogous to Example 3. Oil.

$C_{36}H_{43}BrN_2O_5S$ (695.7): Calc.: C-62.15%; H-6.23%; Br-11.49%; N-4.02%; S-4.60%; Found: C-62.20%; H-6.50%; Br-11.25%; N-3.87%; S-4.72%.

Example 129

2-[4-Amino-3-bromo-5-(N-ethyl-cyclohexylaminomethyl)-benzoyloxy]-2'-[2-fluoro-α-methyl-(1,1'-biphenyl)-4-acetoxy]-diethylsulfide This compound was prepared from 2-[4-amino-3-bromo-5-(N-ethyl-cyclohexylaminomethyl)-benzoyloxy]-2'-hydroxydiethylsulfide and 2-fluoro-α-methyl-(1,1'-biphenyl)-4-acetic acid analogous to Example 4. Oil.

IR-spectrum (methylene chloride):
Ester-CO: 1710 and 1735 cm$^{-1}$
N-alkyl: 2935 cm$^{-1}$
UV-spectrum (ethanol): max 232 nm, 288 nm.

Example 130

2-[4-Amino-3-bromo-5-(N-ethyl-cyclohexylaminomethyl)-benzoyloxy]-2'-[2-fluoro-α-methyl-(1,1'-biphenyl)-4-acetoxy]-diethyloxide This compound was prepared from 2-[4-amino-3-bromo-5-(N-ethyl-cyclohexylaminomethyl)-benzoyloxy]-2'-hydroxy-diethyloxide and 2-fluoro-α-methyl-(1,1'-biphenyl)-4-acetic acid analogous to Example 4. Oil.

$C_{35}H_{42}BrFN_2O_5$ (669.7): Calc.: C-62.78%; H-6.32%; Br-11.93%; N-4.18%; Found: C-63-04%; H-6.48%; BR-11.90%; N-4.07%.

Example 131

2-[4-Amino-3-bromo-5-(N-ethyl-cyclohexylaminomethyl)-benzoyloxy]-2'-{2-[(2,6-dichlorophenyl)-amino]-phenylacetoxy}-diethylsulfoxide.

This compound was prepared from 2-[4-amino-3-bromo-5-(N-ethyl-cyclohexylaminomethyl)-benzoyloxy]-2'-{2-[(2,6-dichlorophenyl)-amino]-phenyl-acetoxy}-diethylsulfide with hydrogen peroxide analogous to Example 14. Foam.

IR-spectrum (methylene chloride):
Sulfoxide 1040 cm$^{-1}$
Ester-CO: 1710 cm$^{-1}$
N-alkyl: 2930 cm$^{-1}$
UV-spectrum (ethanol): λ max 300 nm.

Example 132

2-[4-Amino-3-bromo-5-(N-ethyl-cyclohexylaminomethyl)-benzoyloxy]-2'-{2-[(2,6-dichlorophenyl)-amino]-phenylacetoxy}-diethylsulfone This compound was prepared from 2-[4-amino-3-bromo-5-(N-ethyl-cyclohexylaminomethyl)-benzoyloxy]-2'-{2-[(2,6-dichlorophenyl)-amino]-phenyl-acetoxy}-diethylsulfide with hydrogen peroxide analogous to Example 15. Foam.

$C_{34}H_{40}BrCl_2N_3O_6S$ (769.6): Calc.: C-53.06%; H-5.24%; Br-10.38%; Cl-9.21%; N-5.46%; Found: C-53.01%; H-5.35%; Br-10.56%; Cl-9.33%; N-5.34%.

Example 133

2-(4-Amino-3-bromo-5-diethylaminomethyl-benzoyloxy)-2'-{2-[(2,6-dichlorophenyl)-amino]-phenyl-acetoxy}-diethyloxide This compound was prepared from 2'-{2-[(2,6-dichlorophenyl)-amino]-phenyl-acetoxy}-2-hydroxy-diethyloxide and 4-amino-3-bromo-5-diethylaminomethyl-benzoyl chloride hydrochloride analogous to Example 7. Oil.

IR-spectrum (methylene chloride):
Ester-CO: 1710 cm$^{-1}$
N-alkyl: 2960 cm$^{-1}$
UV-spectrum (ethanol): λ max 230 nm (shoulder), 282 nm.

Example 134

N-{2-[4-Amino-3-bromo-5-(N-ethyl-cyclohexylaminomethyl)-benzoyloxy]-ethyl}-N'-{2-[1-(4-chlorobenzoyl)-5-methoxy-2-methyl-1H-indole-3-acetoxy]-ethyl}-piperazine This compound was prepared from N-{2-[4-amino-3-bromo-5-(N-ethyl-cyclohexylaminomethyl)-benzoyloxy]-ethyl}-N'-(2-hydroxyethyl)-piperazine and 1-(4-chlorobenzoyl)-5-methoxy-2-methyl-1H-indole-3-acetic acid imidazolide analogous to Example 3. Oil.

$C_{43}H_{53}BrClN_5O_6$ (851.3): Calc.: C-60.67%; H-6.28%; Br-9.39%; Cl-4.16%; N-8.23%; Found: C-60.50%; H-6.65%; Br-9.22%; Cl-4.09%; N-8.10%.

Example 135

N-{3-[4-Amino-3-bromo-5-(N-ethyl-cyclohexylaminomethyl)-benzoyloxy]-propyl}-N'-{2-[1-(4-chlorobenzoyl)-5-methoxy-2-methyl-1H-indole-3-acetoxy]-ethyl}-piperazine This compound was prepared from N-{3-[4-amino-3-bromo-5-(N-ethyl-cyclohexylaminomethyl)-benzoyloxy]-propyl}-N'-(2-hydroxyethyl)-piperazine and 1-(4-chlorobenzoyl)-5-methoxy-2-methyl-1H-indole-3-acetic acid with dicyclohexylcarbodiimide, analogous to Example 4.

M.p. of the trihydrogen maleate: 120° C.

Example 136

N-{3-[4-Amino-3-bromo-5-(N-ethyl-cyclohexylaminomethyl)-benzoyloxy]-propyl}-N'-{2-[2-[(2,6-dichlorophenyl)-amino]-phenyl-acetoxy]-ethyl}-piperazine This compound was prepared from N-{3-[4-amino-3-bromo-5-(N-ethyl-cyclohexylaminomethyl)-benzoyloxy]-propyl}-N'-(2-hydroxyethyl)-piperazine and 2-[(2,6-dichlorophenyl)amino]-phenyl-acetic acid with dicyclohexyl-carbodiimide, analogous to Example 4.

M.p. of the trihydrogen maleate: beginning at 122° C. (decomp.).

Example 137

N-[3-(4-Amino-3-bromo-5-diethylaminomethyl-benzoyloxy)-propyl]-N'-{2-[1-(4-chlorobenzoyl)-5-methoxy-2-methyl-1H-indole-3-acetoxy]-ethyl}-piperazine This compound was prepared from N-[3-(4-amino-3-bromo-5-diethylaminomethyl-benzoyloxy-propyl]-N'-(2-hydroxyethyl)-piperazine and 1-(4-chlorobenzoyl)-5-methoxy-2-methyl-1H-indole-3-acetic acid with dicyclohexyl-carbodiimide analogous to Example 4.

M.p. of the trihydrogen maleate: beginning at 132° C. (decomp.).

Example 138

2-[4-Amino-3-bromo-5-(N-ethyl-cyclohexylaminomethyl)-benzoyloxy]-1-[1-(4-chlorobenzoyl)-5-methoxy-2-methyl-1H-indole-3-acetoxy}-n-propane This compound was prepared from 4-amino-3-bromo-5-(N-ethyl-cyclohexylaminomethyl)-benzoyl chloride and 1-[1-(4-chlorobenzoyl)-5-methoxy-2-methyl-1H-indole-3-acetoxy]-2-hydroxy-n-propane analogous to Example 7. Instead of pyridine, 4-dimethylamino-pyridine and instead of toluene, methylene chloride was used. Oil.

IR-spectrum (methylene chloride):
$NH_2$: 3420–3450 cm$^{-1}$
N-alkyl: 2925 cm$^{-1}$
$OCH_3$: 2850 cm$^{-1}$
Ester-CO: 1730 and 1720 cm$^{-1}$
Amide-CO: 1680 cm$^{-1}$
UV-spectrum (ethanol): λ max 230 nm, 290 nm.

Example 139

1-[4-Amino-3-bromo-5-(N-ethyl-cyclohexylaminomethyl)-benzoyloxy]-2-[(+)-6-methoxy-α-methyl-2-naphthalineacetoxy]-n-propane This compound was prepared from 1-[4-amino-3-bromo-5-(N-ethyl-cyclohexylaminomethyl)-benzoyloxy]-2-hydroxy-n-propane and (+)-6-methoxy-α-methyl-2-naphthaline-acetic acid imidazolide analogous to Example 1. Oil.

IR-spectrum (methylene chloride):
$NH_2$: 3430 cm$^{-1}$
N-alkyl: 2920 cm$^{-1}$
$OCH_3$: 2850 cm$^{-1}$
Ester-CO: 1730 and 1710 cm$^{-1}$
UV-spectrum (ethanol): λ mac 234 nm, 295 nm.

Example 140

2-[4-Amino-3-bromo-5-(N-ethyl-cyclohexylaminomethyl)-benzoyloxy]-3-[(+)-6-methoxy-α-methyl-2-naphthalineacetoxy]-n-butane This compound was prepared from 2-[4-amino-3-bromo-5-(N-ethyl-cyclohexylaminomethyl)-benzoyloxy]-3-hydroxy-n-butane and (+)-6-methoxy-α-methyl-2-naphthalineacetic acid imidazolide analogous to Example 1. Oil.

IR-spectrum (methylene chloride):
$NH_2$: 3430 cm$^{-1}$
N-alkyl: 2920 cm$^{-1}$
$OCH_3$: 2850 cm$^{-1}$
Ester-CO: 1730 and 1710 cm$^{-1}$
UV-spectrum (ethanol): λ max 234 nm, 295 nm.

Example 141

3-(4-Amino-3-bromo-5-diethylaminomethyl-benzoyloxy)-2-[1-(4-chlorobenzoyl)-5-methoxy-2-methyl-1H-indole-3-acetoxy]-n-propyl chloride This compound was prepared from 3-(4-amino-3-bromo-5-diethylaminomethyl-benzoyloxy)-2-hydroxy-n-propyl chloride and 1-(4-chlorobenzoyl)-5-methoxy-2-methyl-1H-indole-3-acetic acid imidazolide analogous to Example 1. Oil.

IR-spectrum (methylene chloride):
$NH_2$: 3440 cm$^{-1}$
Ester-CO: 1730 and 1705 cm$^{-1}$
UV-spectrum (ethanol): λ max 230 nm, 290–300 nm.

Example 142

2-[4-Amino-3-bromo-5-(N-ethyl-cyclohexylaminomethyl)-benzoyloxy]-3-[1-(4-chlorobenzoyl)-5-methoxy-2-methyl-1H-indole-3-acetoxy]-n-propyl chloride This compound was prepared from 4-amino-3-bromo-5-(N-ethyl-cyclohexylaminomethyl)-benzoic acid imidazolide and 3-[1-(4-chlorobenzoyl)-5-methoxy-2-methyl-1H-indole-3-acetoxy]-2-hydroxy-n-propyl chloride analogous to Example 11. Oil.

IR-spectrum (methylene chloride):
Ester-CO: 1710 and 1740 cm$^{-1}$
Amide-CO: 1670 cm$^{-1}$
UV-spectrum (ethanol): λ max 230 nm, 295 nm.

Example 143

Diethyl 2-[4-amino-3-bromo-5-(N-ethyl-cyclohexylaminomethyl)-benzoyl]-3-[1-(4-chlorobenzoyl)-5-methoxy-2-methyl-1H-indole-3-acetyl]-(+)-tartarate This compound was prepared from 4-amino-3-bromo-5-(N-ethyl-cyclohexylaminomethyl)-benzoyl chloride hydrochloride and diethyl 2-[1-(4-chlorobenzoyl)-5-methoxy-2-methyl-1H-indole-3-acetyl]-3-hydroxy-(+)-tartarate in tetrahydrofuran pyridine, analogous to Example 10. Foam.

IR-spectrum (methylene chloride):
Amide-CO: 1680 cm$^{-1}$
Ester-CO: 1720 and 1750 to 1760 cm$^{-1}$
O-methyl: 2850 cm$^{-1}$
N-alkyl: 2930 cm$^{-1}$
UV-spectrum (ethanol): λ max 237 (shoulder), 305 nm.

Example 144

2-[4-Amino-3-bromo-5-(N-ethyl-cyclohexylaminomethyl)-benzoyloxy]-1-acetoxy-3-[1-(4-chlorobenzoyl)-5-methoxy-2-methyl-1H-indole-3-acetoxy]-n-propane This compound was prepared from 4-amino-3-bromo-5-(N-ethyl-cyclohexylaminomethyl)-benzoyl chloride and 1-acetoxy-3-[1-(4-chlorobenzoyl)-5-methoxy-2-methyl-1H-indole-3-acetoxy-2-hydroxy-n-propane analogous to Example 10. Oil.

IR-spectrum (methylene chloride):
Ester-CO: 1710 and 1745 cm$^{-1}$
Amide-CO: 1675 cm$^{-1}$
UV-spectrum (ethanol): λ max 230 nm, 295 nm.

Example 145

2-[4-Amino-3-bromo-5-(N-ethyl-cyclohexylaminomethyl)-benzoyloxy]-1-octadecanoyloxy-3-[1-(4-chlorobenzoyl)-5-methoxy-2-methyl-1H-indole-3-acetoxy]-n-propane This compound was prepared from 4-amino-3-bromo-5-(N-ethyl-cyclohexylaminomethyl)-benzoyl chloride and 3-[1-(4-chlorobenzoyl)-5-methoxy-2-methyl-1H-indole-3-acetoxy]-1-octadecanoyloxy-2-hydroxy-n-propane analogous to Example 10. Oil.

$C_{56}H_{77}BrClN_3O_8$ (1035.6): Calc.: C-64.95%; H-7.49%; Br-7.72%; Cl-3.42%; N-4.06%; Found: C-64.70%; H-7.43%; Br-7.70%; Cl-3.40%; N-3.70%.

Example 146

2-[4-Amino-3-bromo-5-(N-ethyl-cyclohexylaminomethyl)-benzoyloxy]-1-octadecanoyloxy-3-[(+)-6-methoxy-α-methyl-2-naphthaline-acetoxy]-n-propane This compound was prepared from 4-amino-3-bromo-5-(N-ethyl-cyclohexylaminomethyl)-benzoic acid imidazolide and 3-[(+)-6-methoxy-α-methyl-2-naphthaline acetoxy]-1-octadecanoyloxy-2-hydroxy-n-propane analogous to Example 11. Oil.

$C_{51}H_{75}BrN_2O_7$ (908.1): Calc.: C-67.46%; H-8.32%; Br-8.80%; N-3.08%; Found: C-67.80%; H-8.36%; Br-8.63%; N-3.16%.

Example 147

1,2-Bis-[4-amino-3-bromo-5-(N-ethyl-cyclohexylaminomethyl)-benzoyloxy]-3-[(+)-6-methoxy-α-methyl-2-naphthaline-acetoxy]-n-propane This compound was prepared from 4-amino-3-bromo-5-(N-ethyl-cyclohexylaminomethyl)-benzoic acid imidazolide and 3-[(+)-6-methoxy-α-methyl-2-naphthaline-acetoxy]-1,2-dihydroxy-n-propane analogous to Example 11. Oil.

IR-spectrum (methylene chloride): Ester-CO 1710 and 1740 cm$^{-1}$

UV-spectrum (ethanol): λ max 243 nm, 302 nm.

Example 148

3-[4-Amino-3-bromo-5-(N-ethyl-cyclohexylaminomethyl)-benzoyloxy]-2-[1-(4-chlorobenzoyl)-5-methoxy-2-methyl-1H-indole-3-acetoxy]-1-hydroxy-n-propane This compound was prepared from 3-[4-amino-3-bromo-5-(N-ethyl-cyclohexylaminomethyl)-benzoyloxy]-1,2-epoxy-n-propane and 1-(4-chlorobenzoyl)-5-methoxy-2-methyl-1H-indole-3-acetic acid analogous to Example 6. Solid, amorphous substance.

IR-spectrum (methylene chloride):
Ester-CO: 1710 and 1735 cm$^{-1}$
Amide-CO: 1675 cm$^{-1}$ UV-spectrum (ethanol): λ max 230 nm, 297 nm.

Example 149

1-[4-Amino-3-bromo-5-(N-ethyl-cyclohexylaminomethyl)-benzoyloxy]-2-hydroxy-3-{2-[(2,6-dichlorophenyl)-amino]phenyl-acetoxy}-n-propane This compound was prepared from 4-amino-3-bromo-5-(N-ethyl-cyclohexylaminomethyl)-benzoic acid imidazolide and 1-{2-[(2,6-dichlorophenyl)-amino]-phenyl-acetoxy}-2,3-dihydroxy-n-propane analogous to Example 2.

M.p. of the hydrochloride: 87°–96° C.

Example 150

1-[4-Amino-3-bromo-5-(N-ethyl-cyclohexylaminomethyl)-benzoyloxy]-2-pentanoyloxy-3-[(+)-6-methoxy-α-methyl-2-naphthaline-acetoxy]-n-propane This compound was prepared from 1-[4-amino-3-bromo-5-(N-ethyl-cyclohexylaminomethyl)-benzoyloxy]-2-hydroxy-3-[(+)-6-methoxy-α-methyl-2-naphthaline-acetoxy]-n-propane and valeric acid chloride analogous to Example 12. The hydrochloride was obtained as an oil.

$C_{38}H_{49}BrN_2O_7$ x HCl (762.2); Calc.: C-59.88%; H-6.61%; Br-10.48%; Cl-4.65%; N-3.68%; Found: C-59.60%; H-6.174%; Br-10.78%; Cl-4.78%; N-3.97%.

Example 151

1-[4-Amino-3-bromo-5-(N-ethyl-cyclohexylaminomethyl)-benzoyloxy]-2-tetradecanoyloxy-3-[(+)-6-methoxy-α-methyl-2-naphthaline-acetoxy]-n-propane This compound was prepared from 1-[4-amino-3-bromo-5-(N-ethyl-cyclohexylaminomethyl)-benzoyloxy]-2-hydroxy-3-[(+(-6-methoxy-α-methyl-3-naphthaline-acetoxy]-n-propane and myristic acid chloride analogous to Example 12. The hydrochloride was obtained as an oil.

$C_{47}H_{65}BrN_2O_7$ x HCl (886.4); Calc.: C-63.69%; H-7.51%; BR-9.02%; Cl-4.00%; N-3.16%; Found: C-63.40%; H-7.78%; Br-9.13%; Cl-4.04%; N-3.05%.

Example 152

1-[4-Amino-3-bromo-5-(N-ethyl-cyclohexylaminomethyl)-benzoyloxy]-2-octadecanoyloxy-3-[(+)-6-methoxy-α-methyl-2-naphthaline-acetoxy]-n-propane This compound was prepared from 1-[4-amino-3-bromo-5-(N-ethyl-cyclohexylaminomethyl)-benzoyloxy]-2-hydroxy-3-[(+)-6-methoxy-α-methyl-2-naphthaline-acetoxy]-n-propane and stearic acid chloride analogous to Example 12. The hydrochloride was obtained as an oil.

$C_{51}H_{75}BrN_2O_7$ x HCl (944.6); Calc.: C-64.85%; H-8.11%; Br-8.46%; Cl-3.75%; N-2.97%; Found: C-64.58%; H-8.04%; Nr-8.45%; Cl-3.74%; N-3.09%.

Example 153

1-[4-Amino-3-bromo-5-(N-ethyl-cyclohexylaminomethyl)-benzoyloxy]-2-decanoyloxy-3-[(+)-6-methoxy-α-methyl-2-naphthaline-acetoxy]-n-propane This compound was prepared from 1-[4-amino-3-bromo-5-(N-ethyl-cyclohexylaminomethyl)-benzoyloxy]-2-hydroxy-3-[(+)-6-methoxy-α-methyl-2-naphthaline-acetoxy]-n-propane and capric acid chloride analogous to Example 12. The hydrochloride was obtained as an oil.

$C_{43}H_{59}BrN_2O_7$ x HCl (832.5); Calc.: C-62.05%; H-7.27%; Br-9.60%; Cl-4.26%; N-3.37%; Found: C-61.62%; H-7.25%; Br-10.15%; Cl-4.46%; N-3.74%.

Example 154

1-[1-(4-Chlorobenzoyl)-5-methoxy-2-methyl-1H-indole-3-acetyl]-6-(4-amino-3-bromo-5-diethylaminomethyl-benzoyl)D-mannitol This compound was prepared from 1-[1-(4-chlorobenzoyl)-5-methoxy-2-methyl-1H-indole-3-acetyl]-D-mannitol and 4-amino-3-bromo-5-diethylaminomethyl-benzoyl chloride in dichloromethane/pyridine, analogous to Example 10. Amorphous powder.

IR-spectrum (potassium bromide):
Ester-CO: 1710 cm$^{-1}$
Amide-CO: 1680 cm$^{-1}$ UV-spectrum (ethanol): λ max 230 nm (shoulder), 285 nm.

Example 155

1-{2-[(2,6-Dichlorophenyl)-amino]-phenylacetyl}-6-[4-amino-3-bromo-5-(N-ethyl-cyclohexylaminomethyl)-benzoyl]-D-mannitol This compound was prepared from 1-[4-amino-3-bromo-5-(N-ethyl-cyclohexylaminomethyl)-benzoyl]-D-mannitol and 2-[(2,6-dichlorophenyl)-amino]-phenyl-acetic acid analogous to Example 4. Amorphous powder.

M.p. of the hydrochloride: 170°–185° C. (foaming).

Example 156

1-[4-Amino-3-bromo-5-(N-ethyl-cyclohexylaminomethyl)benzamido]-2-[1-(4-chlorobenzoyl)-5-methoxy-2-methyl-1H-indole-3-acetoxy]-ethane This compound was prepared from 1-[4-amino-3-bromo-5-(N-ethyl-cyclohexylaminomethyl)-benzamido]-2-hydroxy-ethane and 1-(4-chlorobenzoyl)-5-methoxy-2-methyl-1H-indole-3-acetic acid imidazolide analogous to Example 1.

M.p. of the hydrochloride: from 125° C. (decomp.).

EXAMPLE 157

1-[4-Amino-3-bromo-5-(N-ethyl-cyclohexylaminomethyl)-benzamido]-3-[1-(4-chlorobenzoyl)-5-methoxy-2-methyl-1H-indole-3-acetoxy]-n-propane This compound was prepared from 1-[4-amino-3-bromo-5-(N-ethyl-cyclohexylaminomethyl)-benzamide]-3-hydroxy-n-propane and 1-(4-chlorobenzoyl)-5-methoxy-2-methyl-1H-indole-3-acetic acid imidazolide analogous to Example 13. Oil.

IR-spectrum (methylene chloride):
Ester-CO 1730 cm$^{-1}$
Amide-CO 1650 and 1675 cm$^{-1}$ UV-spectrum (ethanol): λ max 275 nm, shoulder ~325 nm.

Example 158

1-[4-Amino-3-bromo-5-(N-ethyl-cyclohexylaminomethyl)benzamido]-4-[1-(4-xhlorobenzoyl)-5-methoxy-2-methyl-1H-indole-3-acetoxy]-n-butane This compound was prepared from 1-[4-amino-3-bromo-5-(N-ethyl-cyclohexylaminomethyl)-benzamido]-4-hydroxy-n-butane and 1-(4-chlorobenzoyl)-5-methoxy-2-methyl-1H-indole-3-acetic acid imidazolide analogous to Example 13. Oil. The hydrochloride was obtained as a solid, amorphous substance.

$C_{39}H_{46}BrClN_4O_5$ x HCl (802.6); Calc.: C-58.36%; H.5.90%; Br-9.96%; Cl-8.83%; N-6.98%; Found: C-58.10%; H-6.02%; Br-9.92%; Cl-8.81%; N-6.84%.

Example 159

1-[4-Amino-3-bromo-5-(N-ethyl-cyclohexylaminomethyl)-benzamido]-5-[1-(4-chlorobenzoyl)-5-methoxy-2-methyl-1H-indole-3-acetoxy]-n-pentane This compound was prepared from 1-[4-Amino-3-bromo-5-(N-ethyl-cyclohexylaminomethyl)-benzamido]-5-hydroxy-n-pentane and 1-(4-chlorobenzoyl)-5-methoxy-2-methyl-1H-indole-3-acetic acid imidazolide analogous to Example 13. Oil.

The hydrochloride was obtained as a solid, amorphous substance.

$C_{40}H_{48}BrClN_4O_5$ x HCl (816.7); Calc.: C-58.83%; H-6.05%; Br-9.79%; Cl-8.68%; N-6.86%; Found: D-58.60%; H-6.18%; Br-9.62%; Cl-8.53%; N-6.85%.

Example 160

1-[4-Amino-3-bromo-5-(N-ethyl-cyclohexylaminomethyl)benzamido]-6-[1-(4-chlorobenzoyl)-5-methoxy-2-methyl-1H-indole-3-acetoxy]-n-hexane This compound was prepared from 1-[4-amino-3-bromo-5-(N-ethyl-cyclohexylaminomethyl)-benzamido]-6-hydroxy-n-hexane and 1-(4-chlorobenzoyl)-5-methoxy-2-methyl-1H-indole-3-acetic acid imidazole analogous to Example 13. Oil. The hydrochloride was obtained as a solid, amorphous substance.

$C_{41}H_{50}BrClN_4O_5$ x HCl (830.7); Calc.: C-59.28%; H-6.19%; Br-9.62%; Cl-8.53%; N-6.74%; Found: C-59.00%; H-6.32%; Br-9.68%; N-6.50%.

Example 161

1-[4-Amino-3-bromo-5-(N-ethyl-cyclohexylaminomethyl)-benzamido]-2-[(+)-6-methoxy-α-methyl-2-naphthaline-acetoxy]ethane This compound was prepared from 1-[4-amino-3-bromo-5-(N-ethyl-cyclohexylaminomethyl)-benzamido]-2-hydroxy-ethane and (+)-6-methoxy-α-methyl-2-naphthalineacetic acid imidazolide analogous to Example 13. The hydrogen maleate was obtained as an amorphous powder.

$C_{32}H_{40}BrN_3O_4$ x $C_4H_4O_4$ (726.7): Calc.: C-59.30%; H-6.16%; Br-10.86%; N-5.64%; Found: C-59.50%; H-6.10%; Br-11.00%; N-5.78%.

Example 162

1-[4-Amino-3-bromo-5-(N-ethyl-cyclohexylaminomethyl)benzamido]-3-[(+)-6-methoxy-α-methyl-2-naphthaline-acetoxy]-n-propane This compound was prepared from 1-[4-amino-3-bromo-5-(N-ethyl-cyclohexylaminomethyl)-benzamido]-3-hydroxy-n-propane and (+)-6-methoxy-α-methyl-2-naphthalineacetic acid imidazolide analogous to Example 13.

M.p. of the hydrochloride: 70°–90° C.

Example 163

1-[4-Amino-3-bromo-5-(N-ethyl-cyclohexylaminomethyl)-benzamido]-5-[(+)-6-methoxy-α-methyl-2-naphthaline-acetoxy-]-n-pentane This compound was prepared from 1[4-Amino-3-bromo-5-(N-ethyl-cyclohexylaminomethyl)-benzamido]-5-hydroxy-n-pentane and (+)-6-methoxy-α-methyl-2-naphthaline-acetic acid imidazolide analogous to Example 13. Oil.

IR-spectrum (methylene chloride):
Ester-CO: 1725 cm$^{-1}$
Amide-CO: 1650 cm$^{-1}$ UV-spectrum: λ max 235 nm, 280 nm.

Example 164

1-[4-Amino-3-bromo-5-(N-ethyl)-cyclohexylaminomethyl)-benzamido]-6-[(+)-6-methoxy-α-methyl-2-naphthaline-acetoxy]-n-hexane This compound was prepared from 1-[4-amino-3-bromo-5-(N-ethyl-cyclohexylaminomethyl)-benzamido]-6-hydroxy-n-hexane and (+)-6-methoxy-α-methyl-2-naphthalineacetic acid imidazolide analogous to Example 13. Oil. The hydrochloride was obtained as a solid, amorphous substance.

$C_{36}H_{48}BrN_3O_4$ x HCl (703.2): Calc.: C-61.49%; H-7.02%; Br-11.36%; Cl-5.04%; N-5.98%; Found: C-61.70%; H-7.10%; Br-11.22%; Cl-4.98%; N-5.59%.

Example 165

1-[4-Amino-3-bromo-5-(N-ethyl-cyclohexylaminomethyl)-benzoyloxy]-2]-[1-(4-chlorobenzoyl)-5-methoxy-2-methyl-1H-indole-3-acetamido]-ethane This compound was prepared from 1-[1-(4-chlorobenzoyl)-5-methoxy-2-methyl-1H-indole-3-acetamido]-2-hydroxy-ethane and 4-amino-3-bromo-5-(N-ethyl-cyclohexylaminomethyl)-benzoyl chloride analogous to Example 5.

M.p. of the hydrochloride: from 140° C. (decomp.).

Example 166

1-[4-Amino-3-bromo-5-(N-ethyl-cyclohexylaminomethyl)-benzoyloxy]-3-[1-(4-chlorobenzoyl)-5-methoxy-2-methyl-1H-indole-3-acetamido]-n-propane This compound was prepared from 1-[1-(4-chlorobenzoyl)-5-methoxy-2-methyl-1H-indole-3-acetamido]-3-hydroxy-n-propane and 4-amino-3-bromo-5-(N-ethyl-cyclohexylaminomethyl)-benzoyl chloride analogous to Example 10. Oil.

IR-spectrum (methylene chloride):
Ester-CO: 1700 cm$^{-1}$
Amide-CO: 1665 and 1680 cm$^{-1}$
UV-spectrum (ethanol): λ max 230 nm (shoulder), 290 nm.

Example 167

1-[4-Amino-3-bromo-5-(N-ethyl-cyclohexylaminomethyl)-benzoyloxy]-4-[1-(4-chlorobenzoyl)-5-methoxy-2-methyl-1H-indole-3-acetamido]-n-butane This compound was prepared from 1-[1-(4-chlorobenzoyl)-5-methoxy-2-methyl-1H-indole-3-acetamido]-4-hydroxy-n-butane and 4-amino-3-bromo-5-(N-ethyl-cyclohexylaminomethyl)-benzoyl chloride analogous to Example 10. Oil.

IR-spectrum (methylene chloride):
Ester-CO: 1710 cm$^{-1}$
Amide-CO: 1660 and 1680 cm$^{-1}$
UV-spectrum (ethanol): λ max 230 nm, 285 nm.

The hydrochloride was obtained as a solid, amorphous substance.

Example 168

1-[4-Amino-3-bromo-5-(N-ethyl-cyclohexylaminomethyl)benzoyloxy]-5-[1-(4-chlorobenzoyl)-5-methoxy-2-methyl-1H-indole-3-acetamido]-n-pentane This compound was prepared from 1-[1-(4-chlorobenzoyl)-5-methoxy-2-methyl-1H-indole-3-acetamido]-5-hydroxy-n-pentane and 4-amino-3-bromo-5-(N-ethyl-cyclohexylaminomethyl)-benzoyl chloride analogous to Example 10. Oil.

IR-spectrum (methylene chloride):
Ester-CO: 1710 cm$^{-1}$
Amide-CO: 1660 and 1680 cm$^{-1}$
UV-spectrum (ethanol): λ max 230 nm, 290 nm.

Example 169

1-[4-Amino-3-bromo-5-(N-ethyl-cyclohexylaminomethyl)-benzoyloxy]-6-[1-(4-chlorobenzoyl)-5-methoxy-2-methyl-1H-indole-3-acetamido]-n-hexane This compound was prepared from 1-[1-(4-chlorobenzoyl)-5-methoxy-2-methyl-1H-indole-3-acetamido]-6-hydroxy-n-hexane and 4-amino-3-bromo-5-(N-ethyl-cyclohexylaminomethyl)-benzoyl chloride anlogous to Example 10. Oil.

IR-spectrum (methylene chloride):
Ester-CO: 1710 cm$^{-1}$
Amide-CO: 1665 and 1680 cm$^{-1}$
UV-spectrum (ethanol): λ max 232 nm, 285 nm.

Example 170

1-[4-Amino-3-bromo-5-(N-ethyl-cyclohexylaminomethyl)-benzoyloxy]-3-[(+)-6-methoxy-α-methyl-phenylacetamido]-n-propane This compound was prepared from 1-[(+)-6-methoxy-α-methyl-phenylacetamido]-3-hydroxy-n-propane and 4-amino-3-bromo-5-(N-ethyl-cyclohexylaminomethyl)-benzoyl chloride analogous to Example 10. Oil.

IR-spectrum (methylene chloride):
Ester-CO: 1710 cm$^{-1}$
Amide-CO: 1640 cm$^{-1}$
UV-spectrum (ethanol): λ max 234 nm, 285 nm.

Example 171

1-[4-Amino-3-bromo-5-(N-ethyl-cyclohexylaminomethyl)benzoyloxy]-5-[(+)-6-methoxy-α-methyl-phenylacetamido]-n-pentane This compound was prepared from 1-[(+)-6-methoxy-α-methyl-phenylacetamido]-5-hydroxy-n-pentane and 4-amino-3-bromo-5-(N-ethyl-cyclohexylaminomethyl)-benzoyl chloride analogous to Example 10. Oil.

IR-spectrum (methylene chloride):
Ester-CO: 1700 cm$^{-1}$
Amide-CO: 1670 cm$^{-1}$
UV-spectrum (ethanol): λ max 235 nm, 295 nm.

Example 172

1-[4-Amino-3-bromo-5-(N-ethyl-cyclohexylaminomethyl)-benzoyloxy]-6-[(+)-6-methoxy-α-methyl-phenylacetamido]-n-hexane This compound was prepared from 1-[(+)-6-methoxy-α-methyl-phenylacetamido]-6-hydroxy-n-hexane and 4-amino-3-bromo-5-(N-ethyl-cyclohexylaminomethyl)-benzoyl chloride analogous to Example 10. Oil.

IR-spectrum (methylene chloride):
Ester-CO: 1705 cm$^{-1}$
Amide-CO: 1645 cm$^{-1}$
UV-spectrum (ethanol): λ max 235 nm, 280 nm.

Example 173

Trans-4-[4-amino-3-bromo-5-(N-ethyl-cyclohexylaminomethyl)-benzamido]-1-[1-(4-chlorobenzoyl)-5-methoxy-2-methyl-1H-indole-3-acetoxy]-cyclohexane This compound was prepared from trans-4-[4-amino-3-bromo-5-(N-ethyl-cyclohexylaminomethyl)-benzamido]-cyclohexanol and 1-(4-chlorobenzoyl)-5-methoxy-2-methyl-1H-indole-3-acetic acid imidazolide analogous to Example 1.

M.p. 160°–163° C. (decomp.).

Example 174

1-Amino-3-bromo-5-(N-ethyl-cyclohexylaminomethyl)benzamido]-3-[1-(4-chlorobenzoyl)-5-methoxy-2-methyl-1H-indole-3-acetamido]-n-propane This compound was prepared from 1-[1-(4-chlorobenzoyl)-5-methoxy-2-methyl-1H-indole-3-acetamido]-3-amino-n-propane and 4-amino-3-bromo-5-(N-ethyl-cyclohexylaminomethyl)-benzoyl chloride in the presence of triethylamine, analogous to Example 7.

M.p. 161°–167° C.

Example 175

1-[4-Amino-3-bromo-5-(N-ethyl-cyclohexylaminomethyl)benzamido]-2-](+)-6-methoxy-α-methyl-2-naphthaline-acetamido]-ethane This compound was prepared from 1-[(+)-6-methoxy-α-methyl-2-naphthaline-acetamido]-2-aminoethane and 4-amino-3-bromo-5-(N-ethyl-cyclohexylaminoethyl)-benzoyl chloride in the presence of triethylamine, analogous to Example 7.

M.p. 136°–137° C.

Example 176

1-[4-Amino-3-bromo-5-(N-ethyl-cyclohexylaminomethyl)benzamido]-3-[(+)-6-methoxy-α-methyl-2-naphthaline-acetamido]-n-propane This compound was prepared from 1-[(+)-6-methoxy-α-methyl-2-naphthaline-acetamido]-3-amino-n-propane and 4-amino-3-bromo-5-(N-ethyl-cyclohexylaminomethyl)-benzoyl chloride in the presence of triethylamine, analogous to Example 7.

M.p. of the hydrochloride: beginning at 126° C. (decomp.).

Example 177

1-[4-Amino-3-bromo-5-(N-ethyl-cyclohexylaminomethyl)benzamido]-4-[(+)-6-methoxy-α-methyl-2-naphthaline-acetamido]-n-butane This compound was prepared from 1-[(+)-6-methoxy-α-methyl-2-naphthaline-acetamido]-4-amino-n-butane and 4-amino-3-bromo-5-(N-ethyl-cyclohexylaminomethyl)-benzoyl chloride in the presence of triethylamine, analogous to Example 7.

M.p.: 130°–131° C.

Example 178

1-[4-Amino-3-bromo-5-(N-ethyl-cyclohexylaminomethyl)benzamido]-5-[(+)-6-methoxy-α-methyl-2-naphthaline-acetamido]-n-pentane This compound was prepared from 1[(+)-6-methoxy-α-methyl-2-naphthaline-acetamido]-5-amino-n-pentane and 4-amino-3-bromo-5-(N-ethyl-cyclohexylaminomethyl)-benzoyl chloride in the presence of triethylamine, analogous to Example 7.

M.p.: beginning at 72° C. (sintering.

Example 179

1-[4-Amino-3-bromo-5-(N-ethyl-cyclohexylaminomethyl)benzamido]-6-[(+)-6-methoxy-α-methyl-2-naphthaline-acetamido]-n-hexane This compound was prepared from 1-[(+)-6-methoxy-α-methyl-2-naphthaline-acetamido]-6-amino-n-hexane and 4-amino-3-bromo-5-(N-ethyl-cyclohexylaminomethyl)-benzoyl chloride in the presence of triethylamine, analogous to Example 7.

M.p.: 149°–150° C.

Example 180

N-[4-Amino-3-bromo-5-(N-ethyl-cyclohexylaminomethyl)benzoyl]-O-[1-(4-chlorobenzoyl)-5-methoxy-2-methyl-1H-indole-3-acetyl]-L-serine methyl ester This compound was prepared from N-[4-amino-3-bromo-5-(N-ethyl-cyclohexylaminomethyl)-benzoyl]-L-serine methyl ester and 1-(4-chlorobenzoyl)-5-methoxy-2-methyl-1H-indole-3-acetic acid imidazolide analogous to Example 1. Foam.

IR-spectrum (methylene chloride):
NH$_2$: 3435 cm$^{-1}$
N-alkyl: 2920 cm$^{-1}$
OCH$_3$: 2850 cm$^{-1}$
Ester-CO: 1745 cm$^{-1}$
Amide-CO: 1675 and 1655 cm$^{-1}$
UV-spectrum (methanol): λ max 230 nm, 290 nm.

Example 181

O-[4-amino-3-bromo-5-(N-ethyl-cyclohexylaminomethyl)benzoyl]-N-[1-(4-chlorobenzoyl)-5-methoxy-2-methyl-1H-indole-3-acetyl]-L-serine methyl ester This compound was prepared from N-[1-(4-chlorobenzoyl)-5-methoxy-2-methyl-1H-indole-3-acetyl]-L-serine methyl ester and 4-amino-3-bromo-5-(N-ethyl-cyclohexylaminomethyl)-benzoyl chloride analogous to Example 7; pyridine was used instead of triethylamine and 4-dimethylamino-pyridine. Oil.

IR-spectrum (methylene chloride):
NH$_2$: 3410 cm$^{-1}$
N-alkyl: 2910 cm$^{-1}$
OCH$_3$: 2840 cm$^{-1}$
Ester-CO: 1750 and 1700 cm$^{-1}$
Amide-CO: 1675 cm$^{-1}$
UV-spectrum (ethanol): λ max 230 nm, 295 nm.

Example 182

N-[4-Amino-3-bromo-5-(N-ethyl-cyclohexylaminomethyl)benzoyl]-O-[(+)-6-methoxy-α-methyl-2-naphthaline-acetyl]-L-serine methyl ester This compound was prepared from N-[4-amino-3-bromo-5-(N-ethyl-cyclohexylaminomethyl)-benzoyl]-L-serine methyl ester and (+)-6-methoxy-α-methyl-2-naphthaline-acetic acid imidazolide analogous to Example 1. Foam.

IR-spectrum (methylene chloride):
NH$_2$ : 3440 cm$^{-1}$
N-alkyl: 2920 cm$^{-1}$
OCH$_3$: 2850 cm$^{-1}$
Estero-CO: 1730 cm$^{-1}$
Amide-CO: 1660 cm$^{-1}$
UV-spectrum (ethanol): λ max 234 nm and 295 nm.

Example 183

1-[4-Amino-3-bromo-5-(N-methyl-benzylaminomethyl)-benzoyloxy]-5-[2-fluoro-α-methyl-(1,1'-biphenyl)-4-acetoxy]-n-pentane This compound was prepared from 2-fluoro-α-methyl-(1,1'-biphenyl)-4-acetic acid imidazolide and 1-[4-amino-3-bromo-5-(N-methyl-benzylaminomethyl)-benzoyloxy]-5-hydroxy-n-pentane analogous to Example 1. Oil.

IR-spectrum (methylene chloride):
NH$_2$: 3450 cm$^{-1}$
Ester-CO: 1705, 1725 cm$^{-1}$
UV-spectrum: λ max 232 nm and 292 nm.

Example 184

1-[4-Amino-3-bromo-5-(N-methyl-cyclohexylaminomethyl)benzoyloxy]-5-[2-fluoro-α-methyl-(1,1'-biphenyl)-4-acetoxy]-n-pentane This compound was prepared from 2-fluoro-α-methyl-(1,1'-biphenyl)-4-acetic acid imidazolide and 1-[4-amino-3-bromo-5-(N-methyl-cyclohexylaminomethyl)-benzoyloxy]-5-hydroxy-n-pentane analogous to Example 1.

M.p. of the hydrochloride: 107°–111° C.

Example 185

1-(4-Amino-3-bromo-5-cyclohexylaminomethyl-benzoyloxy)-5-[2-fluoro-α-methyl-(1,1'-biphenyl)-4-acetoxy]-n-pentane This compound was prepared from 2-fluoro-α-methyl-(1,1'-biphenyl)-4-acetic acid imidazolide and 1-(4- amino-3-bromo-5-cyclohexylaminomethyl-benzoyloxy)-5-hydroxy-n-pentane analogous to Example 1. Oil.
IR-spectrum (methylene chloride):
$NH_2$: 3440 cm$^{-1}$
Ester-CO: 1700, 1730 cm$^{-1}$
UV-spectrum (ethanol): λ max 232 nm and 290 nm.

Example 186

1-(4-Amino-3-bromo-5-isopropylaminomethyl-benzoyloxy)-5-[2-fluoro-α-methyl-(1,1'-biphenyl)-4-acetoxy]-n-pentane This compound was prepared from 2-fluoro-α-methyl-(1,1'-biphenyl)-4-acetic acid imidazolide and 1-(4-amine-3-bromo-5-isopropylaminomethyl-benzyloxy)-5-hydroxy-n-pentane analogous to Example 1. Oil.
IR-spectrum (methylene chloride):
$NH_2$: 3440 cm$^{-1}$
Ester-CO: 1700, 1724 cm$^{-1}$
UV-spectrum (ethanol): λ max 234 nm and 292 nm.

Example 187

1-(4-Amino-3-bromo-5-tert. butylaminomethyl-benzoyloxy)-5-[2-fluoro-α-methyl-(1,1'-biphenyl)-4-acetoxy]-n-pentane This compound was prepared from 2-fluoro-α-methyl-(1,1'-biphenyl)-4-acetic acid imidazolide and 1-(4-amino-3-bromo-5-tert. butylaminomethyl-benzoyloxy)-5-hydroxy-n-pentane analogous to Example 1. Oil.
IR-spectrum (methylene chloride):
$NH_2$: 3450 cm$^{-1}$
Ester-CO: 1710, 1730 cm$^{-1}$
UV-spectrum (ethanol): λ max 235 nm and 295 nm.

Example 188

1-(4-Amino-3-bromo-5-dimethylaminomethyl-benzoyloxy)-5-[2-fluoro-α-methyl-(1,1'-biphenyl)-4-acetoxy]-n-pentane This compound was prepared from 2-fluoro-α-methyl-(1,1'-biphenyl)-4-acetic acid imidazolide and 1-(4-amino-3-bromo-5-dimethylaminomethyl-benzoyloxy)-5-hydroxy-n-pentane analogous to Example 1.
M.p. of the hydrochloride: 105° C. (sintering from 75° C.).

Example 189

1-[4-Amino-3-bromo-5-(N-methyl-piperazinomethyl)-benzoyloxy]-5-[2-fluoro-α-methyl-(1,1'-biphenyl)-4-acetoxy]-n-pentane This compound was prepared from 2-fluoro-α-methyl-(1,1'-biphenyl)-4-acetic acid imidazolide and 1-[4-amino-3-bromo-5-(N-methyl-piperazinomethyl)-benzoyloxy]-5-hydroxy-n-pentane analogous to Example 1. Oil.
IR-spectrum (methylene chloride):
$NH_2$: 3440 cm$^{-1}$
Ester-CO: 1700, 1730 cm$^{-1}$
UV spectrum (ethanol): λ max 232 nm and 286 nm.

Example 190

1-(4-Amino-3-bromo-5-morpholinomethyl-benzoyloxy)-5-[2-fluoro-α-methyl-(1,1'-biphenyl)-4-acetoxy]-n-pentane This compound was prepared from 2-fluoro-α-methyl-(1,1'-biphenyl)-4-acetic acid imidazolide and 1-(4-amino-3-bromo-5-morpholinomethyl-benzoyloxy)-5-hydroxy-n-pentane analogous to Example 1. Oil.
IR-spectrum (methylene chloride):
$NH_2$: 3440 cm$^{-1}$
Ester-CO: 1700, 1725 cm$^{-1}$
UV-spectrum (ethanol): λ max 232 nm and 290 nm.

Example 191

1-(4-Amino-3-bromo-5-hexamethylene-iminomethyl-benzoyloxy-5-[2-fluoro-α-methyl-(1,1'-biphenyl)-4-acetoxy]-n-pentane This compound was prepared from 2-fluoro-α-methyl-(1,1'-biphenyl)-4-acetic acid imidazolide and 1-(4-amino-3-bromo-5-hexamethyleneiminomethyl-benzoyloxy)-5-hydroxy-n-pentane analogous to Example 1. Oil.
IR-spectrum (methylene chloride):
$NH_2$: 3440 cm$^{-1}$
Ester-CO: 1770, 1730 cm$^{-1}$
UV-spectrum (ethanol): λ max 232 nm, 290 nm.

Example 192

1-(4-Amino-3-bromo-5-piperidinomethyl-benzoyloxy)-5-[2-fluoro-α-methyl-(1,1'-biphenyl)-4-acetoxy]-n-pentane This compound was prepared from 2fluoro-α-methyl-(1,1'-biphenyl)-4-acetic acid imidazolide and 1-(4-amino-3-bromo-5-piperidinomethyl-benzoyloxy)-5-hydroxy-n-pentane analogous to Example 1. Oil.
IR-spectrum (methylene chloride):
$NH_2$: 3450 cm$^{-1}$
Ester-CO: 1705, 1730 cm$^{-1}$
UV-spectrum (ethanol): λ max 235 nm, 288 nm.

Example 193

1-(4-Amino-3-bromo-5-pyrrolidinomethyl-benzoyloxy)-5-[2-fluoro-α-methyl-(1,1'-biphenyl)-4-acetoxy]-n-pentane This compound was prepared from 2-fluoro-α-methyl-(1,1'-biphenyl)-4-acetic acid imidazolide and 1-(4-amino-3-bromo-5-pyrrolidinomethyl-benzoyloxy)-5-hydroxy-n-pentane analogous to Example 1. Oil.
IR-spectrum (methylene chloride):
$NH_2$: 3450 cm$^{-1}$
Ester-CO: 1705, 1730 cm$^{-1}$
UV-spectrum (ethanol): max 232 nm, 290 nm.

Example 194

1-[4-Amino-3-bromo-5-(N-n-propyl-cyclohexylaminomethyl)benzoyloxy]-5-[2-fluoro-α-methyl-(1,1'-biphenyl)-4-acetoxy]-n-pentane This compound was prepared from 2-fluoro-α-methyl-(1,1'-biphenyl)-4-acetic acid imidazolide and 1-[4-amino-3-bromo-5-(N-n-propyl-cyclohexylaminomethyl)-benzoyloxy]-5-hydroxy-n-pentane analogous to Example 1. Oil.
IR-spectrum (methylene chloride):
$NH_2$: 3450 cm$^{-1}$
Ester-CO: 1700, 1725 cm$^{-1}$
UV-spectrum (ethanol): λ max 233 nm, 290 nm.

Example 195

1-[4-Amino-3-bromo-5-(N-ethyl:cycloheptylaminomethyl)-benzoyloxy]-5-[2-fluoro-α-methyl-(1,1'-biphenyl)-4-acetoxy]-n-pentane This compound was prepared from 2-fluoro-α-methyl-(1,1'-biphenyl)-4-acetic acid imidazolide and 1-[4-amino-3-bromo-5-(N-ethyl-cycloheptylaminomethyl)-benzoyloxy]-5-hydroxy-n-pentane analogous to Example 1. Oil.
IR-spectrum (methylene chloride):

NH$_2$: 3450 cm$^{-1}$
Ester-CO: 1705, 1730 cm$^{-1}$
UV-spectrum (ethanol): λ max 230 nm, 285 nm.

Example 196

1-[4-Amino-3-bromo-5-(N-ethyl-cyclopentylaminomethyl)-benzoyloxy]-5-[2-fluoro-α-methyl-(1,1'-biphenyl)-4-acetoxy]-n-pentane This compound was prepared from 2-fluoro-α-methyl-(1,1'-biphenyl)-4-acetic acid imidazolide and 1-[4-amino-3-bromo-5-(N-ethyl-cyclopentylaminomethyl)-benzoyloxy]-5-hydroxy-n-pentane analogous to Example 1. Oil.

IR-spectrum (methylene chloride):
NH$_2$: 3450 cm$^{-1}$
Ester-CO: 1700, 1730 cm$^{-1}$
UV-spectrum (ethanol): λ max 232 nm, 290 nm.

Example 197

1-(4-Amino-3-bromo-5-diethylaminomethyl-benzoyloxy)-5-[2-fluoro-α-methyl-(1,1'-biphenyl)-4-acetoxy]-n-pentane This compound was prepared from 1-(4-amino-3-bromo-5-diethylaminomethyl-benzoyloxy)-5-hydroxy-n-pentane and 2-fluoro-α-methyl-(1,1'-biphenyl)-4-acetic acid analogous to Example 4. Oil.

IR-spectrum (methylene chloride):
NH$_2$: 3440 cm$^{-1}$
N-alkyl: 2940 cm$^{-1}$
Ester-CO: 1705, 1735 cm$^{-1}$
UV-spectrum (ethanol): λ max 235 nm, 280 nm.

Example 198

1-(4-Amino-3-bromo-5-diethylaminomethyl-benzoyloxy)-2-[2-fluoro-α-methyl-(1,1'-biphenyl)-4-acetoxy]-ethane This compound was prepared from 1-(4-amino-3-bromo-5-diethylaminomethyl-benzoyloxy)-2-hydroxy-ethane and 2-fluoro-α-methyl-(1,1'-biphenyl)-4-acetic acid analogous to Example 4. Oil.

IR-spectrum (methylene chloride):
NH$_2$: 3440 cm$^{-1}$
N-alkyl: 2940 cm$^{-1}$
Ester-CO: 1705, 1735 cm$^{-1}$
UV-spectrum (ethanol): λ max 235 nm, 280 nm.

Example 199

1-(4-Amino-3-bromo-5-diethylaminomethyl-benzoyloxy)-3-[2-fluoro-α-methyl-(1,1'-biphenyl)-4-acetoxy]-n-propane This compound was prepared from 1-(4-amino-3-bromo-5-diethylaminomethyl-benzoyloxy)-3-hydroxy-n-propane and 2-fluoro-α-methyl-(1,1'-biphenyl-4-acetic acid analogous to Example 4. Oil.

IR-spectrum (methylene chloride):
NH$_2$: 3440 cm$^{-1}$
N-alkyl: 2930 cm$^{-1}$
Ester-CO: 1700, 1730 cm$^{-1}$
UV-spectrum (ethanol): λ max 235 nm, 280 nm.

Example 200

1-(4-Amino-3-bromo-5-diethylaminomethyl-benzoyloxy)-4-[2-fluoro-α-methyl-(1,1'-biphenyl)-4-acetoxy]-n-butane This compound was prepared from 1-(4-amino-3-bromo-5-diethylaminomethyl-benzoyloxy)-4-hydroxy-n-butane and 2-fluoro-α-methyl-(1,1'-biphenyl)-4-acetic acid analogous to Example 4. Oil.

IR-spectrum (methylene chloride):
NH$_2$: 3440 cm$^{-1}$
N-alkyl: 2940 cm$^{-1}$
Ester-CO: 1700, 1730 cm$^{-1}$
UV-spectrum (ethanol): λ max 235 nm, 280 nm.

Example 201

1-(4-amino-3-bromo-5-diethylaminomethyl-benzoyloxy)-6-[2-fluoro-α-methyl-(1,1'-biphenyl)-4-acetoxy]-n-hexane This compound was prepared from 1-(4-amino-3-bromo-5-diethylaminomethyl-benzoyloxy)-6-hydroxy-n-hexane and 2-fluoro-α-methyl-(1,1'-biphenyl)-4-acetic acid analogous to Example 4. Oil.

IR-spectrum (methylene chloride):
NH$_2$: 3440 cm$^{-1}$
N-alkyl: 2940 cm$^{-1}$
Ester-CO: 1700, 1730 cm$^{-1}$
UV-spectrum (ethanol): λ max 235 nm, 280 nm.

Example 202

1-[4-Amino-3-bromo-5-(N-ethyl-cyclohexylaminomethyl)-benzoyloxy]-3-[2-fluoro-α-methyl-(1,1'-biphenyl)-4-acetoxy]-n-propane This compound was prepared from 1-[4-amino-3-bromo-5-(N-ethyl-cyclohexylaminomethyl)-benzoyloxy]-3-hydroxy-n-propane and 2-fluoro-α-methyl-(1,1'-biphenyl)-4-acetic acid analogous to Example 4. Oil.

IR-spectrum (methylene chloride):
NH$_2$: 3440 cm$^{-1}$
N-alkyl: 2930 cm$^{-1}$
Ester-CO: 1705, 1730 cm$^{-1}$
UV-spectrum (ethanol): λ max 235 nm, 280 nm.

Example 203

1-[4-Amino-3-bromo-5-(n-ethyl-cyclohexylaminomethyl)-benzoyloxy]-4-[2-fluoro-α-methyl-(1,1'-biphenyl)-4-acetoxy]-n-butane This compound was prepared from 1-[4-amino-3-bromo-5-(N-ethyl-cyclohexylaminomethyl)-benzoyloxy]-4-hydroxy-n-butane and 2-fluoro-α-methyl-(1,1'-biphenyl)-4-acetic acid analogous to Example 4. Oil.

IR-spectrum (methylene chloride):
NH$_2$: 3460 cm$^{-1}$
N-alkyl: 2930 cm$^{-1}$
Ester-CO: 1705, 1730 cm$^{-1}$
UV-spectrum (ethanol): λ max 235 nm, 280 nm.

Example 204

1-[4-Amino-3-bromo-5-(N-ethyl-cyclohexylaminomethyl)-benzoyloxy]-5-[2-fluoro-α-methyl-(1,1'-biphenyl)-4-acetoxy]-n-pentane This compound was prepared from 1-[4-amino-3-bromo-5-(N-ethyl-cyclohexylaminomethyl)-benzoyloxy]-5-hydroxy-n-pentane and 2-fluoro-α-methyl-(1,1'-biphenyl)-4-acetic acid analogous to Example 4. Oil.

IR-spectrum (methylene chloride):
NH$_2$: 3440 cm$^{-1}$
N-alkyl: 2930 cm$^{-1}$
Ester-CO: 1700, 1730 cm$^{-1}$
UV-spectrum (ethanol): λ max 235 nm, 280 nm.

Example 205

1-[4-Amino-3-bromo-5-(N-ethyl-cyclohexylaminomethyl)-benzoyloxy]-6-[2-fluoro-α-methyl-(1,1'-biphenyl)-4-acetoxy]-n-hexane This compound was prepared from 1-[4-amino-3-bromo-5-(N-ethyl-cyclohexylaminomethyl)-benzoyloxy]-6-hydroxy-n-hexane and 2-fluoro-α-methyl-(1,1'-biphenyl)-acetic acid analogous to Example 4. oil.

IR-spectrum (methylene chloride):
NH$_2$: 3440 cm$^{-1}$
N-alkyl: 2930 cm$^{-1}$
Ester-CO: 1700, 1730 cm$^{-1}$
UV-spectrum (ethanol): λ max 235 nm, 280 nm.

Example 206

1-[4-Amino-3-bromo-5-(N-ethyl-cyclohexylaminomethyl)-benzamido]-4-[2-fluoro-α-methyl-(1,1'-biphenyl)-4-acetoxy]-n-butane This compound was prepared from 1-[4-amino-3-bromo-5-(N-ethyl-cyclohexylaminomethyl)-benzamido]-4-hydroxy-n-butane and 2-fluoro-α-methyl-(1,1'-biphenyl)-4-acetic acid analogous to Example 3 or 4. Colorless foam.

IR-spectrum (methylene chloride):
NH$_2$: 3510 cm$^{-1}$
Ester-CO: 1740 cm$^{-1}$
Amide-Co: 1670 cm$^{-1}$

Example 207

N-[2-(4-Amino-3-bromo-5-diethylaminomethyl-benzoyloxy)-ethyl]-N'-{3-[2-fluoro-α-methyl-(1,1'-biphenyl)-4-acetoxy]-propyl}-piperazine This compound was prepared from N-{3-[2-fluoro-α-methyl-(1,1'-biphenyl)-4-acetoxy]-propyl}-N'-(2-hydroxyethyl)-piperazine and 4-amino-3-bromo-5-diethylaminomethylbenzoic acid analogous to Example 4.

M.p. of the trihydrogen maleate: 163°–166° C.

Example 208

N-[3-(4-amino-3-bromo-5-diethylaminomethyl-benzoyloxy)-propyl]-N'-{2-[2-fluoro-α-methyl-(1,1'-biphenyl)-4-acetoxy]-ethyl}-piperazine This compound was prepared from N-[3-(4-amino-3-bromo-5-diethylaminomethyl-benzoyloxy)-propyl]-N'-(2-hydroxyethyl)-piperazine and 2-fluoro-α-methyl-(1,1'-biphenyl)-4-acetic acid analogous to Example 4.

M.p. of the trihydrogen maleate: 144°–147° C.

Example 209

N-{3-[4-amino-3-bromo-5-(N-ethyl-cyclohexylaminomethyl)-benzoyloxy]-propyl}-N'-{2-[2-fluoro-α-methyl-(1,1'-biphenyl)-4-acetoxy]-ethyl}-piperazine This compound was prepared from N-{3-[4-amino-3-bromo-5-(N-ethyl-cyclohexylaminomethyl)-benzoyloxy]-propyl}-N'-(2-hydroxyethyl)-piperazine and 2-fluoro-α-methyl-(1,1'-biphenyl)-4-acetic acid analogous to Example 4

M.p. of the trihydrogen maleate: 132°–135° C.

Example 210

N-{2-[4-amino-3-bromo-5-(N-ethyl-cyclohexylaminomethyl)-benzoyloxy]-ethyl}-N'-{3-[2-fluoro-α-methyl-(1,1'-biphenyl)-4-acetoxy]-propyl}-piperazine This compound was prepared from N-{3-[2-fluoro-α-methyl-(1,1'-biphenyl)-4-acetoxy]-propyl}-N'-(2-hydroxyethyl)-piperazine and 4-amino-3-bromo-5-(N-ethyl-cyclohexylaminomethyl)-benzoic acid analogous to Example 4.

M.p. of the trihydrogen maleate: 150°–153° C.

Example 211

N-{2-[4-amino-3-bromo-5-(N-ethyl-cyclohexylaminomethyl)-benzoyloxy]-ethyl}-N-{2-[2-fluoro-α-methyl-(1,1'-biphenyl)-4-acetoxy]-ethyl}-methylamine This compound was prepared from N-{2-[4-amino-3-bromo-5-(N-ethyl-cyclohexylaminomethyl)-benzoyloxy]-ethyl}-N-(2-hydroxyethyl)-methylamine and 2-fluoro-α-methyl-(1,1'-biphenyl)-4-acetic acid analogous to Example 4. Oil.

C$_{36}$H$_{45}$BrFN$_3$O$_4$ (682.7): Calc.: C-63.34%; H-6.64%; Br-11.71%; N-6.16%; Found: C-63.45%; H-6.59%; Br-11.85%; N-6.05%.

Example 212

N-{2-[4-amino-3-bromo-5-(N-ethyl-cyclohexylaminomethyl)-benzoyloxy]-ethyl}-N-{2-[2-fluoro-α-methyl-(1,1'-biphenyl)-4-acetoxy]-ethyl}-ethylamine This compound was prepared from N-{2-[4-amino-3-bromo-5-(N-ethyl-cyclohexylaminomethyl)-benzoyloxy]-ethyl}-N-(2-hydroxyethyl)-ethylamine and 2-fluoro-α-methyl-(1,1'-biphenyl)-4-acetic acid analogous to Example 4. Oil.

C$_{37}$H$_{47}$BrFN$_3$O$_4$ (696.7): Calc.: C-63.79%; H-6.80%; Br-11.47%; N-6.04%; Found: C-63.80%; H-6.85%; Br-11.40%; N-5.96%.

Example 213

N-[2-(4-amino-3-bromo-5-diethylaminomethyl-benzoyloxy)-ethyl]-N-{2-[2-fluoro-α-methyl-(1,1'-biphenyl)-4-acetoxy]-ethyl}-methylamine This compound was prepared from N-[2-(4-amino-3-bromo-5-diethylaminomethyl-benzoyloxy)-ethyl]-N-(2-hydroxyethyl)-methylamine and 2-fluoro-α-methyl-(1,1'-biphenyl)-4-acetic acid analogous to Example 4. Oil.

C$_{32}$H$_{39}$BrFN$_3$O$_4$ (628.6): Calc.: C-61.44%; H-6.25%; Br-12.71%; N-6.69%; Found: C-61.36%; H-6.54%; Br-12.55%; N-6.71%.

Example 214

N-[2-(4-amino-3-bromo-5-diethylaminomethyl-benzoyloxy)-ethyl]-N-{2-[2-fluoro-α-methyl-(1,1'-biphenyl)-4-acetoxy]-ethyl}-ethylamine This compound was prepared from N-[2-(4-amino-3-bromo-5-diethylaminomethyl-benzoyloxy)-ethyl]-N-(2-hydroxyethyl)-ethylamine and 2-fluoro-α-methyl-(1,1'-biphenyl)-4-acetic acid analogous to Example 4. Oil.

C$_{33}$H$_{41}$BrFN$_3$O$_4$ (642.6): Calc.: C-61.68%; H-6.43%; Br-12.44%; N-6.54%; Found: C-61.87%; H-6.21%; Br-12.30%; N-6.50%.

Example 215

2-(4-Amino-3-bromo-5-diethylaminomethyl-benzoyloxy)-2'-[2-fluoro-α-methyl-(1,1'-biphenyl)-4-acetoxy]-diethyloxide This compound was prepared from 2-(4-amino-3-bromo-5-diethylaminomethyl-benzoyloxy)-2'-hydroxy-diethyloxide and 2-fluoro-α-methyl-(1,1'-biphenyl)-4-acetic acid analogous to Example 4. Oil.

C$_{31}$H$_{36}$BrFN$_2$O$_5$ (615.6): Calc.: C-60.49%; H-5.90%; Br-12.98%; N-4.55%; Found: C-60.72%; H-5.78%; Br-12.75%; N-4.69%.

Example 216

2-(4-Amino-3-bromo-5-diethylaminomethyl-benzoyloxy)-2'-[2-fluoro-α-methyl-(1,1'-biphenyl)-4-acetoxy]-diethylsulfide This compound was prepared from 2-(4-amino-3-bromo-5-diethylaminomethyl-benzoyloxy)-2'-hydroxydiethylsulfide and 2-fluoro-α-methyl-(1,1'-biphenyl)-4-acetic acid analogous to Example 4. Oil.

$C_{31}H_{36}BrFN_2O_4S$ (631.6): Calc.: C-58.95%; H-5.75%; Br-12.65%; N-4.44%; S-5.08%; Found: C-59.45%; H-5.75%; Br-12.95%; N-4.58%; S-5.18%.

Example 217

1-(4-Amino-3-bromo-5-dimethylaminomethyl-benzoyloxy)-4-(3-benzoyl-α-methyl-phenylacetoxy)-n-butane This compound was prepared from 1-(4-amino-3-bromo-5-dimethylaminomethyl-benzoyloxy)-4-hydroxy-n-butane and 3-benzoyl-α-methyl-phenylacetic acid imidazolide analogous to Example 1.

M.p. of the hydrochloride: 117°–122° C.

Example 218

1-(4-Amino-3-bromo-5-piperidinomethyl-benzoyloxy)-4-(3-benzoyl-α-methyl-phenylacetoxy)-n-butane This compound was prepared from 1-(4-amino-3-bromo-4-piperidinomethyl-benzoyloxy)-4-hydroxy-n-butane and 3-benzoyl-α-methyl-phenylacetic acid imidazolide analogous to Example 1.

M.p. of the hydrochloride: 123°–125° C.

Example 219

1-(4-Amino-3-bromo-5-pyrrolidinomethyl-benzoyloxy)-4-(3-benzoyl-α-methyl-phenylacetoxy)-n-butane This compound was prepared from 1-(4-amino-3-bromo-5-pyrrolidinomethyl-benzoyloxy)-4-hydroxy-n-butane and 3-benzoyl-α-methyl-phenylacetic acid imidazolide analogous to Example 1. Amorphous hydrochloride.

$C_{32}H_{35}BrN_2O_5$ x HCl (644.02): Calc.: C-59.68%; H-5.63%; Br-12.41%; Cl-5.51%; N-4.35%; Found: C-59.63%; H-5.61%; Br-12.18%; Cl-5.40%; N-4.34%.

Example 220

1-(4-Amino-3-bromo-5-cyclohexylaminomethyl-benzoyloxy)-4-(3-benzoyl-α-methyl-phenylacetoxy)-n-butane This compound was prepared from 1-(4-amino-3-bromo-5-cyclohexylaminomethyl-benzoyloxy)-4-hydroxy-n-butane and 3-benzoyl-α-methyl-phenylacetic acid imidazolide analogous to Example 1. Amorphous hydrochloride.

$C_{34}H_{39}BrN_2O_5$ x HCl (672.1): Calc.: C-60.76%; H-6.00%; Br-11.89%; Cl-5.27%; N-4.17%; Found: C-60.52%; H-6.02%; Br-12.05%; Cl-5.35%; N-4.34%.

Example 221

1-[4-Amino-3-bromo-5-(N-methyl-piperazinomethyl)-benzoyloxy]-4-(3-benzoyl-α-methyl-phenylacetoxy)-n-butane This compound was prepared from 1-[4-amino-3-bromo-5-(N-methyl-piperazino-methyl)-benzoyloxy]-4-hydroxy-n-butane and 3-benzoyl-α-methyl-phenylacetic acid imidazolide analogous to Example 1.

M.p. of the hydrochloride: 183°–186° C.

Example 222

1-(4-Amino-3-bromo-5-isopropylaminomethyl-benzoyloxy)-4-(3-benzoyl-α-methyl-phenylacetoxy)-n-butane This compound was prepared from 1-(4-Amino-3-bromo-5-isopropylaminomethyl-benzoyloxy)-4-hydroxy-n-butane and 3-benzoyl-α-methyl-phenylacetic acid imidazolide analogous to Example 1. Amorphous hydrochloride.

$C_{31}H_{51}BrN_2O_5$ x HCl (632.0): Calc.: C-58.9%; H-5.70%; Br-12.60%; Cl-5.60%; N-4.41%; Found: C-57.7%; H-6.08%; Br-12.57%; Cl-5.60%; N-4.70%.

Example 223

1-(4-Amino-3-bromo-5-tert.butylaminomethyl-benzoyloxy)-4-(3-benzoyl-α-methyl-phenylacetoxy)-n-butane This compound was prepared from 1-(4-amino-3-bromo-5-tert.butylaminomethyl-benzoyloxy)-4-hydroxy-n-butane and 3-benzoyl-α-methyl-phenylacetic acid imidazolide analogous to Example 1. Amorphous substance.

IR-spectrum (methylene chloride):
CO: 1660 cm$^{-1}$
Ester-CO: 1710, 1730 cm$^{-1}$
UV-spectrum (ethanol): λ max 254 nm, 280 nm.

Example 224

1-(4-Amino-3-bromo-5-hexamethyleniminomethyl-benzoyloxy)-4-(3-benzoyl-α-methyl-phenyl-acetoxy)-n-butane This compound was prepared from (1-(4-Amino-3-bromo-5-hexamethyleniminomethyl-benzoyloxy)-4-hydroxy-n-butane and 3-benzoyl-α-methyl-phenylacetic acid imidazolide analogous to Example 1. Amorphous hydrochloride.

$C_{34}H_{39}BrN_2O_5$ x HC (672.1): Calc.: C–60.8%; H-6.0%; Br-11.9%; Cl-5.3%; N-4.2%; Found: C-59.5%; H-6.5%; Br-12.0%; Cl-5.3%; N-4.5%.

Example 225

1-[4-Amino-3-bromo-5-(N-ethyl-cycloheptylaminomethyl)-benzoyloxy]-4-(3-benzoyl-α-methyl-phenylacetoxy)-n-butane This compound was prepared from 1-[4-amino-3-bromo-5-(N-ethyl-cycloheptylaminomethyl)-benzoyloxy]-4-hydroxy-n-butane and 3-benzoyl-α-methyl-phenylacetic acid imidazolide analogous to Example 1. Amorphous hydrochloride.

$C_{37}H_{45}BrN_2O_5$ x HCl (714.2): Calc.: C-62.2%; H-6.5%; Br-11.2%; Cl-5.0%; N-3.9%; Found: C-61.2%; H-6.7%; Br-11.2%; Cl-5.1%; N-4.1%.

Example 226

1-[4-Amino-3-bromo-5-(N-ethyl-cyclopentylaminomethyl)-benzoyloxy]-4-(3-benzoyl-α-methyl-phenylacetoxy)-n-butane This compound was prepared from 1-[4-amino-3-bromo-5-(N-ethyl-cyclopentylaminomethyl)-benzoyloxy]-4-hydroxy-n-butane and 3-benzoyl-α-methyl-phenylacetic acid imidazolide analogous to Example 1. Amorphous hydrochloride.

$C_{35}H_{41}BrN_2O_5$ x HCl (686.1): Calc.: C-61.3%; H-6.2%; Br-11.6%; Cl-5.2%; Found: C-61.7%; H-6.5%; Br-11.4%; Cl-5.1%.

Example 227

1-(4-Amino-3-bromo-5-morpholinomethyl-benzoyloxy)-4-(3-benzoyl-α-methyl-phenylacetoxy)-n-butane This compound was prepared from 1-(4-amino-3-bromo-5-morpholinomethyl-benzoyloxy)-4-hydroxy-n-butane and 3-benzoyl-α-methyl-phenylacetic acid imidazolide analogous to Example 1.

M.p. of the hydrochloride: 148°–150° C.

Example 228

1-[4-Amino-3-bromo-5-(2-diethylaminoethyl-aminomethyl)-benzoyloxy]-2-(3-benzoyl-α-methyl-phenylacetoxy)-ethane This compound was prepared from 1-[4-amino-3-bromo-5-(2-diethylaminoethyl-aminomethyl)-benzoyloxy]-2-hydroxy-ethane and 3-benzoyl-α-methyl-phenylacetic acid imidazolide analogous to Example 1.

M.P. of the hydrochloride: from 70° C. (decomp.).

Example 229

1-(4-Amino-3-bromo-5-diethylaminomethyl-benzoyloxy)-2-(3-benzoyl-α-methyl-phenylacetoxy)-ethane This compound was prepared from 2-(4-amino-3-bromo-5-diethylaminomethyl-benzoyloxy)-ethyl chloride and sodium 3-benzoyl-α-methyl-phenylacetic analogous to Example 8.

M.p. of the hydrochloride: 53°–59° C.

Example 230

1-(4-Amino-3-bromo-5-diethylaminomethyl-benzoyloxy)-3-(3-benzoyl-α-methyl-phenylacetoxy)-n-propane This compound was prepared from 3-(4-amino-3-bromo-5-diethylaminomethyl-benzoyloxy)-n-propyl chloride and sodium 3-benzoyl-α-methylphenylacetate analogous to Example 8. Oil.

IR-spectrum (methylene chloride):
$NH_2$: 3450 cm$^{-1}$
CO: 1660 cm$^{-1}$
Ester-CO: 1710, 1730 cm$^{-1}$
UV-spectrum (ethanol): max 254 nm, 288 nm.

Example 231

1-(4-Amino-3-bromo-5-diethylaminomethyl-benzoyloxy)-4-(3-benzoyl-α-methyl-phenylacetoxy)-n-butane This compound was prepared from 4-(4-amino-3-bromo-5-diethylaminomethyl-benzoyloxy)-n-butyl chloride and sodium 3-benzoyl-α-methyl-phenylacetate analogous to Example 8.

$C_{32}H_{37}BrN_2O_5$ (609): Calc.: C-63.05%; H-6.11%; N-4.59%; Found: C-62/50%; H-6.51%; N-4.42%.

Example 232

2-(4-Amino-3-bromo-5-morpholinomethyl-benzoyloxy)-2'-(3-benzoyl-α-methyl-phenylacetoxy)-diethylsulfide This compound was prepared from 2-(4-amino-3-bromo-5-morpholinomethyl-benzoyloxy)-2'-hydroxy-diethylsulfide and 3-benzoyl-α-methyl-phenylacetic acid analogous to Example 8.

M.p. of the hydrochloride: 146°–149° C.

Example 233

2-(4-Amino-3-bromo-5-morpholinomethyl-benzoyloxy)-2'-(3-benzoyl-α-methyl-phenylacetoxy)-diethyloxide This compound was prepared from 2-(4-Amino-3-bromo-5-morpholinomethyl-benzoyloxy)-2'-hydroxy-diethyloxide and 3-benzoyl-α-methyl-phenylacetic acid analogous to Example 4. Oil.

IR-spectrum (methylene chloride):
Ester-CO: 1710, 1730 cm$^{-1}$
Keto-CO: 1660 cm$^{-1}$
UV-spectrum (ethanol): max 255 nm, 285 nm.

Example 234

1-(4-Amino-3-bromo-5-piperidinomethyl-benzoyloxy)-2-{2-[(2,6-dichlorophenyl)-amino]-phenylacetoxy}-ethane This compound was prepared from 2-(4-Amino-3-bromo-5-piperidinomethyl-benzoyloxy)-ethyl chloride and sodium 2-[(2,6-dichlorophenyl)-amino]-phenylacetate analogous to Example 8.

M.p. of the hydrochloride: 186°–191° C.

Example 235

1-(4-Amino-3-bromo-5-pyrrolidinomethyl-benzoyloxy)-2-{2-[(2,6-dichlorophenyl)-amino]-phenylacetoxy}-ethane This compound was prepared from 2-(4-amino-3-bromo-5-pyrrolidinomethyl-benzoyloxy)-ethylchloride and sodium 2-[(2,6-dichlorophenyl)-amino]phenylacetate analogous to Example 8.

M.p. of the hydrochloride: 186°–187° C.

Example 236

1-[4-amino-3-bromo-5-(N-methyl-cyclohexylaminomethyl)-benzoyloxy]-2-{2-[(2,6-dichlorophenyl)-amino]-phenylacetoxy}-ethane This compound was prepared from 2-[4-amino-3-bromo-5-(N-methyl-cyclohexylaminomethyl)-benzoyloxy]-ethyl chloride and sodium 2-[2,6-dichlorophenyl)-amino]-phenylacetate analogous to Example 8. Oil.

IR-spectrum (methylene chloride):
$NH_2$: 3440 cm$^{-1}$
Ester-CO: 1710 cm$^{-1}$
UV-spectrum (ethanol): λ max 228 nm, 286 nm.

Example 237

1-(4-Amino-3-bromo-5-morpholinomethyl-benzoyloxy)-2-{2-[(2,6-dichlorophenyl)-amino]-phenylacetoxy}-ethane This compound was prepared from 2-(4-amino-3-bromo-5-morpholinomethyl-benzoyloxy)-ethyl chloride and sodium 2-[(2,6-dichlorophenyl)-amino]-phenylacetate analogous to Example 8. Oil.

IR-spectrum (methylene chloride):
$NH_2$: 3440 cm$^{-1}$
Ester-CO: 1710 cm$^{-1}$
UV-spectrum (ethanol): λ max 282 nm.

Example 238

1-[4-Amino-3-bromo-5-(N-cyclohexyl-n-propylaminomethyl)-benzoyloxy]-2-{2-[(2,6-dichlorophenyl)-amino]-phenylacetoxy}-ethane This compound was prepared from 2-[4-amino-3-bromo-5-(N-cyclohexyl-n-propylaminomethyl)-benzoyloxy]-ethyl chloride and sodium 2-[(2,6-dichlorophenyl)-amino-phenylacetate analogous to Example 8.
M.p.: 110.5°-112° C.

Example 239

1-[4-Amino-3-bromo-5-(N-ethyl-cycloheptylaminomethyl)-benzoyloxy]-2-{2-[(2,6-dichlorophenyl)-amino]-phenylacetoxy}-ethane This compound was prepared from 2-[4-amino-3-bromo-5-(N-ethyl-cycloheptylaminomethyl)-benzoyloxy]-ethyl chloride and sodium 2-[(2,6-dichlorophenyl)-amino]-phenylacetate analogous to Example 8. oil.
UR-spectrum (methylene chloride):
NH$_2$: 3440 cm$^{-1}$
Ester-CO: 1710 cm$^{-1}$
UV-spectrum (ethanol): λ max 285 nm.

Example 240

1-[4-Amino-3-bromo-5-(N-ethyl-cyclopentylaminomethyl)-benzoyloxy]-2-{2-[(2,6-dichlorophenyl)-amino]-phenylacetoxy}-ethane This compound was prepared from 2-[4-amino-3-bromo-5-(N-ethyl-cyclopentylaminomethyl)-benzoyloxy]-ethyl chloride and sodium 2-[(2,6-dichlorophenyl)-amino]-phenylacetate analogous to Example 8. Oil.
IR-spectrum (methylene chloride):
NH$_2$: 3440 cm$^{-1}$
Ester-CO: 1710 cm$^{-1}$
UV-spectrum (ethanol): λ max 285 nm.

Example 241

1-[4-amino-3-bromo-5-tert.butylaminomethyl-benzoyloxy]-2-{2-[(2,6-dichlorophenyl)-amino]-phenylacetoxy}-ethane This compound was prepared from 2-(4-amino-3-bromo-5-tert.butylaminomethyl-benzoyloxy)-ethyl chloride and sodium 2-[(2,6-dichlorophenyl)-amino]-phenylacetate analogous to Example 8.
M.p. of the hydrochloride: 224°-225° C.

Example 242

1-(4-Amino-3-bromo-5-dimethylaminomethyl-benzoyloxy)-2-{2-[(2,6-dichlorophenyl)-amino]-phenylacetoxy}-ethane This compound was prepared from 2-(4-amino-3-bromo-5-dimethylaminomethyl-benzoyloxy)-ethyl chloride and sodium 2-[(2,6-dichlorophenyl)-amino]-phenylacetate analogous to Example 8.
M.p. of the hydrochloride: 130.5°-132° C.

Example 243

1-(4-Amino-3-bromo-5-hexamethyleniminomethyl-benzoyloxy)-2-{2-[(2,6-dichlorophenyl)-amino]-phenylacetoxy}-ethane This compound was prepared from 2-(4-amino-3-bromo-5-hexamethyleniminomethyl-benzoyloxy)-ethyl chloride and sodium 2-[(2,6-dichlorophenyl)-amino]-phenylacetate analogous to Example 8.
M.p. of the hydrochloride: 182°-183° C.

Example 244

1-[2-Amino-3-bromo-5-(N-ethyl-cyclohexylaminomethyl)-benzoyloxy]-2-{2-[(2,6-dichlorophenyl)-amino]-phenylacetoxy}-ethane This compound was prepared from 1-[2-amino-3-bromo-5-(N-ethyl-cyclohexylaminomethyl)-benzoyloxy]-2-hydroxy-ethane and sodium 2-[(2,6-dichlorophenyl)-amino]-phenylacetate analogous to Example 4. Oil.
IR-spectrum (methylene chloride):
Ester-CO: 1690, 1725 cm$^{-1}$
UV-spectrum (ethanol): λ max 222 nm, 275 nm, 348 nm.

Example 245

1-(2-Amino-3-bromo-5-diethylaminomethyl-benzoyloxy)-2-{2-[(2,6-dichlorophenyl)-amino]-phenylacetoxy}-ethane This compound was prepared from 1-(2-amino-3-bromo-5-diethylaminomethyl-benzoyloxy)-2-hydroxy-ethane and sodium 2-[(2,6-dichlorophenyl)-amino]-phenylacetate analogous to Example 4. Oil.
UR-spectrum (methylene chloride):
Ester-CO: 1730, 1690 cm$^{-1}$
N-alkyl: 2810 cm$^{-1}$
UV-spectrum (ethanol): λ max 223 nm, 276 nm, 346 nm.

Example 246

1-[4-Amino-3-bromo-5-(N-ethyl-cyclohexylaminomethyl)-benzamido]-3-{2-[(2,6-dichlorophenyl)-amino]-phenylacetoxy}-n-propane This compound was prepared from 3-[4-amino-3-bromo-5-(N-ethyl-cyclohexylaminomethyl)-benzamido]-n-propyl chloride and sodium 2-[(2,6-dichlorophenyl)-amino]-phenylacetate analogous to Example 8.
M.p.: 148°-150° C.

Example 247

1-[4-Amino-3-bromo-5-(N-ethyl-cycloheptylaminomethyl)-benzoyloxy]-4-{2-[(2,6-dichlorophenyl)-amino]-phenylacetoxy}-n-butane This compound was prepared from 4-[4-amino-3-bromo-5-(N-ethyl-cycloheptylaminomethyl)-benzoyloxy]-n-butyl chloride and sodium 2-[(2,6-dichlorophenyl)-amino]-phenylacetate analogous to Example 8.
$C_{35}H_{42}BrCl_2N_3O_4$ (719): Calc.: C-58.42%; H-5.88%; Br-11.11%; Cl-9.86%; N-5.84%; Found: C-58.97%; H-5.77%; Br-10.84%; Cl-9.61%; N-5.71%.

Example 248

1-[4-Amino-3-bromo-5-(N-cyclohexyl-n-propylaminomethyl)-benzoyloxy]-4-{2-[(2,6-dichlorophenyl)-amino]-phenylacetoxy}-n-butane This compound was prepared from 4-[4-amino-3-bromo-5-(N-cyclohexyl-n-propylaminomethyl)-benzoyloxy]-n-butyl chloride and sodium 2-[(2,6-dichlorophenyl)-amino]-phenylacetate analogous to Example 8. Oil.
$C_{35}H_{42}BrCl_2N_3O_4$ (719): Calc.: C-58.42%; H-5.88%; Br-11.11%; Cl-9.86%; N-5.84%; Found: C-58.16%; H-6.03%; Br-10.95%; Cl-9.73%; N-5.84%.

Example 249

1-(4-Amino-3-bromo-5-hexamethyleniminomethyl-benzoyloxy)-4-{2-[(2,6-dichlorophenyl)-amino]-phenylacetoxy}-n-butane This compound was prepared from 4-(4-amino-3-bromo-5-hexamethyleniminomethyl-benzoyloxy)-n-butyl chloride and sodium 2-[(2,6-dichlorophenylamino]-phenylacetate analogous to Example 8.
M.p. of the hydrochloride: 122°-125° C.

Example 250

1-(4-Amino-3-bromo-5-tert.butylaminomethyl-benzoyloxy)-4-{2-[(2,6-dichlorophenyl)-amino]-phenylacetoxy}-n-butane This compound was prepared from 4-(4-amino-3-bromo-5-tert.butylaminomethyl-benzoyloxy)-n-butyl chloride and sodium 2-[(2,6-dichlorophenyl)-amino]-phenylacetate analogous to Example 8.
M.p. of the hydrochloride: 122°-124° C.

Example 251

1-[4-Amino-3-bromo-5-(N-methyl-cyclohexylaminomethyl)-benzoyloxy]-4-{2-[(2,6-dichlorophenyl)-amino]-phenylacetoxy}-n-butane This compound was prepared from 4-[4-amino-3-bromo-5-(N-methyl-cyclohexylaminomethyl)-benzoyloxy]-n-butyl chloride and sodium 2-[(2,6-dichlorophenyl)-amino]-phenylacetate analogous to Example 8.
M.p. of the hydrochloride: 145°-147° C.

Example 252

1-(4-Amino-3-bromo-5-dimethylaminomethyl-benzoyloxy)-4-{2-[(2,6-dichlorophenyl)-amino]-phenylacetoxy}-n-butane This compound was prepared from B 4-(4-amino-3-bromo-5-dimethylaminomethyl-benzoyloxy)-n-butyl chloride and sodium 2-[(2,6-dichlorophenylamino]-phenylacetate analogous to Example 8.
M.p. of the hydrochloride: 87°-90° C.

Example 253

1-(4-Amino-3-bromo-5-pyrrolidinomethyl-benzoyloxy)-4-{2-[(2,6-dichlorophenyl)-amino]-phenylacetoxy}-n-butane This compound was prepared from 4-(4-amino-3-bromo-5-pyrrolidinomethyl-benzoyloxy)-n-butyl chloride and sodium 2-[(2,6-dichlorophenyl)-amino]-phenylacetate analogous to Example 8.
M.p. of the hydrochloride: 143°-145° C.

Example 254

1-(4-Amino-3-bromo-5-morpholinomethyl-benzoyloxy)-4-{2-[(2,6-dichlorophenyl)-amino]-phenylacetoxy}-n-butane This compound was prepared from 4-(4-amino-3-bromo-5-morpholinomethyl-benzoyloxy)-n-butyl chloride and sodium 2-[(2,6-dichlorophenyl)-amino]-phenylacetate analogous to Example 8.
M.p. of the hydrochloride: 174°-176° C.

Example 255

1-(4-Amino-3-bromo-5-piperidinomethyl-benzoyloxy)-4-{2-[(2,6-dichlorophenyl)-amino}-phenylacetoxy}-n-butane This compound was prepared from 4-(4-amino-3-bromo-5-piperidinomethyl-benzoyloxy)-n-butyl chloride and sodium 2-[(2,6-dichlorophenylamino]-phenylacetate analogous to Example 8.
M.p. of the hydrochloride: 184°-185° C.

Example 256

1-[4-Amino-3-bromo-5-(N-methyl-n-propylaminomethyl)-benzoyloxy]-4-{2-[(2,6-dichlorophenyl)-amino]-phenylacetoxy}-n-butane This compound was prepared from 4-[4-amino-3-bromo-5-(N-methyl-n-propylaminomethyl)-benzoyloxy]-n-butyl chloride and sodium 2-[(2,6-dichlorophenyl)-amino]-phenylacetate analogous to Example 8.
IR-spectrum (methylene chloride):
$NH_2$: 3450 cm$^{-1}$
Ester-CO: 1700 cm$^{-1}$
UV-spectrum (ethanol): λ max 282 nm.

Example 257

1-[4-Amino-3-bromo-5-(N-methyl-benzylaminomethyl)-benzoyloxy]-4-{2-[(2,6-dichlorophenyl)-amino]-phenylacetoxy}-n-butane This compound was prepared from 4-[4-amino-3-bromo-5-(N-methyl-benzylaminomethyl)-benzoyloxy]-n-butyl chloride and sodium 2-[(2,6-dichlorophenyl)-amino]-phenylacetate analogous to Example 8.
IR-spectrum (methylene chloride):
$NH_2$: 3445 cm$^{-1}$
Ester-CO: 1700 cm$^{-1}$
UV-spectrum (ethanol): λ max 283 nm.

Example 258

1-(4-Amino-3-bromo-5-cyclohexylaminomethyl-benzoyloxy)-4-{2-[(2,6-dichlorophenyl)-amino]-phenylacetoxy}-n-butane This compound was prepared from 4-(4-amino-3-bromo-5-cyclohexylaminomethyl-benzoyloxy)-n-butyl chloride and sodium 2-[(2,6-dichlorophenyl)-amino]-phenylacetate analogous to Example 8.
M.p. of the hydrochloride: 166°-168° C.

Example 259

1-(4-Amino-3-bromo-5-isopropylaminomethyl-benzoyloxy)-4-{2-[(2,6-dichlorophenyl)-amino]-phenylacetoxy}-n-butane This compound was prepared from 4-(4-amino-3-bromo-5-isopropylaminomethyl-benzoyloxy)-n-butyl chloride and sodium 2-[(2,6-dichlorophenyl)-amino]-phenylacetate analogous to Example 8.
IR-spectrum (methyl chloride):
$NH_2$: 3340 cm$^{-1}$
Ester-CO: 1705 cm$^{-1}$
UV-spectrum (ethanol): λ max 282 nm.

Example 260

1-[4-Amino-3-bromo-5-(N-ethyl-cyclohexylaminomethyl)-benzamido-4-{2-[(2,6-dichlorophenyl)-amino]-phenylacetoxy}-n-butane This compound was prepared from 4-[4-amino-3-bromo-5-(N-ethyl-cyclohexylaminomethyl)-benzamido]-n-butyl chloride and sodium 2-[(2,6-dichlorophenyl)-amino]-phenylacetate analogous to Example 8. Amorphous hydrochloride.

IR-spectrum (methylene chloride):
Ester-CO: 1720 cm$^{-1}$
Amide-CO: 1640 cm$^{-1}$
UV-spectrum (ethanol): λ max 275 nm.

Example 261

1-[4-Amino-3-bromo-5-(N-methyl-benzylaminomethyl)-benzoyloxy]-5-{2-[(2,6-dichlorophenyl)-amino]-phenylacetoxy}-n-pentane This compound was prepared from 5-[4-amino-3-bromo-5-(N-methyl-benzylaminomethyl)-benzoyloxy]-n-pentyl chloride and sodium 2-[(2,6-dichlorophenyl)-amino]-phenylacetate analogous to Example 8 Oil.

IR-spectrum (methylene chloride):
NH$_2$: 3450 cm$^{-1}$
Ester-CO: 1700 cm$^{-1}$
UV-spectrum (ethanol): λ max 283 nm.

Example 262

1-(4-Amino-3-bromo-5-isopropylaminomethyl-benzoyloxy)-5-{2-[(2,6-dichlorophenyl)-amino]-phenylacetoxy}-n-pentane This compound was prepared from 5-(4-amino-3-bromo-5-isopropylaminomethyl-benzoyloxy)-n-pentyl chloride and sodium 2-[(2,6-dichlorophenyl)-amino]-phenylacetate analogous to Example 8. Oil.

IR-spectrum (methylene chloride):
NH$_2$: 3450 cm$^{-1}$
Ester-CO: 1705 cm$^{-1}$
UV-spectrum (ethanol): λ max 283 nm.

Example 263

1-(4-Amino-3-bromo-5-cyclohexylaminomethyl-benzoyloxy)-5-{2-[(2,6-dichlorophenyl)-amino]-phenylacetoxy}-n-pentane This compound was prepared from 5-(4-amino-3-bromo-5-cyclohexylaminomethyl-benzoyloxy)-n-pentyl chloride and sodium 2-[(2,6-dichlorophenyl)-amino]-phenylacetate analogous to Example 8.

M.p. of the hydrochloride: 152°-153° C.

Example 264

1-[4-Amino-3-bromo-5-(N-methyl-n-propylaminomethyl)-benzoyloxy]-5-{2-[(2,6-dichlorophenyl)-amino]-phenylacetoxy}-n-pentane This compound was prepared from 5-[4-amino-3-bromo-5-(N-methyl-n-propylaminomethyl)-benzoyloxy]-n-pentyl chloride and sodium 2-[(2,6-dichlorophenyl)-amino]-phenylacetate analogous to Example 8.

M.p. of the hydrochloride: 50°-60° C.

Example 265

1-(4-Amino-3-bromo-5-piperidinomethyl-benzoyloxy)-5-{2-[(2,6-dichlorophenyl)-amino]-phenylacetoxy}-n-pentane This compound was prepared from 5-(4-Amino-3-bromo-5-piperidinomethyl-benzoyloxy)-n-pentyl chloride and sodium 2-[(2,6-dichlorophenyl)-amino]-phenylacetate analogous to Example 8.

M.p. of the hydrochloride: 183°-185° C.

Example 266

1-[4-Amino-3-bromo-5-(N-methyl-piperazinomethyl)-benzoyloxy]-5-{2-[(2,6-dichlorophenyl)-amino]-phenylacetoxy}-n-pentane This compound was prepared from 5-[amino-3-bromo-5-(N-methyl-piperazinomethyl)-benzoyloxy]-n-pentyl chloride and 2-[(2,6-dichlorophenyl)-amino]-phenylacetate analogous to Example 8.

M.p. of the hydrochloride: 193°-196° C.

Example 267

1-(4-Amino-3-bromo-5-morpholinomethyl-benzoyloxy)-5-{2-[(2,6-dichlorophenyl)-amino]-phenylacetoxy}-n-pentane This compound was prepared from 5-(4-amino-3-bromo-5-morpholinomethyl-benzoyloxy)-n-pentyl chloride and sodium 2-[(2,-dichlorophenyl)-amino]-phenylacetate analogous to Example 8.

M.p. of the hydrochloride: 185°-187° C.

Example 268

1-(4-Amino-3-bromo-5-pyrrolidinomethyl-benzoyloxy)-5-{2-[(2,6-dichlorophenyl)-amino]-phenylacetoxy}-n-pentane This compound was prepared from 5-(4-amino-3-bromo-5-pyrrolidinomethyl-benzoyloxy)-m-pentyl chloride and sodium 2-[(2,6-dichlorophenyl)-amino]-phenylacetate analogous to Example 8.

M.p. of the hydrochloride: 152°-153° C.

Example 269

1-(4-Amino-3-bromo-5-dimethylaminomethyl-benzoyloxy)-5-{2-[(2,6-dichlorophenyl)-amino]-phenylacetoxy}-n-pentane This compound was prepared from 5-(4-amino-3-bromo-5-dimethylaminomethyl-benzoyloxy)-n-pentyl chloride and sodium 2-[(2,6-dichlorophenyl)-amino]-phenylacetate analogous to Example 8.

M.p. of the hydrochloride: 140°-144° C.

Example 270

1-[4-Amino-3-bromo-5-(N-methyl-cyclohexylaminomethyl)-benzoyloxy]-5-{2-[(2,6-dichlorophenyl)-amino]-phenylacetoxy}-n-pentane This compound was prepared from 5-[4-amino-3-bromo-5-(N-methyl-cyclohexylaminomethyl)-benzoyloxy]-n-pentyl chloride and sodium 2-[(2,6-dichlorophenyl)-amino]-phenylacetate analogous to Example 8.

M.p. of the hydrochloride: 105°-110° C.

Example 271

1-(4-Amino-3-bromo-5-tert.butylaminomethyl-benzoyloxy)-5-{2-[(2,6-dichlorophenyl)-amino]-phenylacetoxy}-n-pentane This compound was prepared from 5-(4-Amino-3-bromo-5-tert. butylaminomethyl-benzoyloxy)-n-pentyl chloride and sodium 2-[(2,6-dichlorophenyl)-amino]-phenylacetate analogous to Example 8.

M.p. of the hydrochloride: 109°-111° C.

Example 272

1-(4-Amino-3-bromo-5-hexamethyleniminomethyl-benzoyloxy)-5-{2-[(2,6-dichlorophenyl)-amino]-phenylacetoxy}-n-pentane This compound was prepared from 5-(4-amino-3-bromo-5-hexamethyleniminomethyl-benzoyloxy)-n-pentyl chloride and sodium 2-[(2,6-dichlorophenyl)-amino]-phenylacetate analogous to Example 8.

M.p. of the hydrochloride: 149°-150° C.

Example 273

1-[4-Amino-3-bromo-5-(N-cyclohexyl-n-propylaminomethyl)-benzoyloxy]-5-{2-[(2,6-dichlorophenyl)-amino]-phenylacetoxy}-n-pentane This compound was prepared from 5-[4-amino-3-bromo-5-(N-cyclohexyl-n-propylaminomethyl)-benzoyloxy]-n-pentyl chloride and sodium 2-[(2,6-dichlorophenyl)-amino]-phenylacetate analogous to Example 8.

M.p. of the hydrochloride: 113°-115° C.

Example 274

1-[2-Amino-3-bromo-5-(N-ethyl-cyclohexylaminomethyl)-benzoyloxy]-5-{2-[(2,6-dichlorophenyl)-amino]-phenylacetoxy}-n-pentane This compound was prepared from 1-[2-amino-3-bromo-5-(N-ethyl-cyclohexylaminomethyl)-benzoyloxy]-5-hydroxy-n-pentane and 2-[(2,6-dichlorophenyl)-amino]-phenylacetic acid analogous to Example 4. Oil.

IR-spectrum (methylene chloride):
Ester-CO: 1685, 1710 cm$^{-1}$
N-alkyl: 2830 cm$^{-1}$ UV-spectrum (ethanol): λ max 223 nm, 275 nm, 348 nm.

Example 275

1-[4-Amino-3-bromo-5-(N-ethyl-cyclohexylaminomethyl)-benzamido]-5-{2-[(2,6-dichlorophenyl)-amino]-phenylacetoxy}-n-pentane This compound was prepared from 5-[4-amino-3-bromo-5-(ethyl-cyclohexylaminomethyl)-benzamido]-n-pentyl chloride and sodium 2-[(2,6-dichlorophenyl)-amino]-phenylacetate analogous to Example 8. Amorphous dihydrochloride.

IR-spectrum (methylene chloride):
Ester-CO: 1720 cm$^{-1}$
Amide-CO: 1640 cm$^{-1}$ UV-spectrum (ethanol): λ max 275 nm.

Example 276

1-(4-Amino-3-bromo-5-diethylaminomethyl-benzoyloxy)-6-{2-[(2,6-dichlorophenyl)-amino]-phenylacetoxy}-hexane This compound was prepared from 6-(4-amino-3-bromo-5-diethylaminomethyl-benzoyloxy)-n-hexyl chloride and sodium 2-[(2,6-dichlorophenyl)-amino]-phenylacetate analogous to Example 8.

M.p. of the hydrochloride: 63°-69° C.

Example 277

1-[4-Amino-3-bromo-5-(N-ethyl-cyclohexylaminomethyl)-benzamido]-6-{2-[(2,6-dichlorophenyl)-amino]-phenylacetoxy}-n-hexane This compound was prepared from 6-[4-amino-3-bromo-5-(N-ethyl-cyclohexylaminomethyl)-benzamido]-n-hexyl chloride and sodium 2-[(2,6-dichlorophenyl)-amino]-phenyl)-amino]-phenylacetate analogous to Example 8. Amorphous hydrochloride.

$C_{36}H_{45}BrCl_2N_4O_3$ (769.1): Calc.: C-56.22%; H-6.03%; Br-10.39%; Cl-13.83%; N-7.28% Found: C-56.69%; H-6.23%; Br-10.15%; Cl-13.54%; N-7.25%

Example 278

1-[4-Amino-3-bromo-5-(N-ethyl-cyclohexylaminomethyl)-benzoyloxy]-7-{2-[(2,6-dichlorophenyl)-amino]-phenylacetoxy}-n-heptane This compound was prepared from 7-[4-amino-3-bromo-5-(N-ethyl-cyclohexylaminomethyl)-benzoyloxy]-n-heptyl chloride and sodium 2-[(2,6-dichlorophenyl)-amino]-phenylacetate analogous to Example 8.

M.p. of the hydrochloride: 96°-100° C.

Example 279

1-[4-Amino-3-bromo-5-(N-ethyl-cyclohexylaminomethyl)-benzoyloxy]-8-{2-[(2,6-dichlorophenyl)-amino]-phenylacetoxy}-n-octane This compound was prepared from 8-(4-amino-3-bromo-5-(N-ethyl-cyclohexylaminomethyl)-benzoyloxy]-n-octyl chloride and sodium 2-[(2,6-dichlorophenyl)-amino]-phenylacetate analogous to Example 8.

M.p. of the hydrochloride: 131°-133° C.

Example 280

1-[4-Amino-3-bromo-5-(N-ethyl-cyclohexylaminomethyl)-benzoyloxy]-9-{2-[(2,6-dichlorophenyl)-amino]-phenylacetoxy}-n-nonane This compound was prepared from 9-[4-amino-3-bromo-5-(N-ethyl-cyclohexylaminomethyl)-benzoyloxy]-n-nonyl chloride and sodium 2-[(2,6-dichlorophenyl)-amino]-phenylacetate analogous to Example 8.

M.p. of the hydrochloride: 106°-108° C.

Example 281

1-[4-Amino-3-bromo-5-(N-ethyl-cyclohexylaminomethyl)-benzoyloxy]-10-{2-[(2,6-dichlorophenyl)-amino]-phenylacetoxy}-n-decane This compound was prepared from 10-[4-amino-3-bromo-5-(N-ethyl-cyclohexylaminomethyl)-benzoyloxy]-n-decyl chloride and sodium 2-[(2,6-dichlorophenyl)-amino]-phenylacetate analogous to Example 8.

M.p. of the hydrochloride: 125°-127° C.

Example 282

2-(4-Amino-3-bromo-5-piperidinomethyl-benzoyloxy)-2'-{2-[(2,6-dichlorophenyl)-amino]-phenylacetoxy}-diethylsulfide This compound was prepared from 2-(4-amino-3-bromo-5-piperidinomethyl-benzoyloxy)-2'-hydroxy-diethylsulfide and 2-[(2,6dichlorophenyl)-amino]-phenylacetic acid analogous to Example 4.

M.p. of the hydrochloride: 135°-138° C.

Example 283

2-(4-Amino-3-bromo-5-piperidinomethyl-benzoyloxy)-2'-{2-[(2,6-dichlorophenyl)-amino]-phenylacetoxy}-diethyloxide This compound was prepared from 2-(4-amino-3-bromo-5-piperidinomethyl-benzoyloxy)-2'-hydroxy-diethyloxide and 2-[(2,6-dichlorophenyl)-amino]-phenylacetic acid analogous to Example 4. Oil.

$C_{31}H_{34}BrCl_2N_3O_5$ (679.5): Calc.: C-54.80%; H-5.04%; Br-11.76%; Cl-10.44%; N-6.18%; Found: C-54.50%; H-5.18%; Br-11.75%; Cl-10.44%; N-6.27%.

Example 284

2-(4-Amino-3-bromo-5-hexamethyleniminomethyl-benzoyloxy)-2'-{[(2,6-dichlorophenyl)-amino]-phenylacetoxy}-diethyloxide This compound was prepared from 2-(4-amino-3-bromo-5-hexamethyleniminomethyl-benzoyloxy)-2'-hydroxy-diethyloxide and 2-[(2,6-dichlorophenyl)-amino]-phenylacetic acid analogous to Example 4. Oil.

$C_{32}H_{36}BrCl_2N_3O_5$ (693.5): Calc.: C-55.42%; H-5.23%; Br-11.52%; Cl-10.23%; N-6.06%; Found: C-55.77%; H-5.23%; Br-11.20%; Cl-9.93%; N-5.78%.

Example 285

2-(4-Amino-3-bromo-5-dimethylaminomethyl-benzoyloxy)-2'-{2-[(2,6-dichlorophenyl)-amino]-phenylacetoxy}-diethyloxide This compound was prepared from 2-(4-amino-3-bromo-5-diethylaminomethyl-benzoyloxy)-2'-hydroxy-diethyloxide and 2-[(2,6-dichlorophenyl)-amino]-phenylacetic acid analogous to Example 4. Oil.

IR-spectrum (methylene chloride):
Ester-CO: 1710 cm$^{-1}$
NH$_2$: 3450 cm$^{-1}$
UV-spectrum (ethanol): λ max 280 nm.

Example 286

2-(4-Amino-3-bromo-5-diethylaminomethyl-benzoyloxy)-2'-{2-[(2,6-dichlorophenyl)-amino]-phenylacetoxy}-diethylsulfide This compound was prepared from 2-(4-amino-3-bromo-5-diethylaminomethyl-benzoyloxy)-2'-hydroxy-diethylsulfide and 2-[(2,6-dichlorophenyl)-amino]-phenylacetic acid analogous to Example 4. Oil.

IR-spectrum (methylene chloride):
Ester-CO: 1710 cm$^{-1}$
NH$_2$: 3450 cm$^{-1}$
UV-spectrum (ethanol): λ max 283 nm.

Example 287

N-[2-(4-Amino-3-bromo-5-diethylaminomethyl-benzoyloxy)-ethyl]-N-{2-[2-[(2,6-dichlorophenyl)-amino]-phenylacetoxy]-ethyl}-ethylamine This compound was prepared from N-[2-(4-amino-3-bromo-5-diethylaminomethyl-benzoyloxy)-ethyl]-N-(2-hydroxyethyl)-ethylamine and 2-[(2,6-dichlorophenyl)-amino]-phenylacetic acid analogous to Example 4. Oil.

IR-spectrum (methylene chloride):
Ester-CO: 1710 cm$^{-1}$
N-alkyl: 2820 cm$^{-1}$
NH$_2$: 3450 cm$^{-1}$
UV-spectrum (ethanol): λ max 283 nm.

Example 288

1-(4-Amino-3-bromo-5-diethylaminomethyl-benzoyloxy)-6-[(+)-6-methoxy-α-methyl-2-naphthaline-acetoxy]-n-hexane This compound was prepared from 6-(4-amino-3-bromo-5-diethylaminomethyl-benzoyloxy)-n-hexyl chloride and sodium (+)-6-methoxy-α-methyl-2-naphthaline-acetate analogous to Example 8. Oil.

IR-spectrum (methylene chloride):
OCH$_3$ 2830 cm$^{-1}$
Ester-CO 1700, 1730 cm$^{-1}$ UV-spectrum (ethanol): λ max 230 nm, 282 nm.

Example 289

1-(2-Amino-3-bromo-5-diethylaminomethyl-benzoyloxy)-2-[1-(4-chlorobenzoyl)-5-methoxy-2-methyl-1H-indole-3-acetoxy]-ethane This compound was prepared from 1-(2-Amino-3-bromo-5-diethylaminomethyl-benzoyloxy)-2-hydroxy-ethane and 1-(4-chlorobenzoyl)-5-methoxy-2-methyl-1H-indole-3-acetic acid analogous to Example 4. Oil.

$C_{33}H_{35}BrClN_3O_6$ (685.0): Calc.: C-57.86%; H-5.15%; Br-11.67%; Cl-5.18%; N-6.13%; Found: C-57.99%; H-5.18%; Br-11.43%; Cl-5.07%; N-6.09%

Example 290

1-[4-Amino-3-chloro-5-(N-ethyl-cyclohexylaminomethyl)-benzoyloxy]-2-[1-(4-chlorobenzoyl)-5-methoxy-2-methyl-1H-indole-3-acetoxy]-ethane This compound was prepared from 4-amino-3-chloro-5-(N-ethyl-cyclohexylaminomethyl)-benzoyl chloride and 1-[1-(4-chlorobenzoyl)-5-methoxy-2-methyl-1H-indole-3-acetoxy]-2-hydroxy-ethane analogous to Example 7. Amorphous hydrochloride.

IR-spectrum (methylene chloride):
Ester-CO: 1710, 1735 cm$^{-1}$
Amide-CO: 1680 cm$^{-1}$
UV-spectrum (ethanol): λ max 228 nm (shoulder), 276 nm.

Example 291

1-[2-Amino-3-bromo-5-(N-ethyl-cyclohexylaminomethyl)-benzoyloxy]-2-[1-(4-chlorobenzoyl)-5-methoxy-2-methyl-1H-indole-2-acetoxy]-ethane This compound was prepared from 1-[2-amino-3-bromo-5-(N-ethyl-cyclohexylaminomethyl)-benzoyloxy]-2-hydroxy-ethane and 1-(4-chlorobenzoyl)-5-methoxy-2-methyl-1H-indole-3-acetic acid analogous to Example 4. Oil.

$C_{37}H_{41}BrClN_3O_6$ (739.1): Calc.: C-60.13%; H-5.39%; Br-10.81%; Cl-4.80%; N-5.69%; Found: C-60.16%; H-5.55%; Br-11.04%; Cl-4.90%; N-5.86%.

Example 292

1-(4-Amino-3-chloro-5-diethylaminomethyl-benzoyloxy)-2-[1-(4-chlorobenzoyl)-5-methoxy-2-methyl-1H-indole-3-acetoxy]-ethane This compound was prepared from 4-amino-3-chloro-5-diethylaminomethyl-benzoyl chloride and 1-[1-(4-chlorobenzoyl)-5-methoxy-2-methyl-1H-indole-3-acetoxy]-2-hydroxyethane analogous to Example 7. Amorphous hydrochloride.

IR-spectrum (methylene chloride):
Ester-CO: 1710, 1725 cm$^{-1}$
Amide-CO: 1680 cm$^{-1}$
UV-spectrum (ethanol): λ max 228 nm (shoulder), 275 nm.

Example 293

1-[4-Amino-3-bromo-5-(N-ethyl-cyclohexylaminomethyl)-benzoyloxy]-2-methyl-2-n-propyl-3-[1-(4-chlorobenzoyl)-5-methoxy-2-methyl-1H-indole-3-acetoxy]-n-propane This compound was prepared from 1-[4-amino-3-bromo-5-(N-ethyl-cyclohexylaminomethyl)-benzoyloxy]-2-methyl-2-n-propyl-3-hydroxy-n-propane and 1-(4- chlorobenzoyl)-5-methoxy-2-methyl-1H-indole-3-acetic acid analogous to Example 4. Oil.

IR-spectrum (methylene chloride):
NH$_2$: 3450 cm$^{-1}$
N-Alkyl: 2940 cm$^{-1}$
O-CH$_3$: 2860 cm$^{-1}$
Ester-CO: 1705, 1735 cm$^{-1}$
Amide-CO: 1685 cm$^{-1}$

Example 294

1-[4-Amino-3-bromo-5-(N-ethyl-cyclohexylaminomethyl)-benzoyloxy]-2-[1-(4-chlorobenzoyl)-5-methoxy-2-methyl-1H-indole-3-acetoxy]-2-phenyl-ethane This compound was prepared from 1-[4-amino-3-bromo-5-(N-ethyl-cyclohexylaminomethyl)-benzoyloxy]-2-phenyl-2-hydroxy-ethane and 1-(4-chlorobenzoyl)-5-methoxy-2-methyl-1H-indole-3-acetic acid analogous to Example 4. Oil.

IR-spectrum (methylene chloride):
NH$_2$ 3440 cm$^{-1}$
N-Alkyl: 2940 cm$^{-1}$
OCH$_3$: 2860 cm$^{-1}$
Ester-CO: 1710, 1745 cm$^{-1}$
UV-spectrum (ethanol): λ max 230 nm, 295 nm.

Example 295

1-[4-Amino-3-bromo-5-(N-ethyl-cyclohexylaminomethyl)-benzoyloxy]-2-[1-(4-chlorobenzoyl)-5-methoxy-2-methyl-1H-indole-3-acetoxy]-1,2-diphenyl-ethane This compound was prepared from 1-[4-amino-3-bromo-5-(N-ethyl-cyclohexylaminomethyl)-benzoyloxy]-1,2-diphenyl-2-hydroxy-ethane and 1-(4-chlorobenzoyl)-5-methoxy-2-methyl-1H-indole-3-acetic acid analogous to Example 4. Oil.

IR-spectrum (methylene chloride):
NH$_2$: 3450 cm$^{-1}$
N-Alkyl: 2930 cm$^{-1}$
O-CH$_3$: 2860 cm$^{-1}$
Ester-CO: 1710, 1740 cm$^{-1}$
Amide-CO: 1685 cm$^{-1}$
UV-spectrum (ethanol): λ max 225 nm, 288 nm.

Example 296

1-[4-Amino-3-bromo-5-(N-ethyl-cyclohexylaminomethyl)-benzoyloxy]-2-[1-(4-chlorobenzoyl)-5-methoxy-2-methyl-1H-indole-3-acetoxy]-1-phenyl-ethane This compound was prepared from 1-[4-amino-3-bromo-5-(N-ethyl-cyclohexylaminomethyl)-benzoyloxy]-1-phenyl-2-hydroxy-ethane and 1-(4-chlorobenzoyl)-5-methoxy-2-methyl-1H-indole-3-acetic acid analogous to Example 4. Oil.

IR-spectrum (methylene chloride):
NH$_2$: 3440 cm$^{-1}$
N-Alkyl: 2915 cm$^{-1}$
O-CH$_3$: 2850 cm$^{-1}$
Ester-CO: 1710, 1740 cm$^{-1}$
Amide-CO: 1685 CM$^{-1}$
UV-spectrum (ethanol): λ max 230 nm, 288 nm.

Example 297

2-[4-Amino-3-bromo-5-(N-ethyl-cyclohexylaminomethyl)-benzoyloxymethyl]-6-[1-(4-chlorobenzoyl)-5-methoxy-2-methyl-1H-indole-3-acetoxymethyl]-pyridine This compound was prepared from 2-[4-amino-3-bromo-5-(N-ethyl-cyclohexylaminomethyl)-benzoyloxymethyl]-6-hydroxymethyl-pyridine and 1-(4-chlorobenzoyl)-5-methoxy-2-methyl-1H-indole-3-acetic acid analogous to Example 4. Oil.

IR-spectrum (methylene chloride):
NH$_2$ 3440 cm$^{-1}$
N-Alkyl 2930 cm$^{-1}$
O-CH$_3$ 2850 cm$^{-1}$
Ester-CO 1710, 1735 cm$^{-1}$
Amide-CO 16.85 cm$^{-1}$
UV-spectrum (ethanol): λ max 230 nm, 285 nm.

EXAMPLE 298

1-[4-Amino-3-bromo-5-(N-ethyl-cyclohexylaminomethyl)-benzoyloxymethyl]-4-[1-(4-chlorobenzoyl)-5-methoxy-2-methyl-1H-indole-3-acetoxymethyl]-benzene This compound was prepared from 1-[4-amino-3-bromo-5-(N-ethyl-cyclohexylaminomethyl)-benzoyloxymethyl]-4-hydroxymethyl-benzene and 1-(4-chlorobenzoyl)-5-methoxy-2-methyl-1H-indole-3-acetic acid analogous to Example 4. Oil.

IR-spectrum (methylene chloride):
NH$_2$ 3450 cm$^{-1}$
N-Alkyl: 2940 cm$^{-1}$
O-CH$_3$: 2860 cm$^{-1}$
Ester-CO: 1705, 1740 cm$^{-1}$
Amide-CO: 1685 cm$^{-1}$
UV-spectrum (ethanol): λ max 280 nm.

Example 299

1-[4-Amino-3-bromo-5-(N-ethyl-cyclohexylaminomethyl)-benzoyloxymethyl]-4-[1-(4-chlorobenzoyl)-5-methoxy-2-methyl-1H-indole-3-acetoxymethyl]-cyclohexane This compound was prepared from 1-[4-amino-3-bromo-5-(N-ethyl-cyclohexylaminomethyl)-benzoyloxymethyl]-4-hydroxymethyl-cyclohexane and 1-(4-chlorobenzoyl)-5-methoxy-2-methyl-1H-indole-3-acetic acid imidazolide analogous to Example 1. Oil.

IR-spectrum (methylene chloride):
NH$_2$: 3450 cm$^{-1}$
N-Alkyl: 2940 cm$^{-1}$
O-CH$_3$: 2860 cm$^{-1}$
Ester-CO: 1705, 1735 cm$^{-1}$
Amide-CO: 1685 cm$^{-1}$
UV-spectrum (ethanol): λ max 230 nm, 290 nm.

Example 300

1-[4-Amino-3-bromo-5-(N-ethyl-cyclohexylaminomethyl)-benzoyloxy]-2-{2-[(2,6-dichlorophenyl)-amino]-phenylacetoxy}-2-phenyl-ethane This compound was prepared from 2-[4-amino-3-bromo-5-(N-ethyl-cyclohexylaminomethyl)-benzoyloxy]-1-phenylethyl chloride and sodium 2-[(2,6-dichlorophenyl)-amino]-phenylacetate analogous to Example 8. Oil.

IR-spectrum (methylene chloride):
NH$_2$: 3450 cm$^{-1}$
N-alkyl: 2940 cm$^{-1}$
Ester-CO: 1725 cm$^{-1}$
UV-spectrum (ethanol): λ max 282 nm.

Example 301

1-[4-Amino-3-bromo-5-(N-ethyl-cyclohexylaminomethyl)-benzoyloxymethyl]-4-{2-[(2,6-dichlorophenyl)-amino]-phenylacetoxymethyl}-benzene This compound was prepared from 1-[4-amino-3-bromo-5-(N-ethyl-cyclohexylaminomethyl)-benzoyloxymethyl]-4-hydroxymethyl-benzene and sodium 2-[(2,6-dichlorophenyl)-amino]-phenylacetate analogous to Example 8. Oil.

IR-spectrum (methylene chloride):
NH$_2$: 3450 cm$^{-1}$
N-Alkyl: 2940 cm$^{-1}$
Ester-CO: 1710 cm$^{-1}$ UV-spectrum (ethanol): λ max 283 nm.

Example 302

1-[4-Amino-3-bromo-5-(N-ethyl-cyclohexylaminomethyl)-benzoyloxy-methyl]-4-{2-[(2,6-dichlorophenyl)-amino]-phenylacetoxymethyl}-cyclohexane This compound was prepared from 1-[4-amino-3-bromo-5-(N-ethyl-cyclohexylaminomethyl)-benzoyloxymethyl]-4-chloromethyl-cyclohexane and sodium 2-[(2,6-dichlorophenyl)-amino]-phenylacetate analogous to Example 8. Oil.

IR-spectrum (methylene chloride):
$NH_2$: 3440 cm$^{-1}$
N-Alkyl: 2430 cm$^{-1}$
Ester-CO: 1705, 1720 cm$^{-1}$
UV-spectrum (ethanol): λ max 283 nm.

The compounds of the present invention, that is, those embraced by formula I above and their non-toxic, pharmacologically acceptable acid addition salts, have useful pharmaceutical properties. More particularly, they exhibit anti-inflammatory activity in warm-blooded animals such as rats.

The anti-inflammatory properties and the toxicities of the compounds of this invention were ascertained by the test methods described below, and Tables I and II show the results of these tests for a few representative species of the genus, where A = 1-[4-amino-3-bromo-5-(N-ethyl-cyclohexylaminomethyl)-benzoyloxy]-2-[1-(4-chlorobenzoyl)-5-methoxy-2-methyl-1H-indole-3-acetoxy]-ethane hydrochloride, B = 1-(4-amino-3-bromo-5-diethylaminomethyl-benzoyloxy)-2-[1-(4-chlorobenzoyl)-5-methoxy-2-methyl-1H-indole-3-acetoxy]-ethane hydrochloride, C = 1-[4-amino-3-bromo-5-(N-ethyl-cyclohexylaminomethyl)-benzoyloxy]-5-{2-[(2,6-dichlorophenyl)-amino-]-phenylacetoxy}-n-pentane hydrochloride, D = 1-[4-amino-3-bromo-5-(N-ethyl-cyclohexylaminomethyl)-benzoyloxy]-6-{2-[(2,6-dichlorophenyl)-amino]-phenylacetoxy}-n-hexane hydrochloride, E = N-{2-[4-amino-3-bromo-5-(N-ethyl-cyclohexylaminomethyl)-benzoyloxy]-ethyl}-N-{2-[2-[(2,6-dichlorophenyl)-amino-]-phenylacetoxy]-ethyl}-ethylamine dihydrochloride, F = 2-[4-amino-3-bromo-5-(N-ethyl-cyclohexylaminomethyl)-benzoyloxy]-2'-{2-[(2,6-dichlorophenyl)-amino]-phenylacetoxy}-diethyloxide, hydrochloride, G = 2-[4-amino-3-bromo-5-(N-ethyl-cyclohexylaminomethyl)-benzoyloxy]-2'-{2-[(2,6-dichlorophenyl)-amino]-phenylacetoxy}-diethylsulfide hydrochloride, H = 1-[4-amino-3-bromo-5-(N-ethyl-cyclohexylaminomethyl)-benzoyloxy]-2-(3-benzoyl-α-methyl-phenylacetoxy)-ethane hydrochloride, I = N-{2-[4-amino-3-bromo-5-(N-ethyl-cyclohexylaminomethyl)-benzoyloxy]-ethyl}-N-[2-(3-benzoyl-α-methylphenylacetoxy)-ethyl]-n-propylamine, J = 1-[4-amino-3-bromo-5-(N-ethyl-cyclohexylaminomethyl)-benzoyloxy]-3-[(+)-6-methoxy-α-methyl-2-naphthalineacetoxy]-n-propane, K = 2-[4-amino-3-bromo-5-(N-ethyl-cyclohexylaminomethyl)-benzoyloxy]-2'-[(+)-6-methoxy-α-methyl-2-naphthalineacetoxy]-diethylsulfide, L = 2-[4-amino-3-bromo-5-(N-ethyl-cyclohexylaminomethyl)-benzoyloxy]-2'-[α-methyl-4-(2-methylpropyl)-phenylacetoxy]-diethyloxide, and M = N-{2-[4-amino-3-bromo-5-(N-ethyl-cyclohexylaminomethyl)-benzoyloxy]-ethyl}-N-{2-[α-methyl-4-(2-methylpropyl)-phenylacetoxy]-ethyl}-n-propylamine.

1. Antiphlogistic activity:

Method:

In rats (own breed) of both sexes with a body weight of 120 to 150 gm an edema was induced according to the method of WINTER et al. [J. Pharmacol. 141, 369 (1963)] by subplantar injection of 0.05 ml of a solution of carrageenin in a 0.85% sodium chloride solution.

The test compound was administered by means of an esophageal tube 60 minutes before inducing the edema as a trituration in 1% methyl cellulose (1 ml/100 gm animal). Measurement of the thickness of the paws was effected 3 hours after inducing the edema, using the technique of DOEPFNER and CERLETTI [Int. Arch. Allergy Appl. Immunol. 12, 89 (1958)].

From the changes in the swelling values caused by the administration of different doses, after linear regression analysis according to LINDER [Statistiche Methoden, 4th Edition, pp. 148–162, Birkhäuser, Basle (1964)], an $ED_{35}$ according to FIELLER [Quart. J. Pharm. Pharmacol. 17, 117–123 (1944)] was calculated, that is, the dose which produced a 35% reduction of the swelling.

The results from this test are shown in the following table:

TABLE I

| Compound | $n_1$ | $n_2$ | $ED_{35}$ mg/kg |
|---|---|---|---|
| A | 4 | 10 | 84.7 |
| B | 4 | 10 | 35.5 |
| C | 4 | 10 | 9.9 |
| D | 3 | 10 | 29.9 |
| E | 4 | 10 | 18.9 |
| F | 3 | 10 | 49.2 |
| G | 3 | 10 | 6.7 |
| H | 5 | 10 | 15.8 |
| I | 3 | 10 | 2.7 |
| J | 3 | 10 | 36.1 |
| K | 3 | 10 | 36.2 |
| L | 4 | 10 | 24.7 |
| M | 3 | 10 | 53.3 |

$n_1$ = the number of the tested doses
$n_2$ = the number of the animals/dose.

2. Acute toxicity:

The test compound at a dosage of 100 mg/kg as a trituration in 1% methyl cellulose (1 ml/100 gm animal) was administered to rats (own breed) of both sexes by means of an esophageal tube. The animals were observed for 24 hours.

The results obtained from this test are recorded in the following table:

TABLE II

| Compound | Dose mg/kg | n | Ratio of animals with a symptom | Ratio of dead animals |
|---|---|---|---|---|
| A | 100 | 10 | 0/10 | 0/10 |
| B | 100 | 10 | 0/10 | 0/10 |
| C | 100 | 10 | 0/10 | 0/10 |
| D | 100 | 10 | 0/10 | 0/10 |
| E | 100 | 10 | 0/10 | 0/10 |
| F | 100 | 10 | 0/10 | 0/10 |
| G | 100 | 10 | 0/10 | 0/10 |
| H | 100 | 10 | 0/10 | 0/10 |

TABLE II-continued

| Compound | Dose mg/kg | n | Ratio of animals with a symptom | Ratio of dead animals |
|---|---|---|---|---|
| I | 100 | 10 | 0/10 | 0/10 |
| J | 100 | 10 | 0/10 | 0/10 |
| K | 100 | 10 | 0/10 | 0/10 |
| L | 100 | 10 | 0/10 | 0/10 |
| M | 100 | 10 | 0/10 | 0/10 | n = number of animals

The present invention is thus based on the recognition that, by ester- and/or amide-type linkage of an antiphlogistic containing a carboxyl group with a substituted aminomethyl-aminobenzoic acid via a bridge, new benzoyl derivatives with anti-inflammatory properties are obtained which surprisingly possess an excellent compatibility.

Based on their pharmacological properties, the compounds of the present invention are useful for the treatment of inflammatory disorders, such as periarthritis humeroscapularis, bursitis, synovitis, tendinitis, tendovaginitis, gout, polyarthritis, arthorisis deform., spondylitis ankylopoietica and lumbago.

For pharmaceutical purposes the compounds of the present invention are administered to warm-blooded animals perorally, parenterally, rectally or topically as active ingredients in customary pharmaceutical compositions, that is, compositions consisting essentially of an inert pharmaceutical carrier and an effective amount of the active ingredient, such as tablets, coated pills, capsules, wafers, powders, solutions, suspensions, emulsions, syrups, suppositories, ointments, creams and the like. An effective anti-inflammatory amount of the compounds according to the present invention is from 1.4 to 8.5 mgm/kg body weight, preferably 4.3 to 6.4 mgm/kg body weight, 1 to 3 times daily.

The following examples illustrate a few pharmaceutical compositions comprising a compound of the present invention as an active ingredient and represent the best modes contemplated of carrying out the invention. The parts are parts by weight unless otherwise specified.

Example 303

Tablets

The tablet composition is compounded from the following ingredients:

| | |
|---|---|
| 1-[4-Amino-3-bromo-5-(N—ethyl-cyclo-hexylaminomethyl)-benzoyloxy]-2-[1-(4-chlorobenzoyl)-5-methoxy-2-methyl-1H-indole-3-acetoxy]-ethane hydrochloride | 100.0 parts |
| Lactose | 80.0 parts |
| Corn starch | 34.0 parts |
| Polyvinyl pyrrolidone | 4.0 parts |
| Magnesium stearate | 2.0 parts |
| Total | 220.0 parts |

Preparation:

The active ingredient, the lactose, the corn starch and the polyvinyl pyrrolidone are intimately admixed with each other, the mixture is moistened with ethanol, the moist mass is granulated through a 1.6 mm-mesh screen, and the granulate is dried at 45° C. The dry granulate is again passed through the screen, admixed with the magnesium stearate, and the composition is compressed into 220 mgm-tablets in a conventional tablet making machine. Each tablet is an oral dossage unit composition containing 100 mgm of the active ingredient.

Example 304

Coated tablets

The tablet core composition is compounded from the following ingredients:

| | |
|---|---|
| 1-[4-Amino-3-bromo-5-(N—ethyl-cyclohexylaminomethyl)-benzoyl-oxy]-2-[1-(4-chlorobenzoyl)-5-methoxy-2-methyl-1H-indole-3-acetoxy]-ethane hydrochloride | 100.0 parts |
| Secondary calcium phosphate | 110.0 parts |
| Corn starch | 40.0 parts |
| Polyvinyl pyrrolidone | 8.0 parts |
| Magnesium stearate | 2.0 parts |
| Total | 260.0 parts |

Preparation:

The active ingredient, calcium phosphate, the corn starch and the polyvinyl pyrrolidone are intimately admixed with each other, the mixture is moistened with ethanol, the moist mass is granulated through a 1.6 mm-mesh screen, and the granulate is dried at 45° C. The dry granulate is again passed through the screen, admixed with the magnesium stearate, and the composition is compressed into 260 mgm-tablet cores which are subsequently coated with a thin shell consisting essentially of sugar and talcum and polished with bees wax. Each coated tablet is an oral dosage unit composition containing 100 mgm of the active ingredient.

Example 305

Suppositories

The suppository composition is compounded from the following ingredients:

| | |
|---|---|
| 1-[4-Amino-3-bromo-5-(N—ethyl-cyclohexylaminomethyl)-benzoyl-oxy]-2-[1-(4-chlorobenzoyl)-5-methoxy-2-methyl-1H-indole-3-acetoxy]-ethane hydrochloride | 0.200 parts |
| Suppository base (e.g. cocoa butter) | 1.500 parts |
| Total | 1.700 parts |

Preparation:

The suppository base is melted and cooled to 38° C., the pulverized active ingredient is homogeneously blended into the molten base, the mixture is cooled to 35° C., and 1.7 gm-portions of the composition are poured into cooled suppository molds and allowed to harden therein. Each suppository is a rectal dosage unit composition containing 200 mgm of the active ingredient.

Example 306

Capsules

The capsule filler composition is compounded from the following ingredients:

| | |
|---|---|
| 1-[4-Amino-3-bromo-5-(N—ethyl-cyclohexylaminomethyl)-benzoyl-oxy]-2-[1-(4-chlorobenzoyl)-5-methoxy-2-methyl-1H-indole-3-acetoxy]-ethane hydrochloride | 200.0 parts |
| Corn starch | 60.0 parts |

83

-continued

| | |
|---|---|
| Lactose, pulverized | 37.0 parts |
| Magnesium stearate | 3.0 parts |
| Total | 300.0 parts |

Preparation:

The active ingredient, the corn starch, the lactose and the previously screened magnesium stearate are admixed with each other, the mixture is screened and then homogeneously blended in a powder mixer, and 300 mgm-portions of the composition are filled into No. 1 hard gelatin capsules. Each capsule is an oral dosage unit composition containing 200 mgm of the active ingredient.

Example 307

Anhydrous ointment

The ointment composition is compounded from the following ingredients:

| | |
|---|---|
| 1-[4-Amino-3-bromo-5-(N—ethyl-cyclohexylaminomethyl)-benzoyl-oxy]-2-[1-(4-chlorobenzoyl)-5-methoxy-2-methyl-1H-indole-3-acetoxy]-ethane hydrochloride | 1.0 parts |
| Paraffin oil, thin liquid | 10.0 parts |
| Cetyl alcohol | 0.5 parts |
| Wool grease | 5.0 parts |
| White vaseline | 83.5 parts |
| Total | 100.0 parts |

Preparation:

A mixture of the white vaseline, the wool grease, the cetyl alcohol and the paraffin oil is melted at 70° C., and the molten mixture is passed through a sieve into a mixing kettle and cooled to about 60° C. The micronized active ingredient is blended in portions into the still liquid molten mixture with the aid of a homogenizer, and the resulting mixture is stirred for ten minutes more and then cooled to about 35° C. while stirring. The ointment is finally allowed to cool to room temperature without stirring; it is a topical composition containing 1% of the active ingredient.

Any one of the other compounds embraced by formula I or a non-toxic, pharmacologically acceptable acid addition salt thereof may be substituted for the particular active ingredient in Examples 303 through 307. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

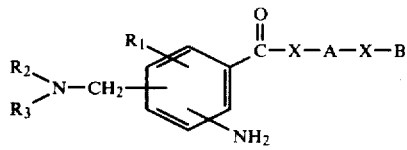

wherein each X, which may be identical to or different from the other X, is oxygen or imino;
 $R_1$ is hydrogen, fluorine, chlorine or bromine;
 $R_2$ and $R_3$ are each hydrogen; unsubstituted or monosubstituted alkyl of 1 to 6 carbon atoms, where the substituent is phenyl or dialkylamino with 1 to 3 carbon atoms in each alkyl moiety; or cycloalkyl of 5 to 7 carbon atoms;
 A is cycloalkylene of 5 to 7 carbon atoms; unsubstituted or substituted alkylene of 2 to 10 carbon atoms, where the substituents are one to two alkyls of 1 to 3 carbon atoms each, one to two carbalkoxys of 2 to 4 carbon atoms each, one to two phenyls, one to four hydroxyls, one halomethyl, one hydroxymethyl, one alkanoyloxy of 1 to 18 carbon atoms, one alkanoyloxymethyl of 1 to 18 carbon atoms in the alkanoyl moiety or one

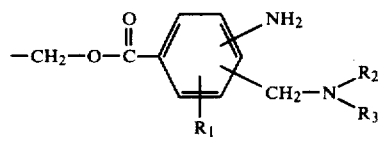

where $R_1$, $R_2$ and $R_3$ have the meanings previously defined; or alkylene of 2 to 10 carbon atoms interrupted by oxygen, sulfur, sulfoxide, sulfonyl, phenyl, cyclohexyl, or unsubstituted or substituted imino, where the substituent on the imino group is alkyl of 1 to 6 carbon atoms, phenyl or phenylalkyl of 1 to 3 carbon atoms in the alkyl moiety; and
 B is 1-(4-chlorobenzoyl)-5-methoxy-2-methyl-1H-indole-3-acetyl;
 or a non-toxic, pharmacologically acceptable acid addition salt thereof.

2. A compound of claim 1,
where each X, which may be identical to or different from the other X, is oxygen or imino;
 $R_1$ is hydrogen, chlorine or bromine;
 $R_2$ and $R_3$ are each hydrogen, alkyl of 1 to 4 carbon atoms, cycloalkyl of 5 to 7 carbon atoms, benzyl or 2-diethylamino-ethyl;
 A is straight alkylene of 2 to 10 carbon atoms; substituted ethylene, where the substituents are one to two methyls, one to two alkoxycarbonyls of 2 to 3 carbon atoms each, one to two phenyls, one hydroxyl, one chloromethyl, one hydroxymethyl, one 4-amino-3-bromo-5-(N-ethyl-cyclohexylaminomethyl)-benzoyloxymethyl or one alkanoyloxymethyl of 1 to 18 carbon atoms in the alkanoyl moiety; 2-substituted propylene, where the substituents are one hydroxyl, one alkanoyloxy of 1 to 18 carbon atoms, or two alkyls of 1 to 3 carbon atoms each; tetrahydroxy-n-hexylene; cyclohexylene; straight alkylene of 4 to 6 carbon atoms which is interrupted between the 2- and 3-carbon atoms or the 3- and 4-carbon atoms by oxygen, sulfur, sulfoxide, sulfonyl, amino, phenylamino, benzylamino, or alkylamino of 1 to 4 carbon atoms in the alkyl moiety; 1,4-cyclohexane-dimethylene or p-xylylene; and B is 1-(4-chlorobenzoyl)-5-methoxy-2-methyl-1H-indole-3-acetyl;

or a non-toxic, pharmacologically acceptable acid addition salt thereof.

3. A compound of claim 1, where X is oxygen;

$R_1$ is bromine;

$R_2$ is methyl or ethyl;

$R_3$ is ethyl or cyclohexyl

A is straight alkylene of 2 to 6 carbon atoms; or straight alkylene of 4 to 6 carbon atoms which is interrupted between the 2- and 3-carbon atoms or between the 3- and 4-carbon atoms by oxygen, sulfur, ethylamino or propylamino; and B is 1-(4-chlorobenzoyl)-5-methoxy-2-methyl-1H-indole-3-acetyl;

or a non-toxic, pharmacologically acceptable acid addition salt thereof.

4. A compound of claim 1, which is 1-[4-amino-3-bromo-5-(N-ethyl-cyclohexylaminomethyl)-benzoyloxy]-2-[1-(4-chlorobenzoyl)-5-methoxy-2-methyl-1H-indole-3-acetoxy]-ethane or a non-toxic, pharmacologically acceptable acid addition salt thereof.

5. A compound of claim 1, which is 1-(4-amino-3-bromo-5-diethylaminomethyl-benzoyloxy)-2-[1-(4-chlorobenzoyl)-5-methoxy-2-methyl-1H-indole-3-acetoxy]-ethane or a non-toxic, pharmacologically acceptable acid addition salt thereof.

6. An anti-inflammatory pharmaceutical composition consisting essentially of an inert pharmaceutical carrier and an effective anti-inflammatory amount of a compound of claim 1.

7. The method of counteracting inflammation in a warm-blooded animal, which comprises perorally, parenterally, rectally or topically administering to said animal an effective anti-inflammatory amount of a compound of claim 1.

* * * * *